US012642815B2

(12) United States Patent
Klaerner et al.

(10) Patent No.: US 12,642,815 B2
(45) Date of Patent: *Jun. 2, 2026

(54) HCL-BINDING COMPOSITIONS FOR AND METHODS OF TREATING ACID-BASE DISORDERS

(71) Applicant: Renibus Therapeutics, Inc., Southlake, TX (US)

(72) Inventors: Gerrit Klaerner, Hillsborough, CA (US); Eric F. Connor, Los Gatos, CA (US); Randi K. Gbur, Brisbane, CA (US); Matthew J. Kade, Berkeley, CA (US); Paul H. Kierstead, Oakland, CA (US); Jerry M. Buysse, Los Altos, CA (US); Michael J. Cope, Berkeley, CA (US); Kalpesh N. Biyani, Dublin, CA (US); Son H. Nguyen, Milpitas, CA (US); Scott M. Tabakman, Palo Alto, CA (US)

(73) Assignee: Renibus Therapeutics, Inc., Southlake, TX (US)

( * ) Notice: Subject to any disclaimer, the term of this patent is extended or adjusted under 35 U.S.C. 154(b) by 76 days.

This patent is subject to a terminal disclaimer.

(21) Appl. No.: 17/878,192

(22) Filed: Aug. 1, 2022

(65) Prior Publication Data

US 2025/0009785 A1 Jan. 9, 2025

Related U.S. Application Data

(63) Continuation of application No. 16/099,024, filed as application No. PCT/US2017/031344 on May 5, 2017, now Pat. No. 11,406,661.

(60) Provisional application No. 62/414,966, filed on Oct. 31, 2016, provisional application No. 62/408,885, filed on Oct. 17, 2016, provisional application No. 62/350,686, filed on Jun. 15, 2016, provisional application No. 62/333,059, filed on May 6, 2016.

(51) Int. Cl.

| | |
|---|---|
| ***A61K 31/785*** | (2006.01) |
| ***A61K 9/00*** | (2006.01) |
| ***A61K 9/14*** | (2006.01) |
| ***A61K 33/00*** | (2006.01) |
| ***A61P 3/12*** | (2006.01) |
| ***A61P 13/12*** | (2006.01) |
| ***A61P 43/00*** | (2006.01) |
| ***C08F 8/02*** | (2006.01) |
| *C08F 226/02* | (2006.01) |
| *C08F 226/04* | (2006.01) |

(52) U.S. Cl.

CPC .......... *A61K 31/785* (2013.01); *A61K 9/0053* (2013.01); *A61K 9/14* (2013.01); *A61K 33/00* (2013.01); *A61P 3/12* (2018.01); *A61P 13/12* (2018.01); *A61P 43/00* (2018.01); *C08F 8/02* (2013.01); *C08F 226/02* (2013.01); *C08F 226/04* (2013.01)

(58) Field of Classification Search

CPC ................................ A61K 9/14; A61K 31/785

See application file for complete search history.

(56) References Cited

U.S. PATENT DOCUMENTS

| | | | |
|---|---|---|---|
| 5,496,545 | A | 3/1996 | Holmes-Farley et al. |
| 5,643,951 | A | 7/1997 | Stacpoole et al. |
| 5,648,355 | A | 7/1997 | Theoharides |
| 5,667,775 | A | 9/1997 | Holmes-Farley et al. |
| 5,679,717 | A | 10/1997 | Mandeville, III et al. |
| 5,753,706 | A | 5/1998 | Hsu |
| 6,271,264 | B1 | 8/2001 | Dhal et al. |
| 6,444,221 | B1 | 9/2002 | Shapiro |
| 6,468,964 | B1 | 10/2002 | Rowe |
| 6,485,703 | B1 | 11/2002 | Cote et al. |
| 6,726,905 | B1 | 4/2004 | Mandeveille, III et al. |
| 6,733,780 | B1 | 5/2004 | Tyler et al. |
| 6,877,408 | B2 | 4/2005 | Kubota et al. |
| 7,335,795 | B2 | 2/2008 | Chang et al. |
| 7,342,083 | B2 | 3/2008 | Chang et al. |
| 7,449,605 | B2 | 11/2008 | Chang et al. |
| 7,459,502 | B2 | 12/2008 | Connor et al. |
| 7,608,674 | B2 | 10/2009 | Connor et al. |
| 7,754,199 | B2 | 7/2010 | Chang et al. |

(Continued)

FOREIGN PATENT DOCUMENTS

| | | | |
|---|---|---|---|
| CN | 1503676 | A | 6/2004 |
| CN | 1878822 | A | 12/2006 |

(Continued)

OTHER PUBLICATIONS

Beaubien-Souligny et al., The effect of lanthanum carbonate on metabolic acidosis in patients with chronic kidney disease stage IV, V and V-D, Int Urol Nephrol, 7pg. 2015.

(Continued)

*Primary Examiner* — Micah Paul Young

(74) *Attorney, Agent, or Firm* — Jeff B. Vockrodt; CM Law

(57) ABSTRACT

Pharmaceutical compositions for and methods of treating an animal, including a human, and methods of preparing such compositions. The pharmaceutical compositions contain nonabsorbable compositions and may be used, for example, to treat diseases or other metabolic conditions in which removal of protons, the conjugate base of a strong acid and/or a strong acid from the gastrointestinal tract would provide physiological benefits such as normalizing serum bicarbonate concentrations and the blood pH in an animal, including a human.

15 Claims, 13 Drawing Sheets

(56) References Cited

U.S. PATENT DOCUMENTS

| | | | |
|---|---|---|---|
| 7,767,229 | B1 | 8/2010 | Milne et al. |
| 7,767,768 | B2 | 8/2010 | Chang et al. |
| 7,767,851 | B2 | 8/2010 | Kwok et al. |
| 7,815,898 | B2 | 10/2010 | Savica |
| 7,846,425 | B2 | 12/2010 | Hedge et al. |
| 7,964,182 | B2 | 6/2011 | Omray et al. |
| 7,985,418 | B2 | 7/2011 | Bhagat et al. |
| 8,003,600 | B2 | 8/2011 | Hageman |
| 8,084,397 | B2 | 12/2011 | Li et al. |
| 8,163,799 | B2 | 4/2012 | Dhal et al. |
| 8,187,634 | B2 | 5/2012 | Hedge et al. |
| 8,273,384 | B2 | 9/2012 | Wurzberger |
| 8,349,305 | B2 | 1/2013 | Chang et al. |
| 8,394,416 | B2 | 3/2013 | Bianchi et al. |
| 8,399,025 | B2 | 3/2013 | Roy et al. |
| 8,445,014 | B2 | 5/2013 | Charmot et al. |
| 8,530,519 | B2 | 9/2013 | Ueno |
| 8,586,097 | B2 | 11/2013 | Liu et al. |
| 8,842,086 | B2 | 9/2014 | Ogg |
| 8,986,669 | B2 | 3/2015 | Huval et al. |
| 9,205,107 | B2 | 12/2015 | Klaerner et al. |
| 9,925,214 | B2 | 3/2018 | Klaerner et al. |
| 9,993,500 | B2 | 6/2018 | Klaerner et al. |
| 10,363,268 | B2 | 7/2019 | Klaerner et al. |
| 10,369,169 | B1 | 8/2019 | Klaerner et al. |
| 10,391,118 | B2 | 8/2019 | Klaerner et al. |
| 10,934,380 | B1 | 3/2021 | Klaerner et al. |
| 11,197,887 | B2 | 12/2021 | Klaerner et al. |
| 11,266,684 | B2 | 3/2022 | Klaerner et al. |
| 11,311,571 | B2 | 4/2022 | Klaerner et al. |
| 11,406,661 | B2 * | 8/2022 | Klaerner .................. A61K 9/14 |
| 11,992,501 | B2 * | 5/2024 | Klaerner ................ A61K 33/00 |
| 2002/0110560 | A1 | 8/2002 | Demuth et al. |
| 2002/0159968 | A1 | 10/2002 | Petersen et al. |
| 2003/0039627 | A1 | 2/2003 | Holmes-Farley et al. |
| 2003/0091530 | A1 | 5/2003 | Goto et al. |
| 2003/0092782 | A1 | 5/2003 | Goto et al. |
| 2004/0059065 | A1 | 3/2004 | Goto et al. |
| 2005/0090553 | A1 | 4/2005 | Shapiro |
| 2005/0220750 | A1 | 10/2005 | Robert et al. |
| 2005/0220751 | A1 | 10/2005 | Charmot et al. |
| 2005/0220752 | A1 | 10/2005 | Charmot et al. |
| 2005/0220889 | A1 | 10/2005 | Charmot et al. |
| 2005/0220890 | A1 | 10/2005 | Charmot et al. |
| 2005/0234129 | A1 | 10/2005 | Sutton et al. |
| 2006/0024336 | A1 | 2/2006 | Charmot et al. |
| 2006/0034847 | A1 | 2/2006 | Yun et al. |
| 2007/0098678 | A1 | 5/2007 | Bhagat et al. |
| 2007/0135335 | A1 | 6/2007 | Collier et al. |
| 2007/0293429 | A1 | 12/2007 | Nestor |
| 2008/0125394 | A1 | 5/2008 | Savica |
| 2008/0200533 | A1 | 8/2008 | Krishnan |
| 2008/0207766 | A1 | 8/2008 | Devane |
| 2008/0214440 | A1 | 9/2008 | Nestor |
| 2008/0248012 | A1 | 10/2008 | Suematsu |
| 2008/0317729 | A1 | 12/2008 | Kasch et al. |
| 2009/0053317 | A1 | 2/2009 | Vigo et al. |
| 2009/0131338 | A1 | 5/2009 | Saou et al. |
| 2009/0155368 | A1 | 6/2009 | Holmes-Farley et al. |
| 2009/0155370 | A1 | 6/2009 | Cope et al. |
| 2009/0156647 | A1 | 6/2009 | Molino et al. |
| 2009/0162314 | A1 | 6/2009 | Huval et al. |
| 2009/0325860 | A1 | 12/2009 | Costantino et al. |
| 2010/0008988 | A1 | 1/2010 | Mehta et al. |
| 2010/0035992 | A1 | 2/2010 | Bhushan et al. |
| 2010/0080858 | A1 | 4/2010 | Satou et al. |
| 2010/0104527 | A1 | 4/2010 | Mansky et al. |
| 2010/0111891 | A1 | 5/2010 | Albrecht et al. |
| 2010/0113479 | A1 | 5/2010 | Choudhury et al. |
| 2010/0124542 | A1 | 5/2010 | Dhal et al. |
| 2010/0129309 | A1 | 5/2010 | Dhal et al. |
| 2010/0135950 | A1 | 6/2010 | Huval et al. |
| 2010/0166696 | A1 | 7/2010 | Dhal et al. |
| 2010/0166861 | A1 | 7/2010 | Lynch |
| 2010/0189679 | A1 | 7/2010 | Inoue et al. |
| 2010/0234309 | A1 | 9/2010 | Cooper et al. |
| 2010/0316589 | A1 | 12/2010 | Charmot et al. |
| 2011/0064820 | A1 | 3/2011 | Omray et al. |
| 2011/0081413 | A1 | 4/2011 | Omray |
| 2011/0142952 | A1 | 6/2011 | Harris et al. |
| 2011/0189121 | A1 | 8/2011 | Genth et al. |
| 2011/0263493 | A1 | 10/2011 | Dugi et al. |
| 2011/0268666 | A1 | 11/2011 | Friedman et al. |
| 2012/0219626 | A1 | 8/2012 | Osinga |
| 2012/0259098 | A1 | 10/2012 | Baker, Jr. et al. |
| 2012/0288471 | A1 | 11/2012 | Huval et al. |
| 2013/0022570 | A1 | 1/2013 | Kopping et al. |
| 2013/0130995 | A1 | 5/2013 | Currie et al. |
| 2013/0131202 | A1 | 5/2013 | Albrecht et al. |
| 2013/0137772 | A1 | 5/2013 | Bergeron |
| 2013/0156720 | A1 | 6/2013 | Currie |
| 2013/0189215 | A1 | 7/2013 | Lees et al. |
| 2013/0189216 | A1 | 7/2013 | Albrecht et al. |
| 2013/0251667 | A1 | 9/2013 | Dhal et al. |
| 2013/0266533 | A1 | 10/2013 | Dhal et al. |
| 2013/0345303 | A1 | 12/2013 | Poradosu et al. |
| 2014/0105848 | A1 | 4/2014 | Klaerner et al. |
| 2015/0056451 | A1 | 2/2015 | Klaerner et al. |
| 2015/0079168 | A1 | 3/2015 | Poradosu et al. |
| 2016/0074430 | A1 | 3/2016 | Klaerner et al. |
| 2017/0095441 | A1 | 4/2017 | Kwok et al. |
| 2018/0021370 | A1 | 1/2018 | Klaerner et al. |
| 2018/0280428 | A1 | 10/2018 | Klaerner et al. |
| 2019/0134075 | A1 | 5/2019 | Klaerner et al. |
| 2019/0134076 | A1 | 5/2019 | Klaerner et al. |
| 2019/0209607 | A1 | 7/2019 | Klaerner et al. |
| 2020/0054669 | A1 | 2/2020 | Klaerner et al. |
| 2020/0289551 | A1 | 9/2020 | Klaerner et al. |
| 2020/0306209 | A1 | 10/2020 | Klaerner et al. |
| 2021/0106611 | A1 | 4/2021 | Klaerner et al. |
| 2021/0187011 | A1 | 6/2021 | Klaerner et al. |
| 2021/0205351 | A1 | 7/2021 | Klaerner et al. |
| 2021/0347925 | A1 | 11/2021 | Klaerner et al. |
| 2022/0062328 | A1 | 3/2022 | Klaerner et al. |
| 2022/0096534 | A1 | 3/2022 | Klaerner et al. |

FOREIGN PATENT DOCUMENTS

| | | | |
|---|---|---|---|
| CN | 101687961 | | 3/2010 |
| CN | 105377270 | | 3/2016 |
| EP | 2016947 | | 1/2009 |
| EP | 2168992 | | 3/2010 |
| EP | 1931689 | | 2/2015 |
| KR | 1020070026338 | | 3/2007 |
| RU | 2160742 | | 12/2000 |
| RU | 2008136081 | | 3/2010 |
| RU | 2392926 | | 6/2010 |
| WO | 9505184 | | 2/1995 |
| WO | 9940990 | | 8/1999 |
| WO | 2005041900 | A2 | 5/2005 |
| WO | 2005041902 | | 5/2005 |
| WO | 2005092039 | | 10/2005 |
| WO | 2007022435 | | 2/2007 |
| WO | 2007038801 | | 4/2007 |
| WO | 2007056405 | | 5/2007 |
| WO | 2008011047 | | 1/2008 |
| WO | 2008027551 | | 3/2008 |
| WO | 2008103368 | | 8/2008 |
| WO | 2009023544 | | 2/2009 |
| WO | 2009097127 | | 8/2009 |
| WO | 2009125433 | | 10/2009 |
| WO | 2012011063 | A1 | 1/2012 |
| WO | 2014197725 | | 12/2014 |
| WO | 2015066593 | | 2/2015 |
| WO | 2016094685 | A1 | 6/2016 |
| WO | 2017193024 | | 11/2017 |
| WO | 2017193050 | | 11/2017 |
| WO | 2017193064 | | 11/2017 |
| WO | 2019090176 | | 5/2019 |
| WO | 2019090177 | | 5/2019 |
| WO | 2019236124 | | 12/2019 |

(56) References Cited

FOREIGN PATENT DOCUMENTS

| | | |
|---|---|---|
| WO | 2019236636 | 12/2019 |
| WO | 2019236639 | 12/2019 |

OTHER PUBLICATIONS

Bezzaoucha et al., The role of sevelamer carbonate in increasing serum bicarbonate in hyperphosphatemic pre-dialysis patients who have metabolic acidosis, Intern. Journal of Clinical Pharmacology and Therapeutics, 51(Dec. 2013): 989-990 2013.
Bushinsky et al., Randomized, Controlled Trial of TRC101 to Increase Serum Bicarbonate in Patients with CKD, Clin J Am Soc Nephrol, 13(1): 26-35 2018.
Chen et al., Epidemiology of Acid-Base Derangements in CKD, Adv Chronic Kidney Dis., 24(5):280-288 2017.
Garneata et al., Ketoanalogue-Supplemented Vegetarian Very Low-Protein Diet and CKD Progression, J Am Soc Nephrol 27:2164-2176 2016.
Pai et al., Comparison of Sevelamer Hydrochloride and Sevelamer Carbonate: Risk of Metabolic Acidosis and Clinical Implications, Pharmacotherapy, 29(5):554-561 2009.
Mahajan et al., Daily oral sodium bicarbonate preserves glomerular filtration rate by slowing its decline in early hypertensive nephropathy, Kidney International, 78, 303-309 2010.
Raphael, K.L., Metabolic Acidosis and Subclinical Metabolic Acidosis in CKD, J Am Soc Nephrol 29, 7pg 2017.
Rombola et al, Lanthanum carbonate: a postmarketing observational study of efficacy and safety, Jour Nephrol, 25 (4): 490-496 2012.
Susantitaphong et al., Short- and Long-Term Effects of Alkali Therapy in Chronic Kidney Disease: A Systematic Review. Am J Nephrol, 35:540-547 2012.
Thet et al., Differential effects of phosphate binders on pre-dialysis serum bicarbonate in end-stage kidney disease patients on maintenance haemodialysis, BMC Nephrology, 14:205-215 2013.
Goraya et al., A Comparison of Treating Metabolic Acidosis in CKD Stage 4 Hypertensive Kidney Disease with Fruits and Vegetables or Sodium Bicarbonate, Clin J Am Soc Nephrol 8: 371-381 2013.
Goraya et al., Treatment of metabolic acidosis in patients with stage 3 chronic kidney disease with fruits and vegetables or oral bicarbonate reduces urine angiotensinogen and preserves glomerular filtration rate, Kidney International, 86:1031-1038 2014.
Goraya et al., Management of the Metabolic Acidosis of Chronic Kidney Disease, Adv Chronic Kidney Dis., 24 (5):298-304 2017.
Hatakeyama et al., Switching hemodialysis patients from sevelamer hydrochloride to bixalomer: a single-center, non-randomized analysis of efficacy and effects on gastrointestinal symptoms and metabolic acidosis, BMC Nephrology, 14:222-229 2013.
Husted et al., NaHC03 and NaCl tolerance in chronic renal failure II, Clinical Nephrology, 7(1):21-25 1977.
Lindley et al., Correction of metabolic acidosis after conversion from sevelamer hydrochloride to lanthanum carbonate, NDT Plus, 3:196 2008.
Navaneethan et al., Serum Bicarbonate and Mortality in Stage 3 and Stage 4 Chronic Kidney Disease, Clinical Journal of the American Society of Nephrology, 6(10): 2395-2402 2011.
Russian Federal Institute of Industrial Property, Search Report for 2015155596, 2 pages May 8, 2018.
Patent Cooperation Treaty, International Search Report for PCT/US2018/059092, 3pgs. Jan. 8, 2019.
Kraut, Disturbances in Acid-Base, Potassium, and Sodium Balance in Patients With CKD: New Insights and Novel Therapies, Adv Chronic Kidney Dis., 2017, 24(5): 272-273 2017.
Patent Cooperation Treaty, International Search Report for PCT/US2018/059093, 3pgs. Jan. 8, 2019.
Patent Cooperation Treaty, International Search Report for PCT/US2018/059094, 3pgs. Jan. 8, 2019.
Yang et al., Quality of Life and Its Determinants of Hemodialysis Patients in Taiwan Measured With WHOQOL-BREF (TW), American Journal of Kidney Diseases, 2005, 46(4): 635-641 2005.
Hays et al., Kidney Disease Qua1ity of Life Short Form (KDQOL-SF(tm)), Version 1.3: A Manual for Use and Scoring, retrieved from www.rand.org/content/rand/pubs/papers/2006/p7994.pdf, 42 pgs. 1997.
Wesson et al., Veverimer versus placebo in patients with metabolic acidosis associated with chronic kidney disease: a multicentre, randomised, double-blind, controlled, phase 3 trial, The Lancet, 11 pgs. 2019.
Patent Cooperation Treaty, International Search Report for PCT/US2019/035470, 3 pages Jul. 24, 2019.
Patent Cooperation Treaty, International Search Report for PCT/US2019/035467, 3 pages Aug. 19, 2019.
Abramowitz et al., Effects of Oral Sodium Bicarbonate in Patients with CKD, Clin J Am Soc Nephrol, 8: 714-720 2013.
European Patent Office, Extended Search Report for EP App. 19169259.9, 12 pages Oct. 10, 2019.
Abramowitz, M.K., Acid-Base Balance and Physical Function, Clin J Am Soc Nephrol, 9: 2030-2032 2014.
Abramowitz, M.K., Metabolic Acidosis and Cardiovascular Disease Risk in CKD, Clin J Am Soc Nephrol, 13, 2 pgs. 2018.
Aronson et al., Effects of pH on Potassium: New Explanations for Old Observations, J Am Soc Nephrol, 22: 1981-1989 2011.
Ballasi et al., Correction of metabolic acidosis improves insulin resistance in chronic kidney disease, BMC Nephrology, 17: 158-167 2016.
Wolf et al., The Renin-Angiotensin System and Progression of Renal Disease: From Hemodynamics to Cell Biology, Nephron Physiol, 93: 3-13 2003.
Witham et al., BiCARB results and abstract, 56th European Renal Association—European Dialysis and Transplant Association (ERA-EDTA) Congress, Jun. 13-16, 2019 2019.
Williams et al., Failure of Dietary Protein and Phosphate Restriction to Retard the Rate of Progression of Chronic Renal Failure: A Prospective, Randomized, Controlled Trial, 81(294): 837-855 1991.
Wesson et al., Long-term safety and efficacy of veverimer in patients with metabolic acidosis in chronic kidney disease: a multicentre, randomised, blinded, placebo-controlled, 40-week extension, Lancet, 394(10196): 396-406 2019.
Biggar et al., Sevelamer carbonate for the treatment of hyperphosphatemia in patients with kidney failure (CKD III-V), Expert Opin. Pharmacother, 11(16): 2739-2750 2010.
Bushinsky, D. A., Tolerance to Sodium in Patients With CKD-Induced Metabolic Acidosis: Does the Accompanying Anion Matter?, 73(6): 858-865 2019.
Chen et al., Is an Increased Serum Bicarbonate Concentration during Hemodialysis Associated with an Increased Risk of Death?. Semin. Dial., 27(3): 259-262 2014.
Chen et al., Advances in management of chronic metabolic acidosis in chronic kidney disease, Pharm. Thera., 28: 8 pgs 2019.
Dawson-Hughes et al., Impact of supplementation with bicarbonate on lower-extremity muscle performance in older men and women, Osteoporos Int., 21(7): 1171-1179 2010.
De Brito-Ashurst et al., Acidosis: progression of chronic kidney disease and quality of life, Pediatr Nephrol, 30: 873-879 2015.
De Iorio et al., Very Low-Protein Diet (VLPD) Reduces Metabolic Acidosis in Subjects with Chronic Kidney Disease: The "Nutritional Light Signal" of the Renal Acid Load, Nutrients, 9: 69-82 2017.
De Iorio et al., Treatment of metabolic acidosis with sodium bicarbonate delays progression of chronic kidney disease: the UBI Study, Journal of Nephrology, 32: 989-1001 2019.
Disthabanchong et al., Oral Sodium Bicarbonate Improves Thyroid Function in Predialysis Chronic Kidney Disease, Am J Nephrol., 32: 549-556 2010.
Dobre et al., Serum bicarbonate and cardiovascular events in hypertensive adults: results from the Systolic Blood Pressure Intervention Trial, Nephrol Dial Transplant, 1-8 2019.
Dobre et al., Current Status of Bicarbonate in CKD, J Am Soc Nephrol., 26(3): 515-523 2015.
Dobre et al., Persistent High Serum Bicarbonate and the Risk of Heart Failure in Patients With Chronic Kidney Disease (CKD): A

(56) References Cited

OTHER PUBLICATIONS

Report From the Chronic Renal Insufficiency Cohort (CRIC) Study, J Am Heart Assoc., 17 pgs. 2015.
European Patent Office, Extended European Search Report for 18872862.0, 9 pages Mar. 24, 2022.
United States Patent and Trademark Office, Office Action issued Apr. 13, 2020 for U.S. Appl. No. 16/099,045.
Dobre et al., Serum Bicarbonate and Structural and Functional Cardiac Abnormalities in Chronic Kidney Disease—A Report from the Chronic Renal Insufficiency Cohort Study, Am J Nephrol., 43: 411-420 2016.
Dobre et al., Serum Bicarbonate Concentration and Cognitive Function in Hypertensive Adults, Clin J Am Soc Nephrol., 13(4): 596-603 2018.
Domrongkitchaipron et al., Bone histology and bone mineral density after correction of acidosis in distal renal tubular acidosis, Kidney International., 62: 2160-2166 2002.
Dubey et al., Correction of metabolic acidosis improves muscle mass and renal function in chronic kidney disease stages 3 and 4: a randomized controlled trial, Nephrol Dial Transplant, 9 pgs 2018.
Fan et al., A randomized, crossover design study of sevelamer carbonate powder and sevelamer hydrochloride tablets in chronic kidney disease patients on haemodialysis, European Renal Association European, 5 pgs. 2011.
Gennari et al., Effect of Dietary Protein Intake on Serum Total CO2 Concentration in Chronic Kidney Disease: Modification of Diet in Renal Disease Study Findings, Clin J Am Soc Nephrol., 1: 52-57 2006.
Gonzalez et al., Sevelamer carbonate increases serum bicarbonate in pediatric dialysis patients, Pediatr Nephrol., 25: 373-375 2010.
Greene et al., Role of Aldosterone in the Remnant Kidney Model in the Rat, J. Clin. Invest., 98(4): 1063-1068 1996.
Halperin et al., Ammonium Excretion in Chronic Metabolic Acidosis: Benefits and Risks, American Journal of Kidney Diseases, 14(4): 267-271 1989.
Harris et al., Mechanism of Hyperkalemia-Induced Metabolic Acidosis, J Am Soc Nephrol, 29: 1411-1425 2018.
Jeong et al., Effect of Bicarbonate Supplementation on Renal Function and Nutritional Indices in Predialysis Advanced Chronic Kidney Disease, Electrolyte Blood Press, 12: 80-87 2014.
Ketteler et al., Efficacy and Tolerability of Sevelamer Carbonate in Hyperphosphatemic Patients Who Have Chronic Kidney Disease and Are Not on Dialysis, Clin J Am Soc Nephrol, 3: 1125-1130 2008.
Kittiskulnam et al., Impact of Serum Bicarbonate Levels on Muscle Mass and Kidney Function in Pre-Dialysis Chronic Kidney Disease Patients, Am J Nephrol., 11 pgs 2019.
Kraut et al., Metabolic acidosis: pathophysiology, diagnosis and management, Nature Reviews Nephrology, 6: 274-285 2010.
Mathur et al., Effects of Correction of Metabolic Acidosis on Blood Urea and Bone Metabolism in Patients with Mild to Moderate Chronic Kidney Disease: A Prospective Randomized Single Blind Controlled Trial, Renal Failure, 28: 1-5, 2006.
Melamed et al., Effects of Sodium Bicarbonate in CKD Stages 3 and 4: A Randomized, Placebo-Controlled, Multicenter Clinical Trial, Am J Kidney Dis., 10pgs 2019.
Mircescu et al., Effects of a Supplemented Hypoproteic Diet in Chronic Kidney Disease, Journal of Renal Nutrition, 17(3): 179-188 2007.
Nath et al., Increased Ammoniagenesis as a Determinant of Progressive Renal Injury, Am. Jour. Kid. Dis. 17(6): 654-657 1991.
Nathan et al., The effect of intensive treatment of diabetes on the development and progression of long-term complications in insulin-dependent diabetes mellitus, New Eng. Jour. Med., 329(14): 977-986 1993.
Navaneethan et al., Effects of Treatment of Metabolic Acidosis in CKD a Systematic Review and Meta-Analysis, CJASN, 14: 10 pgs. 2019.
Perry et al., Sevelamer Carbonate: A Review in Hyperphosphataemia in Adults with Chronic Kidney Disease, Drugs, 74: 771-792 2014.
Phisitkul et al., Amelioration of metabolic acidosis in patients with low GFR reduced kidney endothelin production and kidney injury, and better preserved GFR, Kidney International, 77: 617-623 2010.
Pisani et al., 6-tips diet: a simplified dietary approach in patients with chronic renal disease. A clinical randomized trial, Clin Exp Nephrol, 10 pgs 2015.
Mount, D. B., Potassium balance in acid-base disorders, retrieved from www.uptodate.com/contents/potassium-balance-in-acid-base-disorders?search=hyperkalemia%20and%20metabolic%20acidosis&source=search_result&selectedTitle=1~150&usage_type=default&display_rank, 5 pgs 2018.
Raphael et al., Higher serum bicarbonate levels within the normal range are associated with better survival and renal outcomes in African Americans. Kidney International, 79: 356-362 2011.
Raphael et al., Bicarbonate Concentration, Acid-Base Status, and Mortality in the Health, Aging, and Body Composition Study, Clin J Am Soc Nephrol, 11: 9 pgs 2016.
Raphael et al., Urine Ammonium Predicts Clinical Outcomes in Hypertensive Kidney Disease, J Am Soc Nephrol 28: 2483-2490 2017.
Raphael et al., A Randomized Trial Comparing the Safety, Adherence, and Pharmacodynamics Profiles of Two Doses of Sodium Bicarbonate in CKD: the BASE Pilot Trial, JASN 31: 14 pgs 2020.
Raphael K. L., Metabolic Acidosis in CKD: Core Curriculum 2019, AJKD, 13 pgs 2019.
Remuzzi G.., Role of Endothelin in the Development of Glomerulosclerosis, Kidney and Blodd Ress Res., 19: 182-183 1996.
Ruiz-Ortega et al., Involvement of angiotensin II and endothelin in matrix protein production and renal sclerosis, Jour. Hypertension, 12: S51-S58 1994.
Seccia et al., Role of angiotensin II, endothelin-1 and L-type calcium channel in the development of glomerular, tubulointerstitial and perivascular fibrosis, Journal of Hypertension, 26:2022-2029 2008.
Shah et al., Serum Bicarbonate Levels and the Progression of Kidney Disease: A Cohort Study, Am J Kidney Dis 54:270-277 2009.
Stein et al., Role of an improvement in acid-base status and nutrition in CAPD patients, Kidney International, 52: 1089-1095 1997.
Szeto et al., Oral Sodium Bicarbonate for the Treatment of Metabolic Acidosis in Peritoneal Dialysis Patients: A Randomized Placebo-Control Trial, J Am Soc Nephrol 14: 2119-2126 2003.
Tangri et al., A Predictive Model for Progression of Chronic Kidney Disease to Kidney Failure, JAMA, 305(15): 1553-1559 2011.
Wesson D. E., Endogenous Endothelins Mediate Increased Acidification in Remnant Kidneys, J Am Soc Nephrol 12: 1826-1835 2001.
Wesson et al., Angiotensin II receptors mediate increased distal nephron acidification caused by acid retention, Kidney International, 82: 1184-1194 2012.
Wesson et al., Angiotensin II-mediated GFR decline in subtotal nephrectomy is due to acid retention associated with reduced GFR, Nephrol Dial Transplant, 30: 762-770 2015.
European Patent Office, Extended Search Report for EP App. 17793497.3, 11 pages Mar. 17, 2020.
Anonymous, Tricida Announces Positive Topline Phase 1/2 Clinical Trial Results for TRC101 in 135 Subjects with Chronic Kidney Disease and Metabolic Acidosis, Business Wire, 2 pages Jan. 9, 2017.
European Patent Office, Extended Search Report for EP App. 20154562.1, 6 pages Sep. 8, 2020.
Kovacic et al., Metabolic Acidosis of Chronically Hemodialyzed Patients, Am J Nephrol 23:158-164 Mar. 21, 2003.
Witham et al., Clinical and cost-effectiveness of oral sodium bicarbonate therapy for older patients with chronic kidney disease and low-grade acidosis (BiCARB): a pragmatic randomised, double-blind, placebo-controlled trial, BMC Medicine, 18:91, 16 pages 2020.
European Patent Office, Extended European Search Report for EP 19816018.6, 8 pages Feb. 16, 2021.
European Patent Office, Extended European Search Report for App. No. 20204589.4, 12 pages Apr. 30, 2021.

(56) References Cited

OTHER PUBLICATIONS

Kovesdy et al., Association of serum bicarbonate levels with mortality in patients with non-dialysis-dependent CKD, Nephrology Dialysis Transplantation, 4(24): 1232-1237 2008.
Inker et al., GFR Decline as an Alternative End Point to Kidney Failure in Clinical Trials: A Meta-analysis of Treatment Effects From 37 Randomized Trials, American Journal of Kidney Diseases, 64(4): 848-859 2014.
Wesson, D. E., The Continuum of Acid Stress, Clinical Journal of the American Society of Nephrology, 16: 1292-1299 2021.
Madias, N. E., Metabolic Acidosis and CKD Progression, Clinical Journal of the American Society of Nephrology, 16: 310-312 2021.
Steed,et al. Supramolecular Chemistry, Chapter 4 Anion Binding 2nd Edition, John Wiley & Sons, Ltd. West Sussex, UK 216-279 Published 2009.
Adrogue et al., Respiratory Acidosis, Respiratory Alkalosis, and Mixed Disorders in Comprehensive Clinical Nephrology, 4th Edition, 2010, Elsevier Saunders, St. Louis, Missouri, Ch. 14, 176-189.
Ballmer et al., Chronic metabolic acidosis decreases albumin synthesis and induces negative nitrogen balance in humans, The Journal of Clinical Investigation, 1995, 95: 39-45.
Brezina et al., Acid loading during treatment with sevelamer hydrocholoride: Mechanisms and clinical implications, Kidney International, 2004, 66(90): S39-S45.
Chmelarova, Short chain fatty acids and colonic health, Bratisl Lek Listy, 2007, 108(8): 354-358.
D'Agostino et al., Alterations in the ionic composition of icotonic saline solutins instilled into the colon, The Journal of Clinical Investigation, 1953, 32(5): 444-448.
Davis et al., Evaluation of Chlorida/Biocarbonate exchange in the human colon in vivo, The Journal of Clinical Investigation, 1983, 71:201-207.
De Brito-Ashurst et al, Bicarbonate Supplementation Slows Progression of CKD and Improves Nutritional Status, J Am Soc Nephrol, 2009, 20(9): 2075-2084.
Dobre et al., Association of Serum Bicarbonate With Risk of Renal and Cardiovascular Outcomes in CKD: A Report From the Chronic Renal Insufficiency Cohort (CRIC) Study, American Journal of Kidney Diseases, 62(4): 670-678 2013.
Dubose, Jr., et al., Renal Tubular Acidosis in Acid Base and Electrolyte Disorders: A Companion to Brenner & Rector's The Kidney, Elsevier Health Sciences, 2002, Ch. 11, 189-206.
Farwell et al., Serum anion gap, bicarbonate and biomarkers of inflammation in healthy individuals in a national survey, Canadian Medical Association Journal, 2010, 182(2): 137-141.
Fortran et al., Ionic constituents and osmolality of gastric and small-intestinal fluids after eating, New Series, 1966, 11(7):503-521.
Goldberg, Approach to Acid-Base Disorders, Ch 11, 2005, 104-109.
Heart Failure Society of America, HFSA 2010 Guideline Executive Summary Executive Summary: HFSA 2010 Comprehensive Heart Failure Practice Guideline, Journal of Cardiac Failure, 2010, 16(6), 259 pages.
Hospria Sodium Bicarb IV ANDA labels and packaging, 5 pages Revised 2021.
Kielland, J., Individual Activity Coefficients of Ions in Aqueous Solutions, 1937, 59, 1675-1678, retrieved from www.ufscar.br.
Lemann, Jr., et al., Bone buffering of acid and base in humans, Am J Physiol Renal Physiol, 2003, 285:F811-F832.
Lemann, Jr., et al., The Effects of Chronic Acid Loads in Normal Man: Further Evidence for the Participation of Bone Mineral in the Defense against Chronic Metabolic Acidosis, Journal of Clinical Investigation, 1966, 45(10): 1608-1614.
Mitch, W. E., Influence of Metabolic Acidosis on Nutrition, American Journal of Kidney Diseases, vol. 29, No. 5 May 1997: pp. xlvi-xlviii.
National Kidney Foundation, K/DOQI Clinical Practice Guidelines for Bone Metabolism and Disease in Chronic Kidney Disease, 2003, 42(4), Supp. 3.
National Kidney Foundation, K/DOQI Nutrition Guidelines, American Journal of Kidney Diseases, 2000, 35(6), Supp. 2.
Phisitkul et al., Dietary protein causes a decline in the glomerular filtration rate of the remnant kidney mediated by metabolic acidosis and endothelin receptors, Kidney International, 73: 192-199 2008.
Raphael et al., Serum bicarbonate and mortality in adults in NHANES III, Nephrol Dial Transplant, 28: 1207-1213 2013.
Shannon, R.D., Revised Effective Ionic Radii and Systematic Studies of Interatomie Distances in Halides and Chaleogenides, Acta Cryst., 1976, A32: 751-767.
Stevens et al., Electrolyte composition of endoscopically collected duodenal drainage fluid after synthetic porcine secretin stimulation in healthy subjects, Gastrointestinal Endoscopy, 2004, 60(3): 351-355.
Sullivan et al., Halogenated Solvents, Trichloroethylene, and Methylene Chloride in Clinical Environmental Health and Toxic Exposures, 2nd Ed., Ch. 58, 1999, Lippincott Williams & Wilkins, Philadelphia, PA.
Szerlip, Metabolic Acidosis, Ch. 8, p. 74-89, published 2005.
Widmer et al., Serum Electrolyte and Acid Base Composition, Arch Intern Med, 1979, 139, 1099-1102.
Wrong et al., In Vivo dialysis of faeces as a method of stool analysis, Clinical Science, 1967, 33(1): 89-100.
Yaqoob, M. M., Acidosis and progression of chronic kidney disease, Current Opinion in Nephrology and Hypertension, 19:489-492 2010.
Remington, The Science and Practice of Pharmacy, 21st Ed., Edited by D. B. Troy, p. 317-318 and 745-775, Lippincott Williams & Wilkins, Baltimore, Maryland.
Patent Cooperation Treaty, International Search Report and Written Opinion for PCT/US2014/041152, mailed Nov. 27, 2014, 10 pages.
Nakaki et al., Effect of fatty acids on the phosphate binding of TRK-390, a novel, highly selective phosphate-binding polymer, European Journal of Pharmacology, 2013, 714(1-3): 312-317.
Akizawa, et al., Long-Term Treatment of Hyperphosphatemia With Bixalomer in Japanese Hemodialysis Patients, Therapeutic Apheresis and Dialysis, 2013, 17(6): 612-619.
Ito et al., Treatment of Hyperphosphatemia With Bixalomer in Japanese Patients on Long-Term Hemodialysis With Gastrointestinal Symptoms, Therapeutic Apheresis and Dialysis, 2014; 18(Supplement 2):19-23.
Shima et al., Clinical Experiences of Bixalomer Usage at Our Hospital, Therapeutic Apheresis and Dialysis 2014; 18 (Supplement 2):13-18.
Kioussis et al., Reactive nitrogen and phosphorus removal from aquaculture wastewater effluents using polymer hydrogels, Aquacultural Engineering, 2000, 23: 315-332.
Kioussis et al., Phosphate binding polymeric hydrogels for aquaculture wastewater remediation, Aquacultural Engineering, 1999, 19: 163-178.
Kioussis et al., Selective anion sorption and recovery from wastewater by polyelectrolyte hydrogels, Polymer Preprints, 2000, 41(2): 1679-1680.
Patent Cooperation Treaty, International Search Report for PCT/US2015/065041, dated Mar. 22, 2016, 5 pgs.
Patent Cooperation Treaty, Written Opinion issued for PCT/US2015/065041, dated Mar. 22, 2016, 8 pages.
Patent Cooperation Treaty, International Search Report for PCT/US2017/031395, 6 pages Aug. 8, 2017.
Patent Cooperation Treaty, International Search Report for PCT/US2017/031344, 5 pages Aug. 8, 2017.
Inoue et al., Highly selective and low-swelling phosphate-binding polymer for hyperphosphatema therapy, Chem. Letters, 41, 932-933 2012.
Franch et al., Catabolismin Uremia: The Impact of Metabolic Acidosis, J. Am. Soc. Nephrol., 9: S78-S81 1998.
Patent Cooperation Treaty, International Search Report for PCT/US2017/031378, 5 pages Sep. 20, 2017.
European Patent Office, Extended European Search Report issued for App. No. 17177221.3, 8 pages Jan. 23, 2018.

(56) References Cited

OTHER PUBLICATIONS

Akizawa et al., Randomized Controlled Trial of Bixalomer Versus Sevelamer Hydrochloride in Hemodialysis Patients With Hyperphosphatemia, Therapeutic Aphreresis and Dialysis, 18(2):122-131 2014.

Akizawa et al., Bixalomer in Hyperphosphatemic Patients With Chronic Kidney Disease Not on Dialysis: Phase 3 Randomized Trial, Therapeutic Apheresis and Dialysis, 10 pages 2016.

Akizawa et al., Long-Term Safety and Efficacy of Bixalomer in Hyperphosphatemic Patients With Chronic Kidney Disease Not on Dialysis, Therapeutic Apheresis and Dialysis, 7pgs 2017.

NCT02809183, https://clinicaltrials.gov/study/NCT02809183?tab=history&a=2, Sep. 2016, 8 pages.

* cited by examiner

HCL-BINDING COMPOSITIONS FOR AND METHODS OF TREATING ACID-BASE DISORDERS

CROSS-REFERENCE TO RELATED APPLICATIONS

The present application is a continuation of U.S. patent application Ser. No. 16/099,024 filed on Nov. 5, 2018, now U.S. Pat. No. 11,406,661, which is a national stage application of PCT/US2017/031344 filed on May 5, 2017, and claims priority to U.S. provisional application No. 62/414,966 filed on Oct. 31, 2016; U.S. provisional application No. 62/408,885 filed Oct. 17, 2016; U.S. provisional application No. 62/350,686 filed Jun. 15, 2016; and U.S. provisional application No. 62/333,059 filed May 6, 2016, the entire contents of each of which are hereby incorporated by reference as if recited in full herein.

The present invention generally relates to methods of treating acid-base disorders that may be used, for example, in the treatment of metabolic acidosis.

Metabolic acidosis is the result of metabolic and dietary processes that in various disease states create a condition in which non-volatile acids accumulate in the body, causing a net addition of protons ($H^+$) or the loss of bicarbonate ($HCO_3^-$). Metabolic acidosis occurs when the body accumulates acid from metabolic and dietary processes and the excess acid is not completely removed from the body by the kidneys. Chronic kidney disease is often accompanied by metabolic acidosis due to the reduced capacity of the kidney to excrete hydrogen ions secondary to an inability to reclaim filtered bicarbonate ($HCO_3^-$), synthesize ammonia (ammoniagenesis), and excrete titratable acids. Clinical practice guidelines recommend initiation of alkali therapy in patients with non-dialysis-dependent chronic kidney disease (CKD) when the serum bicarbonate level is <22 mEq/L to prevent or treat complications of metabolic acidosis. (Clinical practice guidelines for nutrition in chronic renal failure, K/DOQI, National Kidney Foundation, Am. J. Kidney Dis. 2000; 35:S1-140; Raphael, KL, Zhang, Y, Wei, G, et al. 2013, Serum bicarbonate and mortality in adults in NHANES III, Nephrol. Dial. Transplant 28: 1207-1213). These complications include malnutrition and growth retardation in children, exacerbation of bone disease, increased muscle degradation, reduced albumin synthesis, and increased inflammation. (Leman, J, Litzow, J R, Lennon, E J. 1966. The effects of chronic acid loads in normal man: further evidence for the participation of bone mineral in the defense against chronic metabolic acidosis, J. Clin. Invest. 45:1608-1614; Franch H A, Mitch W E, 1998, Catabolism in uremia: the impact of metabolic acidosis, J. Am. Soc. Nephrol. 9: S78-81; Ballmer, P E, McNurlan, M A, Hulter, H N, et al., 1995, Chronic metabolic acidosis decreases albumin synthesis and induces negative nitrogen balance in humans, J. Clin. Invest. 95: 39-45; Farwell, W R, Taylor, E N, 2010, Serum anion gap, bicarbonate and biomarkers of inflammation in healthy individuals in a national survey, CMAJ 182:137-141). Overt metabolic acidosis is present in a large proportion of patients when the estimated glomerular filtration rate is below 30 ml/min/1.73 $m^2$. (KDOQI bone guidelines: American Journal of Kidney Diseases (2003) 42:S1-S201. (suppl); Widmer B, Gerhardt R E, Harrington J T, Cohen J J, Serum electrolyte and acid base composition: The influence of graded degrees of chronic renal failure, Arch Intern Med 139:1099-1102, 1979; Dobre M, Yang, W, Chen J, et. al., Association of serum bicarbonate with risk of renal and cardiovascular outcomes in CKD: a report from the chronic renal insufficiency cohort (CRIC) study. Am. J. Kidney Dis. 62: 670-678, 2013; Yaqoob, M M. Acidosis and progression of chronic kidney disease. Curr. Opin. Nephrol. Hypertens. 19: 489-492, 2010).

Metabolic acidosis, regardless of etiology, lowers extracellular fluid bicarbonate and, thus, decreases extracellular pH. The relationship between serum pH and serum bicarbonate is described by the Henderson-Hasselbalch equation $$pH = pK' + \log[HCO_3^-]/[(0.03 \times PaCO_2)]$$

where 0.03 is the physical solubility coefficient for $CO_2$, $[HCO_3^-]$ and $PaCO_2$ are the concentrations of bicarbonate and the partial pressure of carbon dioxide, respectively.

There are several laboratory tests that can be used to define metabolic acidosis. The tests fundamentally measure either bicarbonate ($HCO_3^-$) or proton ($H^+$) concentration in various biological samples, including venous or arterial blood. These tests can measure either bicarbonate ($HCO_3^-$) or proton ($H^+$) concentration by enzymatic methodology, by ion selective electrodes or by blood gas analysis. In both the enzymatic and ion selective electrode methods, bicarbonate is "measured." Using blood gas analysis, bicarbonate level can be calculated using the Henderson-Hasselbalch equation.

Arterial blood gas (ABG) analysis is commonly performed for clinical evaluation, but the procedure has certain limitations in the form of reduced patient acceptability because of painful procedure and the potential to cause complications such as arterial injury, thrombosis with distal ischaemia, haemorrhage, aneurysm formation, median nerve damage and reflex sympathetic dystrophy. Venous blood gas (VBG) analysis is a relatively safer procedure as fewer punctures are required thus reducing the risk of needle stick injury to the health care workers. Therefore, as set out below, when the invention requires assessment of metabolic acidosis, it is preferred to complete this assessment using VBG analysis. Any measurements specified herein are preferably achieved by VBG analysis where possible, for example measurements of blood or serum bicarbonate levels.

The most useful measurements for the determination of acidosis rely on a measurement of the venous plasma bicarbonate (or total carbon dioxide [$tCO_2$]), or arterial plasma bicarbonate (or total carbon dioxide [$tCO_2$]), serum electrolytes $Cl^-$, $K^+$, and $Na^+$, and a determination of the anion gap. In the clinical laboratory, measurement of venous plasma or serum electrolytes includes an estimation of the $tCO_2$. This measurement reflects the sum of circulating $CO_2$ [i.e., the total $CO_2$ represented by bicarbonate ($HCO_3^-$), carbonic acid, ($H_2CO_3$) and dissolved $CO_2$ ($0.03 \times PCO_2$)]. $tCO_2$ can also be related to $HCO_3^-$ by using a simplified and standardized form of the Henderson-Hasselbalch equation: $tCO_2 = HCO_3^- + 0.03\ PCO_2$, where $PCO_2$ is the measured partial pressure of $CO_2$. Since $HCO_3^-$ concentration is greater than 90% of the $tCO_2$, and there are small amounts of $H_2CO_3$, then venous $tCO_2$ is often used as a reasonable approximation of the venous $HCO_3^-$ concentration in the blood. Especially during chronic kidney disease, an abnormal plasma $HCO_3^-$ value <22 mEq/L generally indicates metabolic acidosis.

Changes in serum $Cl^-$ concentration can provide additional insights into possible acid-base disorders, particularly when they are disproportionate to changes in serum $Na^+$ concentration. When this occurs, the changes in serum $Cl^-$ concentration are typically associated with reciprocal changes in serum bicarbonate. Thus, in metabolic acidosis with normal anion gap, serum $Cl^-$ increases >105 mEq/L as serum bicarbonate decreases <22 mEq/L.

Arterial blood gases are used to identify the type of an acid-base disorder and to determine if there are mixed disturbances. In general, the result of arterial blood gas measures should be coordinated with history, physical exam and the routine laboratory data listed above. An arterial blood gas measures the arterial carbon dioxide tension ($P_aCO_2$), acidity (pH), and the oxygen tension ($P_aO_2$). The $HCO_3^-$ concentration is calculated from the pH and the $PaCO_2$. Hallmarks of metabolic acidosis are a pH<7.35, $P_aCO_2$<35 mm Hg and $HCO_3^-$<22 mEq/L. The value of $P_aO_2$ (normal 80-95 mmHg) is not used in making the diagnosis of metabolic acidosis but may be helpful in determining the cause. Acid-base disturbance are first classified as respiratory or metabolic. Respiratory disturbances are those caused by abnormal pulmonary elimination of $CO_2$, producing an excess (acidosis) or deficit (alkalosis) of $CO_2$ (carbon dioxide) in the extracellular fluid. In respiratory acid-base disorders, changes in serum bicarbonate ($HCO_3^-$) are initially a direct consequence of the change in $PCO_2$ with a greater increase in $PCO_2$ resulting in an increase in $HCO_3^-$. (Adrogue H J, Madias N E, 2003, Respiratory acidosis, respiratory alkalosis, and mixed disorders, in Johnson R J, Feehally J (eds): Comprehensive Clinical Nephrology. London, C V Mosby, pp. 167-182). Metabolic disturbances are those caused by excessive intake of, or metabolic production or losses of, nonvolatile acids or bases in the extracellular fluid. These changes are reflected by changes in the concentration of bicarbonate anion ($HCO_3^-$) in the blood; adaptation in this case involves both buffering (immediate), respiratory (hours to days) and renal (days) mechanisms. (DuBose T D, MacDonald G A: renal tubular acidosis, 2002, in DuBose T D, Hamm L L (eds): Acid-base and electrolyte disorders: A companion to Brenners and Rector's the Kidney, Philadelphia, WB Saunders, pp. 189-206).

The overall hydrogen ion concentration in the blood is defined by the ratio of two quantities, the serum $HCO_3^-$ content (regulated by the kidneys) and the $PCO_2$ content (regulated by the lungs) and is expressed as follows:

$$[H^+] \propto (PCO_2/[HCO_3^-])$$

The consequence of an increase in the overall hydrogen ion concentration is a decline in the major extracellular buffer, bicarbonate. Normal blood pH is between 7.38 and 7.42, corresponding to a hydrogen ion ($H^+$) concentration of 42 to 38 nmol/L (Goldberg M: Approach to Acid-Base Disorders. 2005. In Greenberg A, Cheung AK (eds) Primer on Kidney Diseases, National Kidney Foundation, Philadelphia, Elsevier-Saunders, pp. 104-109.). Bicarbonate ($HCO_3^-$) is an anion that acts to buffer against pH disturbances in the body, and normal levels of plasma bicarbonate range from 22-26 mEq/L (Szerlip H M: Metabolic Acidosis, 2005, in Greenberg A, Cheung A K (eds) Primer on Kidney Diseases, National Kidney Foundation, Philadelphia, Elsevier-Saunders, pp. 74-89.). Acidosis is the process which causes a reduction in blood pH (acidemia) and reflects the accumulation of hydrogen ion ($H^+$) and its consequent buffering by bicarbonate ion ($HCO_3^-$) resulting in a decrease in serum bicarbonate. Metabolic acidosis can be represented as follows:

$$2\,CO_2 + 2\,H_2O \rightleftharpoons H_2CO_3 + \underset{\substack{\downarrow \\ \text{low}}}{HCO_3^-} + \underset{\substack{\uparrow \\ \text{high}}}{H^+}$$

(Clinical practice guidelines for nutrition in chronic renal failure. K/DOQI, National Kidney Foundation. Am. J. Kidney Dis. 2000; 35:S1-140). Using this balance equation, the loss of one $HCO_3^-$ is equivalent to the addition of one $H^+$ and conversely, the gain of one $HCO_3^-$ is equivalent to the loss of one $H^+$. Thus, changes in blood pH, particularly increases in $H^+$ (lower pH, acidosis) can be corrected by increasing serum $HCO_3^-$ or, equivalently, by decreasing serum $H^+$.

In order to maintain extracellular pH within the normal range, the daily production of acid must be excreted from the body. Acid production in the body results from the metabolism of dietary carbohydrates, fats and amino acids. Complete oxidation of these metabolic substrates produces water and $CO_2$. The carbon dioxide generated by this oxidation (~20,000 mmol/day) is efficiently exhaled by the lungs, and represents the volatile acid component of acid-base balance.

In contrast, nonvolatile acids (~50-100 mEq/day) are produced by the metabolism of sulfate- and phosphate-containing amino acids and nucleic acids. Additional nonvolatile acids (lactic acid, butyric acid, acetic acid, other organic acids) arise from the incomplete oxidation of fats and carbohydrates, and from carbohydrate metabolism in the colon, where bacteria residing in the colon lumen convert the substrates into small organic acids that are then absorbed into the bloodstream. The impact of short chain fatty acids on acidosis is somewhat minimized by anabolism, for example into long-chain fatty acids, or catabolism to water and $CO_2$.

The kidneys maintain pH balance in the blood through two mechanisms: reclaiming filtered $HCO_3^-$ to prevent overall bicarbonate depletion and the elimination of nonvolatile acids in the urine. Both mechanisms are necessary to prevent bicarbonate depletion and acidosis.

In the first mechanism, the kidneys reclaim $HCO_3^-$ that is filtered by the glomerulus. This reclamation occurs in the proximal tubule and accounts for ~4500 mEq/day of reclaimed $HCO_3^-$. This mechanism prevents $HCO_3^-$ from being lost in the urine, thus preventing metabolic acidosis. In the second mechanism, the kidneys eliminate enough $H^+$ to equal the daily nonvolatile acid production through metabolism and oxidation of protein, fats and carbohydrates. Elimination of this acid load is accomplished by two distinct routes in the kidney, comprising active secretion of $H^+$ ion and ammoniagenesis. The net result of these two interconnected processes is the elimination of the 50-100 mEq/day of nonvolatile acid generated by normal metabolism.

Thus, normal renal function is needed to maintain acid-base balance. During chronic kidney disease, filtration and reclamation of $HCO_3^-$ is impaired as is generation and secretion of ammonia. These deficits rapidly lead to chronic metabolic acidosis which is, itself, a potent antecedent to end-stage renal disease. With continued acid production from metabolism, a reduction in acid elimination will disturb the $H^+/HCO_3^-$ balance such that blood pH falls below the normal value of pH=7.38-7.42.

Acid-base disorders are common in chronic kidney disease and heart failure patients. Chronic kidney disease (CKD) progressively impairs renal excretion of the approximately 1 mmol/kg body weight of hydrogen ions generated in healthy adults (Yaqoob, M M. 2010, Acidosis and progression of chronic kidney disease, Curr. Opin. Nephrol. Hyperten. 19:489-492.). Metabolic acidosis, resulting from the accumulation of acid ($H^+$) or depletion of base ($HCO_3^-$) in the body, is a common complication of patients with CKD, particularly when the glomerular filtration rate (GFR, a measure of renal function) falls below 30 ml/min/1.73 $m^2$. Metabolic acidosis has profound long term effects on protein and muscle metabolism, bone turnover and the development of renal osteodystrophy. In addition, metabolic acidosis influences a variety of paracrine and endocrine functions, again with long term consequences such as increased inflammatory mediators, reduced leptin, insulin resistance, and increased corticosteroid and parathyroid hormone production (Mitch W E, 1997, Influence of metabolic acidosis on nutrition, Am. J. Kidney Dis. 29:46-48.). The net effect of sustained metabolic acidosis in the CKD patient is loss of bone and muscle mass, a negative nitrogen balance, and the acceleration of chronic renal failure due to hormonal and cellular abnormalities (De Brito-Ashurst I, Varagunam M, Raftery M J, et al, 2009, Bicarbonate supplementation slows progression of CKD and improves nutritional status, J. Am. Soc. Nephrol. 20: 2075-2084). Conversely, the potential concerns with alkali therapy in CKD patients include expansion of extracellular fluid volume associated with sodium ingestion, resulting in the development or aggravation of hypertension, facilitation of vascular calcification, and the decompensation of existing heart failure. CKD patients of moderate degree (GFR at 20-25% of normal) first develop hyperchloremic acidosis with a normal anion gap due to the inability to reclaim filtered bicarbonate and excrete proton and ammonium cations. As they progress toward the advanced stages of CKD the anion gap increases, reflective of the continuing degradation of the kidney's ability to excrete the anions that were associated with the unexcreted protons. Serum bicarbonate in these patients rarely goes below 15 mmol/L with a maximum elevated anion gap of approximately 20 mmol/L. The non-metabolizable anions that accumulate in CKD are buffered by alkaline salts from bone (Lemann J Jr, Bushinsky D A, Hamm L L Bone buffering of acid and base in humans. Am. J. Physiol Renal Physiol. 2003 November, 285(5):F811-32).

The annual age-related decline in glomerular filtration rate (GFR) after the age of 40 is 0.75-1.0 ml/min/1.73 $m^2$ in normal individuals. In CKD patients with fast progression, a steeper decline of >4 ml/min/1.73 $m^2$ annually can be seen. Glomerular filtration rate or estimated glomerular filtration rate is typically used to characterize kidney function and the stage of chronic kidney disease. The five stages of chronic kidney disease and the GFR for each stage is as follows:

Stage 1 with normal or high GFR (GFR>90 mL/min/1.73 $m^2$)

Stage 2 Mild CKD (GFR=60-89 mL/min/1.73 $m^2$)

Stage 3A Moderate CKD (GFR=45-59 mL/min/1.73 $m^2$)

Stage 3B Moderate CKD (GFR=30-44 mL/min/1.73 $m^2$)

Stage 4 Severe CKD (GFR=15-29 mL/min/1.73 $m^2$)

Stage 5 End Stage CKD (GFR<15 mL/min/1.73 $m^2$).

In one outcome study, De Brito-Ashurst et al showed that bicarbonate supplementation preserves renal function in CKD (De Brito-Ashurst I, Varagunam M, Raftery M J, et al, 2009, Bicarbonate supplementation slows progression of CKD and improves nutritional status, J. Am. Soc. Nephrol. 20: 2075-2084). The study randomly assigned 134 adult patients with CKD (creatinine clearance [CrCl]15 to 30 ml/min per 1.73 $m^2$) and serum bicarbonate 16 to 20 mmol/L to either supplementation with oral sodium bicarbonate or standard of care for 2 years. The average dose of bicarbonate in this study was 1.82 g/day, which provides 22 mEq of bicarbonate per day. The primary end points were rate of CrCl decline, the proportion of patients with rapid decline of CrCl (>3 ml/min per 1.73 $m^2$/yr), and end-stage renal disease ("ESRD") (CrCl<10 ml/min). Compared with the control group, decline in CrCl was slower with bicarbonate supplementation (decrease of 1.88 ml/min per 1.73 $m^2$ for patients receiving bicarbonate versus a decrease of 5.93 ml/min per 1.73 $m^2$ for control group; P<0.0001). Patients supplemented with bicarbonate were significantly less likely to experience rapid progression (9% versus 45%; relative risk 0.15; 95% confidence interval 0.06 to 0.40; P<0.0001). Similarly, fewer patients supplemented with bicarbonate developed ESRD (6.5% versus 33%; relative risk 0.13; 95% confidence interval 0.04 to 0.40; P<0.001).

Among the various aspects of the present disclosure, the following is a useful guide for one method for treating metabolic acidosis (without wishing to be bound by theory). When an $H^+$ is pumped into the stomach a $HCO_3^-$ enters the systemic circulation and raises the serum bicarbonate concentration. The initial binding of gastric $H^+$ to a nonabsorbable composition as described herein results in $HCO_3^-$ entering the systemic circulation and raising the serum bicarbonate concentration. The more $H^+$ bound the greater the increase in systemic $HCO_3^-$. The binding of $Cl^-$ the nonabsorbable composition prevents subsequent exchange of luminal $Cl^-$ for $HCO_3^-$ which would counteract the initial rise in $HCO_3^-$. The analogous clinical situation to administering the composition is vomiting. Administration of the composition is essentially causing the loss of gastric HCl as in vomiting. If a person vomits they lose gastric HCl and have an increase in serum bicarbonate. The increase in serum bicarbonate persists only if they are not given a lot of oral $Cl^-$, for example as NaCl, which would allow subsequent exchange of intestinal $Cl^-$ for $HCO_3^-$ and dissipate the increase in serum bicarbonate concentration. The disclosure is not limited by these requirements, and instead they are set out in full below.

Among the various aspects of the present disclosure may be noted a method of treating an individual afflicted with a chronic acid/base disorder characterized by a baseline serum bicarbonate value of less than 22 mEq/l. The method comprises oral administration of a pharmaceutical composition comprising a polymeric composition having the capacity to bind HCl as it transits the digestive system.

Another aspect of the present disclosure is a method of treating an individual afflicted with an acid-base disorder characterized by a baseline serum bicarbonate value of less than 22 mEq/l, the method comprising oral administration of a daily dose of a pharmaceutical composition having the capacity to remove at least 5 meq of HCl as it transits the digestive system to achieve a clinically significant increase in the serum bicarbonate value of at least 1 mEq/l from baseline within a treatment period not greater than 1 month.

Another aspect of the present disclosure is a composition for use in a method of treating metabolic acidosis in an adult human patient by increasing that patient's serum bicarbonate value by at least 1 mEq/L over 15 days of treatment (i.e., within 15 days of treatment), said composition being a nonabsorbable composition having the capacity to remove HCl from the patient. In this aspect, the composition may be administered orally, and so would be an orally administered nonabsorbable composition as defined herein.

Another aspect of the present disclosure is a composition for use in a method of treating metabolic acidosis in an adult human patient, said patient having a serum bicarbonate level of less than 20 mEq/L prior to treatment, said composition being a nonabsorbable composition having the capacity to remove HCl from the patient. In this aspect, the composition may be administered orally, and so would be an orally administered nonabsorbable composition as defined herein.

In certain embodiments, the orally administered composition comprises cations (such as $Na^+$, $K^+$, $Mg^{2+}$, $Ca^{2+}$ $Li^+$, or a combination thereof) that are exchanged for protons as the composition transits the digestive system, and the protons are then excreted from the body along with the nonabsorbable composition upon defecation. The net effect is reduction in protons in the body, in exchange for an increase in one or more cations. In this embodiment, the pharmaceutical composition may also optionally comprise a pharmaceutically acceptable carrier, diluent or excipient, or a combination thereof that does not significantly interfere with the proton-binding characteristics of the composition in vivo. Optionally, the pharmaceutical composition may also comprise an additional therapeutic agent.

In certain embodiments, the orally administered composition comprises anions that are exchanged for chloride ions and if the anion comprised by the orally administered composition is a stronger base (e.g., $OH^-$) than the removed base (e.g., $Cl^-$, $HSO_4^-$, or $SO_4^{2-}$), the net effect is the removal of a strong acid from the body (e.g., HCl or $H_2SO_4$) in exchange for a weak acid (e.g., $H_2O$). In this embodiment, the pharmaceutical composition may also optionally comprise a pharmaceutically acceptable carrier, diluent or excipient, or a combination thereof that does not significantly interfere with the chloride-binding characteristics of the nonabsorbable composition in vivo. Optionally, the pharmaceutical composition may also comprise an additional therapeutic agent.

In certain embodiments, the orally administered composition is a neutral composition having the capacity to bind and remove a strong acid, such as HCl or $H_2SO_4$, from the body upon oral administration. The composition may, but does not necessarily, introduce (i.e., by ion exchange) counterbalancing cations or anions in the process of removing the acid. In this embodiment, binding of both ionic species of HCl ($H^+$ and $Cl^-$) may be achieved through favorable surface energy of the bulk material, which can include hydrogen bonding and other interactions as well as ionic interactions. Complexation of HCl can occur on functional groups that are dehydrated and upon administration in an acidic aqueous medium, result in the hydrochloride salt of the functional group.

Among the various aspects of the present disclosure may further be noted a method of treating an individual afflicted with a chronic acid/base disorder comprising oral administration of a pharmaceutical composition containing a nonabsorbable composition having the capacity to bind protons and chloride ions as it transits the digestive system and remove the bound protons and chloride ions from the individual's digestive system via defecation. In each of these embodiments, the pharmaceutical composition may also optionally comprise a pharmaceutically acceptable carrier, diluent or excipient, or a combination thereof that does not significantly interfere with the chloride-binding characteristics of the nonabsorbable composition in vivo. Optionally, the pharmaceutical composition may also comprise an additional therapeutic agent.

In those embodiments in which the composition binds chloride ions, it is generally preferred that the composition selectively bind chloride ions relative to other physiologically significant competing anions such as bicarbonate equivalent anions, phosphate anions, and the conjugate bases of bile and fatty acids that are present in the GI tract. Stated differently, it is generally preferred that the nonabsorbable composition remove more chloride ions than any other competing anion in the GI tract.

It is generally preferred that the pharmaceutical composition bind protons without delivering sodium, potassium, calcium, magnesium, and/or other electrolytes in exchange for the protons in an amount that is physiologically detrimental. As a result, treatment with the pharmaceutical composition will not significantly contribute to edema, hypertension, hyperkalemia, hypercalcemia or a similar disorder associated with an elevated load of sodium, potassium, calcium or other electrolyte. Similarly, in those embodiments in which the composition binds protons, it is generally preferred that the composition bind protons without removing an amount of sodium, potassium, calcium, magnesium and/or other electrolytes along with the protons. As a result, treatment with the composition will not significantly contribute to hypotension, hypokalemia, hypocalcemia or other disorder associated with a depressed serum concentration of sodium, potassium, calcium, magnesium or other electrolyte.

In certain embodiments, the composition comprises a polymer having the ability to bind and maintain their ability to bind proton and anions at the physiological conditions found along the gastrointestinal (GI) lumen. These conditions can change according to dietary intake (see, for example, Fordtran J, Locklear T. Ionic constituents and osmolality of gastric and small-intestinal fluids after eating. Digest Dis Sci. 1966; 11(7):503-21) and location along the GI tract (Binder, H et al. Chapters 41-45 in "Medical Physiology", 2nd Edition, Elsevier [2011]. Boron and Boulpaep [Ed.]). Rapid binding of proton and chloride in the stomach and small intestine is desirable. High binding levels and selectivity for chloride later in the GI tract (lower small intestine and large intestine) is also desirable. In general, the polymers also preferably have a pKa such that the majority of amines are protonated under the various pH and electrolyte conditions encountered along the GI tract and are thereby capable of removing proton, along with an appropriate counter anion (preferably chloride), from the body into the feces.

Since the stomach is an abundant source of HCl, and the stomach is the first site of potential HCl binding (after the mouth), and since residence time in the stomach is short (gastric residence half-life of approximately 90 minutes), compared to the rest of the GI tract (small intestine transit time of approximately 4 hours; whole gut transit time of 2-3 days; Read, N W et al. Gastroenterology [1980]79:1276), it is desirable for the polymer of the present disclosure to demonstrate rapid kinetics of proton and chloride binding in the lumen of this organ, as well as in in vitro conditions designed to mimic the stomach lumen (e.g. SGF). Phosphate is a potential interfering anion for chloride binding in the stomach and small intestine, where phosphate is mostly absorbed (Cross, H S et al Miner Electrolyte Metab [1990] 16:115-24). Therefore rapid and preferential binding of chloride over phosphate is desirable in the small intestine and in in vitro conditions designed to mimic the small intestine lumen (e.g. SIB). Since the transit time of the colon is slow (2-3 days) relative to the small intestine, and since conditions in the colon will not be encountered by an orally administered polymer until after stomach and small intestine conditions have been encountered, kinetics of chloride binding by a polymer of the present disclosure do not have to be as rapid in the colon or in in vitro conditions designed to mimic the late small intestine/colon. It is, however, important that chloride binding and selectivity over other interfering anions is high, for example, at 24 and/or 48 hours or longer.

Other aspects and features will be in part apparent and in part pointed out hereinafter.

BRIEF DESCRIPTION OF THE DRAWINGS

FIGS. 13A, 138, 13C and 13D are graphs showing the changes in serum bicarbonate (FIG. 13A), serum chloride (FIG. 138), serum sodium (FIG. 13C) and serum potassium (FIG. 13D) for the four TRC101 active arms (combined) vs the two placebo arms (pooled) over time for the study described more fully in Example 3 (Parts 1 and 2).

ABBREVIATIONS AND DEFINITIONS

Figure 1A:
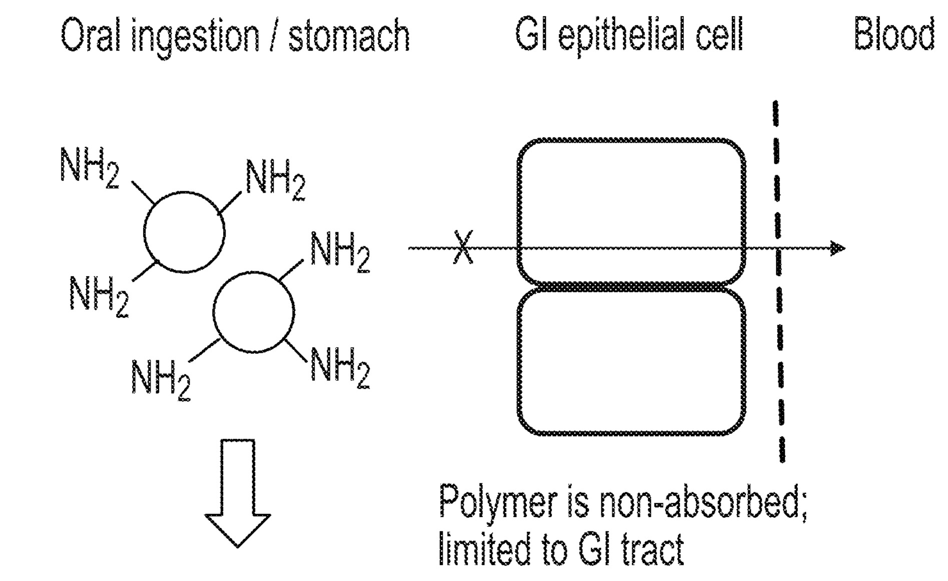
FIG. 1A-1C is a flow chart schematically depicting the mechanism of action of the polymer when passing through the gastrointestinal tract of an individual from oral ingestion/stomach (FIG. 1A), to the upper GI tract (FIG. 1B) to the lower GI tract/colon (FIG. 1C).

The following definitions and methods are provided to better define the present invention and to guide those of ordinary skill in the art in the practice of the present invention. Unless otherwise noted, terms are to be understood according to conventional usage by those of ordinary skill in the relevant art.

The term "absorption capacity" as used herein in connection with a polymer and a swelling agent (or in the case of a mixture of swelling agents, the mixture of swelling agents) is the amount of the swelling agent (or such mixture) absorbed during a period of at least 16 hours at room temperature by a given amount of a dry polymer (e.g., in the form of a dry bead) immersed in an excess amount of the swelling agent (or such mixture).

The term "acrylamide" denotes a moiety having the structural formula $H_2C{=}CH{-}C(O)NR{-}*$, where * denotes the point of attachment of the moiety to the remainder of the molecule and R is hydrogen, hydrocarbyl, or substituted hydrocarbyl.

The term "acrylic" denotes a moiety having the structural formula $H_2C{=}CH{-}C(O)O{-}*$, where * denotes the point of attachment of the moiety to the remainder of the molecule.

The term "adult" refers to an individual over 18 years of age.

The term "alicyclic", "alicyclo" or "alicyclyl" means a saturated monocyclic group of 3 to 8 carbon atoms and includes cyclopentyl, cyclohexyl, cycloheptyl, and the like.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n-butyl, isobutyl, sec-butyl, tert-butyl, pentyl, iso-amyl, hexyl and the like, and alkenyl moieties of comparable chain length.

The term "alkanol" denotes an alkyl moiety that has been substituted with at least one hydroxyl group. In some embodiments, alkanol groups are "lower alkanol" groups comprising one to six carbon atoms, one of which is attached to an oxygen atom. In other embodiments, lower alkanol groups comprise one to three carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about four carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkyl group" as used, either alone or within other terms such as "haloalkyl group," "aminoalkyl group" and "alkylamino group", encompasses saturated linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkylamino group" refers to amino groups directly attached to the remainder of the molecule via the nitrogen atom of the amino group and wherein the nitrogen atom of the alkylamino group is substituted by one or two alkyl groups. In some embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino, pentamethyleneamine and the like.

The term "allyl" denotes a moiety having the structural formula $H_2C{=}CH{-}CH_2{-}$, where * denotes the point of attachment of the moiety to the remainder of the molecule and the point of attachment is to a heteroatom or an aromatic moiety.

The term "allylamine" denotes a moiety having the structural formula $H_2C{=}CH{-}CH_2N(X_8)(X_9)$, wherein $X_8$ and $X_9$ are independently hydrogen, hydrocarbyl, or substituted hydrocarbyl, or $X_8$ and $X_9$ taken together form a substituted or unsubstituted alicyclic, aryl, or heterocyclic moiety, each as defined in connection with such term, typically having from 3 to 8 atoms in the ring.

The term "amine" or "amino" as used alone or as part of another group, represents a group of formula $-N(X_8)(X_9)$, wherein $X_8$ and $X_9$ are independently hydrogen, hydrocarbyl, or substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring.

The term "aminoalkyl group" encompasses linear or branched alkyl groups having one to about ten carbon atoms, any one of which may be substituted with one or more amino groups, directly attached to the remainder of the molecule via an atom other than a nitrogen atom of the amine group(s). In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The terms "anion exchange material" and "cation exchange material" take their normal meaning in the art. For example, the terms "anion exchange material" and "cation exchange material" refer to materials that exchange anions and cations, respectively. Anion and cation exchange materials are typically water-insoluble substances which can exchange some of their cations or anions, respectively, for similarly charged anions or cations contained in a medium with which they are in contact. Anion exchange materials may contain positively charged groups, which are fixed to the backbone materials and allow passage of anions but reject cations. A non-exhaustive list of such positively charged groups includes: amino group, alkyl substituted phosphine, and alkyl substituted sulphides. A non-exhaustive list of cation or anion exchange materials includes: clays (e.g., bentonite, kaolinite, and illite), vermiculite, zeolites (e.g., analcite, chabazite, sodalite, and clinoptilolite), synthetic zeolites, polybasic acid salts, hydrous oxides, metal ferrocyanides, and heteropolyacids. Cation exchange materials can contain negatively charged groups fixed to the backbone material, which allow the passage of cations but reject anions. A non-exhaustive list of such negatively charged groups includes: sulphate, carboxylate, phosphate, and benzoate.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 5 to 10 carbon atoms, typically 5 to 7 carbon atoms, and more typically 5 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "bead" is used to describe a crosslinked polymer that is substantially spherical in shape.

The term "bicarbonate equivalent" is used to describe an organic acid or anion that yields bicarbonate when metabolized. Citrate and succinate are exemplary bicarbonate equivalents.

The term "binds" as used herein in connection with a polymer and one or more ions, that is, a cation (e.g. "proton-binding" polymer) and an anion, is an "ion-binding" polymer and/or when it associates with the ion, generally though not necessarily in a non-covalent manner, with sufficient association strength that at least a portion of the ion remains bound under the in vitro or in vivo conditions in which the polymer is used for sufficient time to effect a removal of the ion from solution or from the body.

The term "ceramic material" takes its normal meaning in the art. In certain embodiments, the term "ceramic material" refers to an inorganic, nonmetallic, solid material comprising metal, nonmetal or metalloid atoms primarily held in ionic and covalent bonds. A non-exhaustive list of examples of ceramic materials includes: barium titanate, bismuth strontium calcium copper oxide, boron oxide, earthenware, ferrite, lanthanum carbonate, lead zirconate, titanate, magnesium diboride, porcelain, sialon, silicon carbide, silicon nitride, titanium carbide, yttrium barium copper oxide, zinc oxide, zirconium dioxide, and partially stabilised zirconia. In certain embodiments, the term "clinically significant increase" as used herein in connection with a treatment refers to a treatment that improves or provides a worthwhile change in an individual from a dysfunctional state back to a relatively normal functioning state, or moves the measurement of that state in the direction of normal functioning, or at least a marked improvement to untreated. A number of methods can be used to calculate clinical significance. A non-exhaustive list of methods for calculating clinical significance includes: Jacobson-Truax, Gulliksen-Lord- Novick, Edwards-Nunnally, Hageman-Arrindell, and Hierarchical Linear Modeling (HLM).

The term "crosslinker" as used, either alone or within other terms, encompasses hydrocarbyl or substituted hydrocarbyl, linear or branched molecules capable of reacting with any of the described monomers, or the infinite polymer network, as described in Formula 1, more than one time. The reactive group in the crosslinker can include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, α,β-unsaturated carbonyls, ketones, aldehydes, pentafluoroaryl groups, vinyl, allyl, acrylate, methacrylate, acrylamide, methacrylamide, styrenic, acrylonitriles and combinations thereof. In one exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

The term "diallylamine" denotes an amino moiety having two allyl groups.

The terms "dry bead" and "dry polymer" refer to beads or polymers that contain no more than 5% by weight of a non-polymer swelling agent or solvent. Often the swelling agent/solvent is water remaining at the end of a purification. This is generally removed by lyophilization or oven drying before storage or further crosslinking of a preformed amine polymer. The amount of swelling agent/solvent can be measured by heating (e.g., heating to 100-200° C.) and measuring the resulting change in weight. This is referred to a "loss on drying" or "LOD."

The term "estimated glomerular filtration rate" or eGFR refers to an estimate of the glomerular filtration rate and is estimated from the serum level of an endogenous filtration marker. Creatinine is a commonly used endogenous filtration marker in clinical practice and several equations have been proposed for estimating the glomerular filtration rate. As used herein, all eGFR values may be determined according to the CKD-EPI equation (Levey et al., A New Equation to Estimate Glomerular Filtration Rate. Ann Intern Med. 2009; 150:604-612):

$$GFR = 41 * \min(Scr/\kappa,\ 1)^{\alpha} * \max(Scr/\kappa,\ 1)^{-1.209} * 0.993^{Age} * 1.018[\text{if female}] * 1.159[\text{if black}]$$

wherein Scr is serum creatinine (mg/dL), κ is 0.7 for females and 0.9 for males, α is −0.329 for females and −0.411 for males, min indicates the minimum of Scr/κ or 1, and max indicates the maximum of Scr/κ or 1.

The term "ethereal" denotes a moiety having an oxygen bound to two separate carbon atoms as depicted the structural formula $*—H_xC—O—CH_x—*$, where * denotes the point of attachment to the remainder of the moiety and x independently equals 0, 1, 2, or 3.

The term "gel" is used to describe a crosslinked polymer that has an irregular shape.

The term "glomerular filtration rate" or GFR is the volume of fluid filtered from the renal (kidney) glomerular capillaries into the Bowman's capsule per unit time. GFR cannot be measured directly; instead, it is measured indirectly (mGFR) as the clearance of an exogenous filtration marker (e.g., inulin, iothalamate, iohexol, etc.) or estimated (eGFR) using an endogenous filtration marker.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaliphatic" describes a chain of 1 to 25 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., $—CH(OH)—CH(NH_2)—$ where the carbon atom is a member of a chain of atoms) or it may be one of the chain atoms (e.g., —ROR— or —RNHR— where each R is aliphatic). Heteroaliphatic encompasses heteroalkyl and heterocyclo but does not encompass heteroaryl.

The term "heteroalkyl" describes a fully saturated heteroaliphatic moiety.

The term "heteroaryl" means a monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

The term "heteroatom" means an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The term "heterocyclo," "heterocyclic," or heterocyclyl" means a saturated or unsaturated group of 4 to 8 ring atoms in which one or two ring atoms are heteroatom such as N, O, B, P and $S(O)_n$, where n is an integer from 0 to 2, the remaining ring atoms being carbon. Additionally, one or two ring carbon atoms in the heterocyclyl ring can optionally be replaced by a —C(O)— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

"Initiator" is a term used to describe a reagent that initiates a polymerization.

The term "measured glomerular filtration rate" or "mGFR" refers to a measurement of the glomerular filtration rate using any chemical (e.g., inulin, iothalamate, iohexol, etc.) that has a steady level in the blood, and is freely filtered but neither reabsorbed nor secreted by the kidneys according to standard technique.

The term "Michael acceptor" takes its normal meaning in the art. In certain embodiments the term "Michael acceptor" refers to activated olefins, such as α,β-unsaturated carbonyl compounds. A Michael acceptor can be a conjugated system with an electron withdrawing group, such as cyano, keto or ester. A non-exhaustive list of examples of Michael acceptors includes: vinyl ketones, alkyl acrylates, acrylo nitrile, and fumarates.

The term "molecular weight per nitrogen" or "MW/N" represents the calculated molecular weight in the polymer per nitrogen atom. It represents the average molecular weight to present one amine function within the crosslinked polymer. It is calculated by dividing the mass of a polymer sample by the moles of nitrogen present in the sample. "MW/N" is the inverse of theoretical capacity, and the calculations are based upon the feed ratio, assuming full reaction of crosslinker and monomer. The lower the molecular weight per nitrogen the higher the theoretical capacity of the crosslinked polymer.

The term "nonabsorbable" as used herein takes its normal meaning in the art. Therefore, if something is nonabsorbable it is not absorbed during its passage through the human GI tract. This could be measured by any appropriate means. One option known to the skilled person would be to examine faeces to see if the nonabsorbable material is recovered after passing through the GI tract. As a practical matter, the amount of a nonabsorbable material recovered in this scenario will never be 100% of the material administered. For example, about 90-99% of the material might be recovered from the faeces. Another option known to the skilled person would be to look for the presence of the material in the lymph, blood, interstitial fluid, secretions from various organs (eg, pancreas, liver, gut, etc) or in the body of organs (eg, liver, kidney, lungs, etc) as oral administration of a nonabsorbable material would not result in an increase in the amount of that material in these matrices and tissues. Nonabsorbable compositions may be particulate compositions that are essentially insoluble in the human GI tract and have a particle size that is large enough to avoid passive or active absorption through the human GI tract. As an example, nonabsorbable compositions is meant to imply that the substance does not enter the lymph, blood, interstitial fluids or organs through the main entry points of the human GI tract, namely by paracellular entry between gut epithelial cells, by endocytic uptake through gut epithelial cells, or through entry via M cells comprising the gut epithelial antigen sampling and immune surveillance system (Jung, 2000), either through active or passive transport processes. There is a known size limit for a particulate to be absorbed in the human GI tract (Jung et al., European Journal of Pharmaceutics and Biopharmaceutics 50 (2000) 147-160; Jani et al., Internation Journal of Pharmaceutics, 84 (1992) 245-252; and Jani et al., J. Pharm. Pharmacol. 1989, 41:809-812), so the skilled person would know that materials that, when in the GI tract, have a size of at least 1 micrometers would be nonabsorbable.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes embodiments in which the heterocyclyl group is substituted with an alkyl group and embodiments in which the heterocyclyl group is not substituted with alkyl.

"Particle size" is measured by wet laser diffraction using Mie theory. Particles are dispersed in an appropriate solvent, such as water or methanol, and added to the sample chamber to achieve red channel obscuration of 10-20%. Sonication may be performed, and a dispersing agent, such as a surfactant (e.g. Tween-80), may be added in order to disrupt weak particle-particle interactions. The refractive index setting of the particles used for size distribution calculation is selected to minimize artifacts in the results and the R parameter value, determined by the laser diffraction software. The D(0.1), D(0.5), and D(0.9) values characterizing the particle size distribution by volume-basis are recorded.

"Pharmaceutically acceptable" as used in connection with a carrier, diluent or excipient means a carrier, diluent or an excipient, respectively, that is useful in preparing a pharmaceutical composition that is generally safe, non-toxic and neither biologically nor otherwise undesirable for veterinary use and/or human pharmaceutical use.

The term "post polymerization crosslinking" is a term that describes a reaction to an already formed bead or gel, where more crosslinking is introduced to the already formed bead or gel to create a bead or gel that has an increased amount of crosslinking.

The term "post polymerization modification" is a term that describes a modification to an already formed bead or gel, where a reaction or a treatment introduces an additional functionality. This functionality can be linked either covalently or non-covalently to the already formed bead.

The term "quaternized amine assay" ("QAA") describes a method to estimate the amount of quaternary amines present in a given crosslinked polymer sample. This assay measures chloride binding of a crosslinked polymer at a pH of 11.5. At this pH, primary, secondary and tertiary amines are not substantially protonated and do not substantially contribute to chloride binding. Therefore, any binding observed under these conditions can be attributed to the presence of permanently charged quaternary amines. The test solution used for QAA assay is 100 mM sodium chloride at a pH of 11.5. The concentration of chloride ions is similar to that in the SGF assay which is used to assess total binding capacity of crosslinked polymers. Quaternary amine content as a percentage of total amines present is calculated as follows:

$$\%\ \text{Quaternary amines} = \frac{\text{Chloride bound (mmol/g) in } QAA}{\text{Chloride bound (mmol/g) in } SGF} \times 100$$

To perform the QAA assay, the free-amine polymer being tested is prepared at a concentration of 2.5 mg/ml (e.g. 25 mg dry mas) in 10 mL of QAA buffer. The mixture is incubated at 37° C. for ~16 hours with agitation on a rotisserie mixer. After incubation and mixing, 600 microliters of supernatant is removed and filtered using a 800 microliter, 0.45 micrometer pore size, 96-well poly propylene filter plate. With the samples arrayed in the filter plate and the collection plate fitted on the bottom, the unit is centrifuged at 1000×g for 1 minute to filter the samples. After filtration into the collection plate, the respective filtrates are diluted appropriately before measuring for chloride content. The IC method (e.g. ICS-2100 Ion Chromatography, Thermo Fisher Scientific) used for the analysis of chloride content in the filtrates consists of a 15 mM KOH mobile phase, an injection volume of 5 microliters, with a run time of three minutes, a washing/rinse volume of 1000 microliters, and flow rate of 1.25 mL/min. To determine the chloride bound to the polymer, the following calculation is completed:

$$\text{Binding capacity expressed as mmol chloride/g dry polymer} = \frac{(\text{Cl start} - \text{Cl } eq)}{2.5}$$

where Cl start corresponds to the starting concentration of chloride in the QAA buffer, Cl eq corresponds to the equilibrium value of chloride in the measured filtrates after exposure to the test polymer, and 2.5 is the polymer concentration in mg/ml.

The terms "short chain carboxylic acid" or "short chain fatty acid" take their normal meaning in the art. In certain embodiments, the terms "short chain carboxylic acid" or "short chain fatty acid" refer to carboxylic acids having a chain length of 0, 1, 2, 3, 4, 5 or 6 carbon atoms long. A non-exhaustive list of examples of short chain carboxylic acids includes: formic acid, acetic acid, propionic acid, butyric acid, isobutyric acid, valeric acid, isovaleric acid, and lactic acid.

"Simulated Gastric Fluid" or "SGF" Assay describes a test to determine total chloride binding capacity for a test polymer using a defined buffer that simulates the contents of gastric fluid as follows: Simulated gastric fluid (SGF) consists of 35 mM NaCl, 63 mM HCl, pH 1.2. To perform the assay, the free-amine polymer being tested is prepared at a concentration of 2.5 mg/ml (25 mg dry mass) in 10 mL of SGF buffer. The mixture is incubated at 37° C. overnight for ~12-16 hours with agitation on a rotisserie mixer. Unless another time period is otherwise stated, SGF binding data or binding capacities recited herein are determined in a time period of this duration. After incubation and mixing, the tubes containing the polymer are centrifuged for 2 minutes at 500-1000×g to pellet the test samples. Approximately 750 microliters of supernatant are removed and filtered using an appropriate filter, for example a 0.45 micrometer pore-size syringe filter or an 800 microliter, 1 micrometer pore-size, 96-well, glass filter plate that has been fitted over a 96-well 2 mL collection plate. With the latter arrangement, multiple samples tested in SGF buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL container. After filtration, the respective filtrates are diluted 4× with water and the chloride content of the filtrate is measured via ion chromatography (IC). The IC method (e.g. Dionex ICS-2100, Thermo Scientific) consists of an AS11 column and a 15 mM KOH mobile phase, an injection volume of 5 microliters, with a run time of 3 minutes, a washing/rinse volume of 1000 microliters, and flow rate of 1.25 mL/min. To determine the chloride bound to the polymer, the following calculation is completed:

$$\frac{(\text{Cl start} - \text{Cl } eq) \times 4}{2.5}.$$

Binding capacity expressed as mmol chloride/g polymer where Cl start corresponds to the starting concentration of chloride in the SGF buffer, Cl eq corresponds to the equilibrium value of chloride in the diluted measured filtrates after exposure to the test polymer, 4 is the dilution factor and 2.5 is the polymer concentration in mg/ml.

"Simulated Small Intestine Inorganic Buffer" or "SIB" is a test to determine the chloride and phosphate binding capacity of free amine test polymers in a selective specific interfering buffer assay (SIB). The chloride and phosphate binding capacity of free amine test polymers, along with the chloride and phosphate binding capacity of free amine sevelamer and bixalomer control polymers, was determined using the selective specific interfering buffer assay (SIB) as follows: The buffer used for the SIB assay comprises 36 mM NaCl, 20 mM $NaH_2PO_4$, 50 mM 2-(N-morpholino)ethanesulfonic acid (MES) buffered to pH 5.5. The SIB buffer contains concentrations of chloride, phosphate and pH that are present in the human duodenum and upper gastrointestinal tract (Stevens T, Conwell D L, Zuccaro G, Van Lente F, Khandwala F, Purich E, et al. Electrolyte composition of endoscopically collected duodenal drainage fluid after synthetic porcine secretin stimulation in healthy subjects. Gastrointestinal endoscopy. 2004; 60(3):351-5, Fordtran J, Locklear T. Ionic constituents and osmolality of gastric and small-intestinal fluids after eating. Digest Dis Sci. 1966; 11(7):503-21) and is an effective measure of the selectivity of chloride binding compared to phosphate binding by a polymer. To perform the assay, the free amine polymer being tested is prepared at a concentration of 2.5 mg/ml (25 mg dry mass) in 10 mL of SIB buffer. The mixture is incubated at 37° C. for 1 hour with agitation on a rotisserie mixer. Unless another time period is otherwise stated, SIB binding data or binding capacities recited herein are determined in a time period of this duration. After incubation and mixing, the tubes containing the polymer are centrifuged for 2 minutes at 1000×g to pellet the test samples. 750 microliter of supernatant is removed and filtered using an 800 microliter, 1 micrometer pore-size, 96-well, glass filter plate that has been fitted over a 96-well 2 mL collection plate; with this arrangement multiple samples tested in SIB buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter (0.45 micrometer) may be used in lieu of the filter plate, to retrieve ~2-4 mL of filtrate into a 15 mL vial. After filtration into the collection plate, the respective filtrates are diluted before measuring for chloride or phosphate content. For the measurement of chloride and phosphate, the filtrates under analysis are diluted 4× with water. The chloride and phosphate content of the filtrate is measured via ion chromatography (IC). The IC method (e.g. Dionex ICS-2100, Thermo Scientific) consists of an AS24A column, a 45 mM KOH mobile phase, an injection volume of 5 microliters, with a run time of about 10 minutes, a washing/rinse volume of 1000 microliter, and flow rate of 0.3 mL/min. To determine the chloride bound to the polymer, the following calculation is completed:

$$\text{Binding capacity expressed as mmol chloride/g dry polymer} = \frac{(Cl_{start} - Cl_{final}) \times 4}{2.5}$$

where $Cl_{start}$ corresponds to the starting concentration of chloride in the SIB buffer, $Cl_{final}$ corresponds to the final value of chloride in the measured diluted filtrates after exposure to the test polymer, 4 is the dilution factor and 2.5 is the polymer concentration in mg/ml. To determine the phosphate bound to the polymer, the following calculation is completed:

$$\text{Binding capacity expressed as mmol phosphate/g polymer} = \frac{(P_{start} - P_{final}) \times 4}{2.5}$$

where $P_{start}$ corresponds to the starting concentration of phosphate in the SIB buffer, $P_{final}$ corresponds to the final value of phosphate in the measured diluted filtrates after exposure to the test polymer, 4 is the dilution factor and 2.5 is the polymer concentration in mg/ml.

In certain embodiments, the term "statistically significant" refers to the likelihood that a relationship between two or more variables is caused by something other than random chance. More precisely, the significance level, α, defined for a study is the probability of the study rejecting the null hypothesis, given that it were true, and the p-value, p, of a result is the probability of obtaining a result at least as extreme, given that the null hypothesis were true. The result is statistically significant, by the standards of the study, when $p<\alpha$. The significance level for a study is chosen before data collection, and typically set to 5%

The term "substituted hydrocarbyl," "substituted alkyl," "substituted alkenyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

"Swelling Ratio" or simply "Swelling" describes the amount of water absorbed by a given amount of polymer divided by the weight of the polymer aliquot. The Swelling Ratio is expressed as: swelling=(g swollen polymer−g dry polymer)/g dry polymer. The method used to determine the Swelling Ratio for any given polymer comprised the following:

a. 50-100 mg of dry (less than 5 wt % water content) polymer is placed into an 11 mL sealable test tube (with screw cap) of known weight (weight of tube=Weight A).
b. Deionized water (10 mL) is added to the tube containing the polymer. The tube is sealed and tumbled for 16 hours (overnight) at room temperature. After incubation, the tube is centrifuged at 3000×g for 3 minutes and the supernatant is carefully removed by vacuum suction. For polymers that form a very loose sediment, another step of centrifugation is performed.
c. After step (b), the weight of swollen polymer plus tube (Weight B) is recorded.
d. Freeze at −40° C. for 30 minutes. Lyophilize for 48 h. Weigh dried polymer and test tube (recorded as Weight C).
e. Calculate g water absorbed per g of polymer, defined as: [(Weight B−Weight A)−(Weight C−Weight A)]/(Weight C−Weight A).

A "target ion" is an ion to which the polymer binds, and usually refers to the major ions bound by the polymer, or the ions whose binding to the polymer is thought to produce the therapeutic effect of the polymer (e.g., proton and chloride binding which leads to net removal of HCl).

The term "theoretical capacity" represents the calculated, expected binding of hydrochloric acid in an "SGF" assay, expressed in mmol/g. The theoretical capacity is based on the assumption that 100% of the amines from the monomer(s) and crosslinker(s) are incorporated in the crosslinked polymer based on their respective feed ratios. Theoretical capacity is thus equal to the concentration of amine functionalities in the polymer (mmol/g). The theoretical capacity assumes that each amine is available to bind the respective anions and cations and is not adjusted for the type of amine formed (e.g. it does not subtract capacity of quaternary amines that are not available to bind proton).

"Therapeutically effective amount" means the amount of a proton-binding crosslinked polymer that, when administered to a patient for treating a disease, is sufficient to effect such treatment for the disease. The amount constituting a "therapeutically effective amount" will vary depending on the polymer, the severity of the disease and the age, weight, etc., of the mammal to be treated.

"Treating" or "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis.

The term "triallylamine" denotes an amino moiety having three allyl groups.

The term "vinyl" denotes a moiety having the structural formula $R_xH_yC{=}CH{-}*$, where * denotes the point of attachment of the moiety to the remainder of the molecule wherein the point of attachment is a heteroatom or aryl, X and Y are independently 0, 1 or 2, such that X+Y=2, and R is hydrocarbyl or substituted hydrocarbyl.

The term "weight percent crosslinker" represents the calculated percentage, by mass, of a polymer sample that is derived from the crosslinker. Weight percent crosslinker is calculated using the feed ratio of the polymerization, and assumes full conversion of the monomer and crosslinker(s). The mass attributed to the crosslinker is equal to the expected increase of molecular weight in the infinite polymer network after reaction (e.g., 1,3-dichloropropane is 113 amu, but only 42 amu are added to a polymer network after crosslinking with DCP because the chlorine atoms, as leaving groups, are not incorporated into the polymer network).

When introducing elements of the present invention or the preferred embodiments(s) thereof, the articles “a”, “an”, “the” and “said” are intended to mean that there are one or more of the elements. The terms “comprising”, “including” and “having” are intended to be inclusive and not exclusive (i.e., there may be other elements in addition to the recited elements).

EMBODIMENTS

In accordance with the present disclosure, acid-base disorders may be treated using pharmaceutical compositions comprising a nonabsorbable composition having the capacity to remove clinically significant quantities of protons, the conjugate base of one or more strong acids, and/or one or more strong acids. An individual afflicted with a an acute or chronic acid/base disorder characterized by a baseline serum bicarbonate value of less than 22 mEq/o may thus be treated by oral administration of a pharmaceutical composition comprising the nonabsorbable composition which then transits the individual’s digestive system, binds a target species (protons, one or more conjugate base(s) of a strong acid and/or one or more strong acid(s)) as it transits the digestive system, and removes the bound target species by normal biological function (defecation).

In general, the individual afflicted with an acute or chronic acid/base disorder may be at any stage of chronic kidney disease. For example, in one embodiment the afflicted individual has not yet reached end stage renal disease (“ESRD”) sometimes also referred to as end stage chronic kidney disease and is not yet on dialysis (i.e., the individual has a mGFR (or eGFR) of at least 15 mL/min/1.73 $m^2$). In some embodiments, the afflicted individual will be Stage 3B CKD (i.e., the individual has a mGFR (or eGFR) in the range of 30-44 mL/min/1.73 $m^2$ for at least three months). In some embodiments, the afflicted individual will be Stage 3A CKD (i.e., the individual has a mGFR (or eGFR) in the range of 45-59 mL/min/1.73 $m^2$ for at least three months). Thus, for example, in some embodiments the afflicted individual has a mGFR or an eGFR of less than 60 mL/min/1.73 $m^2$ for at least three months. By way of further example, in some embodiments the afflicted individual has a mGFR or an eGFR of less than 45 mL/min/1.73 $m^2$ for at least three months. By way of further example, in some embodiments the afflicted individual has a mGFR or an eGFR of less than 30 mL/min/1.73 $m^2$ for at least three months. By way of further example, in some embodiments the afflicted individual has a mGFR or an eGFR of 15-30, 15-45, 15-60, 30-45 or even 30-60 mL/min/1.73 $m^2$ for at least three months.

The baseline serum bicarbonate value may be the serum bicarbonate concentration determined at a single time point or may be the mean or median value of two or more serum bicarbonate concentrations determined at two or more timepoints. For example, in one embodiment the baseline serum bicarbonate value may be the value of the serum bicarbonate concentration determined at a single time point and the baseline serum bicarbonate value is used as a basis to determine an acute acidic condition requiring immediate treatment. In another embodiment, the baseline serum bicarbonate treatment value is the mean value of the serum bicarbonate concentration for serum samples drawn at different time points (e.g., different days). By way of further example, in one such embodiment the baseline serum bicarbonate treatment value is the mean value of the serum bicarbonate concentration for serum samples drawn on different days (e.g., at least 2, 3, 4, 5 or more days, that may be consecutive or separated by one or more days or even weeks). By way of further example, in one such embodiment the baseline serum bicarbonate treatment value is the mean value of the serum bicarbonate concentration for serum samples drawn on two consecutive days preceding the initiation of treatment.

In one embodiment, the acid-base disorder being treated is characterized by a baseline serum bicarbonate value of less than 21 mEq/l. For example, in one such embodiment the acid-base disorder being treated is characterized by a baseline serum bicarbonate value of less than 20 mEq/l, 19 mEq/l, 18 mEq/l, 17 mEq/l, 16 mEq/l, 15 mEq/l, 14 mEq/l, 13 mEq/l, 12 mEq/l, 11 mEq/l, 10 mEq/l, or even less than 9 mEq/l.

In general, however, the acid-base disorder being treated is characterized by a baseline serum bicarbonate value of at least 9 mEq/l. For example, in one such embodiment the acid-base disorder being treated is characterized by a baseline serum bicarbonate value of at least 10 mEq/l, 11 mEq/l, 12 mEq/l, 13 mEq/l, 14 mEq/l, 15 mEq/l, 16 mEq/l, 17 mEq/l, 18 mEq/l, 19 mEq/l, 20 mEq/l, or even at least 21 mEq/l.

In certain embodiments, the acid-base disorder being treated is characterized by a baseline serum bicarbonate value in the range of 9 to 21 mEq/l. For example, in one such embodiment the acid-base disorder is characterized by a baseline serum bicarbonate value in the range of 12 to 20 mEq/l, 12 to 19 mEq/l, 12 to 18 mEq/l, 12 to 17 mEq/l, 12 to 16 mEq/l, 12 to 15 mEq/l. By way of further example, in one such embodiment the acid-base disorder is characterized by a baseline serum bicarbonate value in the range of 9 to 11 mEq/l, 12-14 mEq/l, 15-17 mEq/l, or even 18-21 mEq/l.

In certain embodiments, oral administration of a pharmaceutical composition containing a nonabsorbable composition increases the individual’s serum bicarbonate value from baseline to an increased serum bicarbonate value that exceeds the baseline serum bicarbonate value by at least 1 mEq/l, 1.5 mEq/l, 2 mEq/l, 2.5 mEq/l, 3 mEq/l, 3.5 mEq/l, 4 mEq/l, 5 mEq/l, 6 mEq/l, 7 mEq/l, 8 mEq/l, or even 9 mEq/l provided, however, the increased serum bicarbonate value does not exceed 29 mEq/l. In each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual’s serum bicarbonate value from a baseline serum bicarbonate value in the range of 12 to 20 mEq/l by at least 1 mEq/l. For example, in one such embodiment the treatment increases the individual’s serum bicarbonate value from a baseline serum bicarbonate value in the range of 12 to 20 mEq/l by at least 1.5 mEq/l, 2 mEq/l, 2.5 mEq/l, 3 mEq/l, 3.5 mEq/l, 4 mEq/l, 4.5 mEq/l, 5 mEq/l, 5.5 mEq/l, or even 6 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual’s serum bicarbonate value from a baseline serum bicarbonate value in the range of 9 to 21 mEq/l by at least 1 mEq/l. For example, in one such embodiment the treatment increases the individual's serum bicarbonate value from a baseline serum bicarbonate value in the range of 9 to 21 mEq/l by at least 1.5 mEq/l, 2 mEq/l, 2.5 mEq/l, 3 mEq/l, 3.5 mEq/l, 4 mEq/l, 4.5 mEq/l, 5 mEq/l, 5.5 mEq/l, or even 6 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 12 to 14 mEq/l by at least 1 mEq/l. For example, in one such embodiment the treatment increases the individual's serum bicarbonate value from a baseline serum bicarbonate value in the range of 12 to 14 mEq/l by at least 1.5 mEq/l, 2 mEq/l, 2.5 mEq/l, 3 mEq/l, 3.5 mEq/l, 4 mEq/l, 4.5 mEq/l, 5 mEq/l, 5.5 mEq/l, 6 mEq/l, 6.5 mEq/l, 7 mEq/l, 7.5 mEq/l, 8 mEq/l, 8.5 mEq/l, or even 9 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 15 to 17 mEq/l by at least 1 mEq/l. For example, in one such embodiment the treatment increases the individual's serum bicarbonate value from a baseline serum bicarbonate value in the range of 15 to 17 mEq/l by at least 1.5 mEq/l, 2 mEq/l, 2.5 mEq/l, 3 mEq/l, 3.5 mEq/l, 4 mEq/l, 4.5 mEq/l, 5 mEq/l, 5.5 mEq/l, 6 mEq/l, 6.5 mEq/l, 7 mEq/l, 7.5 mEq/l, 8 mEq/l, 8.5 mEq/l, or even 9 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 18 to 21 mEq/l by at least 1 mEq/l. For example, in one such embodiment the treatment increases the individual's serum bicarbonate value from a baseline serum bicarbonate value in the range of 18 to 21 mEq/l by at least 1.5 mEq/l, 2 mEq/l, 2.5 mEq/l, 3 mEq/l, 3.5 mEq/l, 4 mEq/l, 4.5 mEq/l, 5 mEq/l, 5.5 mEq/l, 6 mEq/l, 6.5 mEq/l, 7 mEq/l, 7.5 mEq/l, 8 mEq/l, 8.5 mEq/l, or even 9 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the treatment achieves a clinically significant increase is achieved within a treatment period of less than one month. For example, in one such embodiment, the treatment achieves a clinically significant increase within a treatment period of 25 days. By way of further example, in one such embodiment the treatment achieves the clinically significant increase is achieved within a treatment period of 3 weeks, 15 days, 2 weeks, 10 days, 1 week, 6 days, 5 days, 4 days, 3 days, 2 days, 1 day, or even within a treatment period of 12 hours.

In certain embodiments, the treatment achieves a clinically significant increase is achieved without any change in the individual's diet or dietary habits relative to the period immediately preceding the initiation of treatment. For example, in one such embodiment the clinically significant increase is achieved independent of the individual's diet or dietary habits.

In certain embodiments, the individual's serum bicarbonate value returns to the baseline value ±2.5 mEq/l, ±2 mEq/l, ±1.5 mEq/l, or even ±1 mEq/l within 1 month of the cessation of treatment. For example, in one such embodiment the individual's serum bicarbonate value returns to the baseline value ±2.5 mEq/l, ±2 mEq/l, ±1.5 mEq/l, or even ±1 mEq/l within 3 weeks of the cessation of treatment. By way of further example, in one such embodiment the individual's serum bicarbonate value returns to the baseline value ±2.5 mEq/l, ±2 mEq/l, ±1.5 mEq/l, or even ±1 mEq/l within 2 weeks of the cessation of treatment. By way of further example, in one such embodiment the individual's serum bicarbonate value returns to the baseline value ±2.5 mEq/l, ±2 mEq/l, ±1.5 mEq/l, or even ±1 mEq/l within 10 days of the cessation of treatment. By way of further example, in one such embodiment the individual's serum bicarbonate value returns to the baseline value ±2.5 mEq/l, ±2 mEq/l, ±1.5 mEq/l, or even ±1 mEq/l within 7 days of the cessation of treatment.

In one embodiment, the baseline serum bicarbonate value is the value of the serum bicarbonate concentration determined at a single time point. In another embodiment, the baseline serum bicarbonate value is the mean value of at least two serum bicarbonate concentrations determined at different time-points. For example, in one such embodiment the baseline serum bicarbonate value is the mean value of at least two serum bicarbonate concentrations for serum samples drawn on different days. By way of further example, the baseline serum bicarbonate value is the mean or median value of at least two serum bicarbonate concentrations for serum samples drawn on non-consecutive days. By way of further example, in one such method the non-consecutive days are separated by at least two days. By way of further example, in one such method the non-consecutive days are separated by at least one week. By way of further example, in one such method the non-consecutive days are separated by at least two weeks. By way of further example, in one such method the non-consecutive days are separated by at least three weeks.

In certain embodiments, the daily dose is no more than 100 g/day of the composition. For example, in one such embodiment the daily dose is no more than 90 g/day of the nonabsorbable composition. By way of further example, in one such embodiment the daily dose is no more than 75 g/day, 65 g/day, 50 g/day, 40 g/day, 30 g/day, 25 g/day, 20 g/day, 15 g/day, 10 g/day, or even no more than 5 g/day of the composition.

In certain embodiments, the individual is treated with the daily dose for a period of at least one day. For example, in one such embodiment the individual is treated with the daily dose for a period of at least one week, one month, two months, three months, six months, or even a period of at least one year.

In certain embodiments of the method of the present disclosure, the daily dose of the nonabsorbable composition has the capacity to remove at least about 5 mEq/day of the target species. For example, in one such embodiment the daily dose of the nonabsorbable composition has the capacity to remove at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or even at least about 50 mEq/day of the target species.

In certain embodiments of the method of the present disclosure, the daily dose of the nonabsorbable composition removes less than 60 mEq/day, 55 mEq/day, 50 mEq/day, 45 mEq/day, 40 mEq/day, 35 mEq/day, 30 mEq/day, 25 mEq/day, 20 mEq/day, 15 mEq/day, or even less than 10 mEq/day of the target species.

While the methods described above refer to daily dose, a further aspect of the disclosure include the methods disclosed herein in which the dose is administered less frequently than once per day (while still being administered on a regular basis). In any of the disclosure, the daily dose specified may, instead, be administrated on a less frequent basis. For example, the doses disclosed here may be administered once every two or three days. Or the doses disclosed here may be administered once, twice or three times a week.

In addition to (or as a surrogate for) serum bicarbonate, other biomarkers of acid-base imbalance may be used as a measure of acid-base status. For example, blood (serum or plasma) pH, total $CO_2$, anion gap, and/or the concentration of other electrolytes (e.g., sodium, potassium, calcium, magnesium, chloride and/or sulfate) may be used as an indicator of acid-base imbalance. Similarly, net acid excretion ("NAE"), urine pH, urine ammonium concentration, and/or the concentration of other electrolytes in the urine (e.g., sodium, potassium, calcium, magnesium, chloride and/or sulfate) may be used as an indicator of acid-base imbalance.

| Fluid | Biomarker of interest | Normal/Target Value | Analytical Technique |
|---|---|---|---|
| Blood (serum or | Total $CO_2$ | 23-29 mmol/L | Blood gas analyzer; enzymatic assay; ion selective electrode |
| plasma) | Anion gap | 3-11 mEq/L | Obtained from standard chemistry electrolyte panel |
| | pH | 7.36 to 7.44 | Blood gas analyzer; enzymatic assay; ion selective electrode |
| | Electrolytes | Na = 135-145 mEq/L; K = 3.5-5 mEq/L; Total Ca = 8-10.5 mEq/L, depending on age and sex; Mg = 1.5-2.5 mEq/L, depending on age; Cl = 95-105 mEq/L; phosphate = 2.5-4.5 mEq/L; sulfate = 1 mEq/L | Obtained from standard chemistry electrolyte panel; ion selective electrodes can be used for Na, Cl and K |
| urine | pH | 4.5-8.0 | pH meter |
| | ammonium | 3-65 mmol/L | Enzymatic |
| | citrate | 150-1,191 mg/24-hour urine collection; ranges for 20 to 60 years of age | Enzymatic |
| | sodium | 20 mEq/L in spot samples, 41-227 mEq/L per day (depending upon salt and fluid intake) | Ion-selective electrode |
| | potassium | 17-77 mmol/24 hours; spot sample is ~45 mmol/L | Ion-selective electrode |
| | calcium | Urinary calcium is <250 mg/24 hours in males, <200 mg/24 hours in females | Enzymatic |
| | magnesium | Urinary magnesium is 51-269 mg/24 hours; spot values are usually reported as a ratio with creatinine and are >0.035 mg Mg/mg creatinine | Enzymatic |
| | chloride | Urinary chloride is 40-224 mmol/24 hours | Ion-selective electrode |
| | Urine Anion Gap ("UAG") | UAG = 0-10 mEq/L; Metabolic acidosis indicated when UAG >20 mEq/L | UAG = $(Na^+ + K^+) - Cl^-$ in urine. It is a measure of ammonium excretion, the primary mechanism for acid excretion. |

-continued

| Fluid | Biomarker of interest | Normal/Target Value | Analytical Technique |
|---|---|---|---|
| | Net Acid Excretion | Urinary net acid excretion is the total amount of acid excreted by the kidney per day; the NAE value depends on the age of the subject, gender, and protein intake; typical NAE values range from 9 mEq/day to 38 mEq/day | 24-hour urine collection required; Direct NAE measurement (mEq/day) = $[NH_4^+]$ + [TA] − $[HCO_3^-]$, where TA is concentration of titratable acids Indirect NAE measurement (mEq/day) = (Cl + P + $SO_4$ + organic anions) − (Na + K + Ca + Mg). |

Figure 13A:
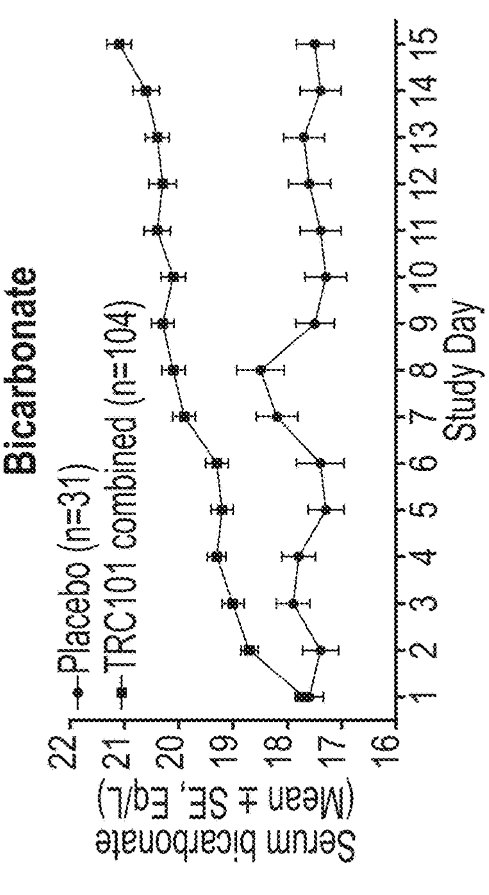
Figure 13B:
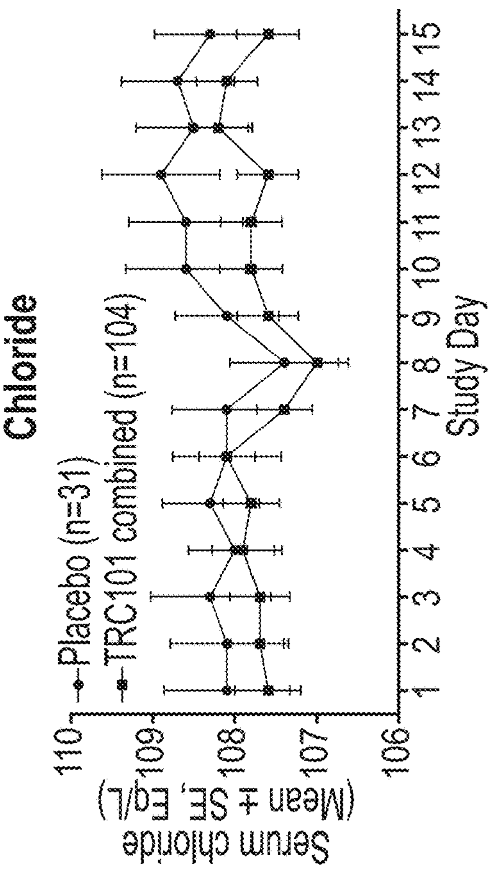
Figure 13C:
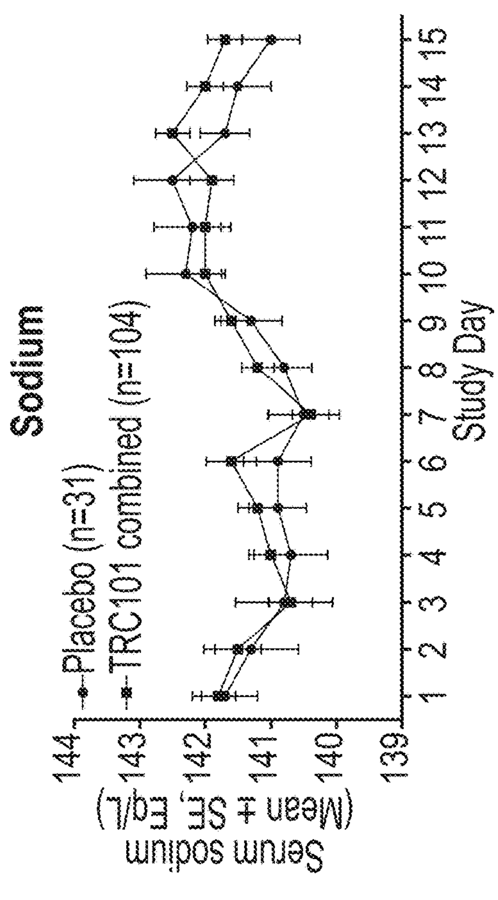
Figure 13D:
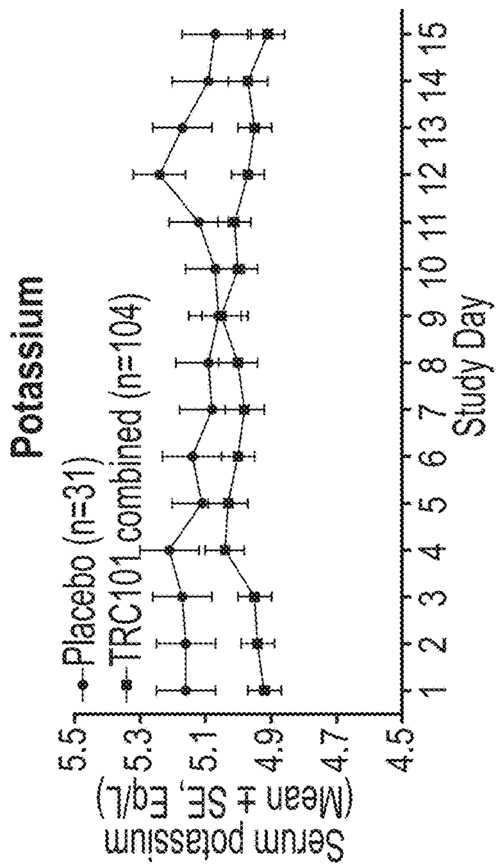

In one embodiment, treatment of an individual as described herein may improve an individuals' serum anion gap. For example, treating an acid base imbalance with a neutral composition having the capacity to bind both protons and anions (unaccompanied by the delivery of sodium or potassium ions) can increase serum bicarbonate without an accompanying increase in sodium or potassium (see Example 3 and FIGS. 13A, 13C and 13D). Consequently, the serum anion gap may be improved (decreased) by at least 1 mEq/l or more (e.g., at least 2 mEq/O) within a period as short as 2 weeks (see Example 3).

The various aspects and embodiments may have a range of advantages, such as improved or successful treatment of metabolic acidosis. Such improvements may also include reduced side effects, increased patient compliance, reduced drug loads, increased speed of treatment, increased magnitude of treatment, avoiding unwanted changes to other electrolytes and/or reduced drug-drug interactions. A further improvement may include reducing a patient's anion gap (as defined above) as part of the methods and other aspects disclosed herein. Further useful features of the disclosed aspects can be found in the examples.

Certain Specific Compositions for Use in Treatment

As previously noted, one aspect disclosed here is a composition for use in a method of treating metabolic acidosis in an adult human patient wherein said composition comprises a polymer having the capacity to remove HCl from the patient, wherein the polymer is characterized by a chloride ion binding capacity of at least 2.5 mEq/g in a Simulated Small Intestine Inorganic ("SIB") assay. This aspect is based on the data in the examples showing the absorption and removal of HCl to successfully treat patients, allowing the amount of the composition to be set based on its capacity to bind chloride in the SIB assay. As shown in the examples, a composition with this specified level of chloride binding in the "SIB" assay can be used in the specified dose range to successfully treat metabolic acidosis in adult humans. In this aspect, the composition may be administered orally, and so would be an orally administered nonabsorbable composition as defined herein.

This aspect is based on the data in the examples showing the absorption and removal of HCl to successfully treat patients using a composition according to this aspect, allowing the amount of the composition to be set based on its capacity to bind chloride in the SIB assay. Surprisingly, the amounts required for successful treatment were relatively low.

Another aspect of the present disclosure is a composition for use in a method of treating metabolic acidosis in an adult human patient by increasing that patient's serum bicarbonate value by at least 1 mEq/L over 15 days of treatment, said composition being a nonabsorbable composition having the capacity to remove protons from the patient. In this aspect, the composition may be administered orally, and so would be an orally administered nonabsorbable composition as defined herein.

This aspect is based on the data in the examples showing the absorption and removal of HCl to successfully treat patients using a composition according to this aspect which provides new detail regarding the reductions possible using a composition of the disclosure. This aspect includes surprisingly rapid increases in the patient's serum bicarbonate level, for example in the first few days, as well as surprisingly large increases in serum bicarbonate level.

Another aspect of the present disclosure is a composition for use in a method of treating metabolic acidosis in an adult human patient, said patient having a serum bicarbonate level of less than 20 mEq/L prior to treatment, said composition being a nonabsorbable composition having the capacity to remove protons from the patient. In this aspect, the composition may be administered orally, and so would be an orally administered nonabsorbable composition as defined herein.

This aspect is based on the data in the examples showing, for the first time, the successful treatment of patients with a low serum bicarbonate level, for example levels that have not been shown to be so readily treated previously. The patients with lower serum bicarbonate levels responded particularly well to the treatment and this improvement for this subgroup is one advantage of this aspect.

The chloride ion binding capacity in the SIB assay is affected by both the composition's selectivity for binding chloride and the total space available for chloride binding. The term "composition" refers to the active pharmaceutical ingredient, including any counter ions, but not to excipients. So, the "amount" of the composition is the amount of active pharmaceutical ingredient without including other parts of any unit dose form.

More specifically in these aspects, the amount of composition may be any amount disclosed herein in other sections within the range 0.1 g-12 g. For example, 1-11 g, 2-10 g, 3-9 g, 3-8 g, 3-7 g, 3-6 g, 3.5-5.5 g, 4-5 g, or 4.5-5 g of said polymer is administered to the patient per day, or 0.5 g, 1 g, 1.5 g, 2 g, 2.5 g, 3 g, 3.5 g, 4.0 g, 4.5 g or 5.0 g of the composition is administered to the patient per day.

More specifically in these aspects, the chloride ion binding capacity in a Simulated Small Intestine Inorganic Buffer ("SIB") assay may be greater than 3, 3.5, 4, or 4.5 mEq/g. One upper limit for the chloride ion binding capacity in a SIB assay is 10 mEq/g. Other the upper limits may be 5, 5.5, 6, 6.5, 7, 7.5, 8, 8.5, 9, 9.5 or 10 mEq/g, or there may be no upper limit specified.

All combinations of the amount of composition and the chloride ion binding capacity mentioned here are also disclosed. For example, in one embodiment, the composition has a chloride ion binding capacity in a SIB assay is of at least 4.5 mEq/g and only 0.1-6 gs of composition is administered in the method of treating metabolic acidosis.

The composition in these aspects can additionally have any of the properties or features specified elsewhere herein. For example, the composition may be a nonabsorbable composition as described in the following section. In a similar fashion, the methods of treatment specified in these aspects may include any of the features disclosed in the preceding section regarding certain methods of treatment.

Nonabsorbable Compositions

As previously noted, the pharmaceutical compositions having the medical uses described herein possess the capacity to remove clinically significant quantities of HCl. To bind such target species, the pharmaceutical compositions may be selected from the group consisting of cation exchange compositions, anion exchange compositions, amphoteric ion exchange compositions, neutral compositions having the capacity to bind both protons and anions, composites thereof and mixtures thereof.

In general, the pharmaceutical composition comprises a population of particles having a preferred particle size range that is (i) large enough to avoid passive or active absorption through the GI tract and (ii) small enough to not cause grittiness or unpleasant mouth feel when ingested as a powder, sachet and/or chewable tablet/dosage form with a mean particle size of at least 3 microns. For example, in one such embodiment the nonabsorbable composition comprises a population of particles having a mean particle size (volume distribution) in the range of 5 to 1,000 microns. By way of further example, in one such embodiment the nonabsorbable composition comprises a population of particles having a mean particle size (volume distribution) in the range of 5 to 500 microns. By way of further example, in one such embodiment the nonabsorbable composition comprises a population of particles having a mean particle size (volume distribution) in the range of 10 to 400 microns. By way of further example, in one such embodiment the nonabsorbable composition comprises a population of particles having a mean particle size (volume distribution) in the range of 10 to 300 microns. By way of further example, in one such embodiment the nonabsorbable composition comprises a population of particles having a mean particle size (volume distribution) in the range of 20 to 250 microns. By way of further example, in one such embodiment the nonabsorbable composition comprises a population of particles having a mean particle size (volume distribution) in the range of 30 to 250 microns. By way of further example, in one such embodiment the nonabsorbable composition comprises a population of particles having a mean particle size (volume distribution) in the range of 40 to 180 microns. In certain embodiments, less than 7% of the particles in the population (volume distribution) have a diameter less than 10 microns. For example, in such embodiments less than 5% of the particles in the particles in the population (volume distribution) have a diameter less than 10 microns. By way of further example, in such embodiments less than 2.5% of the particles in the particles in the population (volume distribution) have a diameter less than 10 microns. By way of further example, in such embodiments less than 1% of the particles in the particles in the population (volume distribution) have a diameter less than 10 microns. In all embodiments, the particle size may be measured using the protocol set out in the abbreviations and definitions section (above).

To minimize GI side effects in patients that are often related to a large volume polymer gel moving through the GI tract, a low Swelling Ratio of the nonabsorbable composition is preferred (0.5 to 10 times its own weight in water). For example, in one such embodiment the nonabsorbable composition has a Swelling Ratio of less than 9. By way of further example, in one such embodiment the nonabsorbable composition has a Swelling Ratio of less than 8. By way of further example, in one such embodiment the nonabsorbable composition has a Swelling Ratio of less than 7. By way of further example, in one such embodiment the nonabsorbable composition has a Swelling Ratio of less than 6. By way of further example, in one such embodiment the nonabsorbable composition has a Swelling Ratio of less than 5. By way of further example, in one such embodiment the nonabsorbable composition has a Swelling Ratio of less than 4. By way of further example, in one such embodiment the nonabsorbable composition has a Swelling Ratio of less than 3. By way of further example, in one such embodiment the nonabsorbable composition has a Swelling Ratio of less than 2.

The amount of the target species, HCl, that is bound as the nonabsorbable composition transits the GI tract is largely a function of the binding capacity of the composition for the target species and the quantity of the nonabsorbable composition administered per day as a daily dose. In general, the theoretical binding capacity for HCl may be determined using a SGF assay and determining the amount of a species that appeared in or disappeared from the SGF buffer during the SGF assay. For example, the theoretical proton binding capacity of a cation exchange resin may be determined by measuring the increase in the amount of cations (other than protons) in the buffer during a SGF assay. Similarly, the theoretical anion binding capacity of an anion exchange resin (in a form other than the chloride form) may be determined by measuring the increase in the amount of anions (other than chloride ions) in the buffer during a SGF assay. Additionally, the theoretical anion binding capacity of a neutral composition for protons and the conjugate base of a strong acid may be determined by measuring the decrease in chloride concentration in the buffer during a SGF assay.

In general, the nonabsorbable composition will have a theoretical binding capacity for the target species (HCl) of at least about 0.5 mEq/g (as determined in an SGF assay). For example, in some embodiments the nonabsorbable composition will have a theoretical binding capacity for the target species of at least about 1 mEq/g, 2 mEq/g, 3 mEq/g, 4 mEq/g, 5 mEq/g, 7.5 mEq/g, 10 mEq/g, 12.5 mEq/g, 15 mEq/g, 20 mEq/g, or even at least about 35 mEq/g. In certain embodiments, the theoretical binding capacity of the nonabsorbable compositions for the target species is not in excess of 30 mEq/g. Thus, for example, the theoretical binding capacity of the nonabsorbable compositions for the target species may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

In general, the nonabsorbable composition will have a theoretical binding capacity for protons of at least about 0.5 mEq/g (as determined in an SGF assay). For example, in some embodiments the nonabsorbable composition will have a theoretical binding capacity for protons of at least about 1 mEq/g, 2 mEq/g, 3 mEq/g, 4 mEq/g, 5 mEq/g, 7.5 mEq/g, 10 mEq/g, 12.5 mEq/g, 15 mEq/g, or even at least about 20 mEq/g. In general, the nonabsorbable composition will typically have a theoretical binding capacity for protons that is not in excess of about 35 mEq/g. For example, in some embodiments, the theoretical binding capacity of the nonabsorbable compositions for protons that is not in excess of 30 mEq/g. Thus, for example, the theoretical binding capacity of the nonabsorbable compositions for protons may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

Phosphate, bicarbonate, bicarbonate equivalents, the conjugate bases of bile and fatty acids are potential interfering anions for chloride or other conjugate bases of strong acids (e.g., $HSO_4^-$ and $SO_4^{2-}$) in the stomach and small intestine. Therefore, rapid and preferential binding of chloride over phosphate, bicarbonate equivalents, and the conjugate bases of bile and fatty acids in the small intestine is desirable and the SIB assay may be used to determine kinetics and preferential binding. Since the transit time of the colon is slow (2-3 days) relative to the small intestine, and since conditions in the colon will not be encountered by an orally administered nonabsorbable composition until after stomach and small intestine conditions have been encountered, kinetics of chloride binding by a nonabsorbable composition do not need to be as rapid in the colon or under in vitro conditions designed to mimic the late small intestine/colon. It is, however, desirable that chloride binding and selectivity over other interfering anions is high, for example, at 24 and/or 48 hours or longer.

In one embodiment, the nonabsorbable composition is characterized by a chloride ion binding capacity of at least 1 mEq/g in a Simulated Small Intestine Inorganic Buffer ("SIB") assay. For example, in one such embodiment the nonabsorbable composition is characterized by a chloride ion binding capacity of at least 1.5 mEq/g, 2 mEq/g, 2.5 mEq/g, 3 mEq/g, 3.5 mEq/g, 4 mEq/g, 4.5 mEq/g, 5 mEq/g, 5.5 mEq/g, or even at least about 6 mEq/g in a SIB assay.

In one embodiment, the nonabsorbable composition binds a significant amount of chloride relative to phosphate as exhibited, for example, in a SIB assay. For example, in one embodiment the ratio of the amount of bound chloride to bound phosphate in a SIB assay is at least 0.1:1, respectively. By way of further example, in one such embodiment the ratio of the amount of bound chloride to bound phosphate in a SIB assay is at least 0.2:1, 0.25:1, 0.3:1, 0.35:1, 0.4:1, 0.45:1, 0.5:1, 2:3, 0.75:1, 0.9:1, 1:1, 1.25:1, 1.5:1, 1.75:1, 2:1, 2.25:1, 2.5:1, 2.75:1, 3:1, 4:1, or even at least about 5:1, respectively.

In one embodiment, the orally administered nonabsorbable composition is characterized by a proton-binding capacity and a chloride binding capacity in Simulated Gastric Fluid of at least 1 mEq/g in a SGF assay. For example, in one such embodiment the nonabsorbable composition is characterized by a proton-binding capacity and a chloride binding capacity in a SGF assay of at least 2 mEq/g, 3 mEq/g, 4 mEq/g, 5 mEq/g, 6 mEq/g, 7 mEq/g, 8 mEq/g, 9 mEq/g, 10 mEq/g, 11 mEq/g, 12 mEq/g, 13 mEq/g, or even at least about 14 mEq/g. By way of further example, in one such embodiment the nonabsorbable composition is characterized by a proton-binding capacity and a chloride binding capacity after 1 hour in SGF that is at least 50% of the proton-binding capacity and the chloride binding capacity, respectively, of the nonabsorbable composition at 24 hours in SGF. By way of further example, in one such embodiment the nonabsorbable composition is characterized by a proton-binding capacity and a chloride binding capacity after 1 hour in SGF that is at least 60%, 70%, 80%, or even at least 90% of the proton-binding capacity and the chloride binding capacity, respectively, of the nonabsorbable composition at 24 hours in SGF.

In one embodiment, the nonabsorbable composition comprises a neutral composition having the capacity to bind both protons and anions. Exemplary neutral nonabsorbable compositions that bind both protons and anions include polymers functionalized with propylene oxide, polymers functionalized with Michael acceptors, expanded porphyrins, covalent organic frameworks, and polymers containing amine and/or phosphine functional groups.

In those embodiments in which the nonabsorbable composition binds chloride ions, it is generally preferred that the nonabsorbable composition selectively bind chloride ions relative to other counter ions such as bicarbonate equivalent anions, phosphate anions, and the conjugate bases of bile and fatty acids. Stated differently, it is generally preferred in these embodiments that the nonabsorbable composition (i) remove more chloride ions than bicarbonate equivalent anions (ii) remove more chloride ions than phosphate anions, and (iii) remove more chloride ions than the conjugate bases of bile and fatty acids. Advantageously, therefore, treatment with the nonabsorbable composition does not induce or exacerbate hypophosphatemia (i.e., a serum phosphorous concentration of less than about 2.4 mg/dL, does not significantly elevate low density lipoproteins ("LDL"), or otherwise negatively impact serum or colon levels of metabolically relevant anions.

In some embodiments, the pharmaceutical composition comprises a crosslinked polymer containing the residue of an amine corresponding to Formula 1:

Formula 1

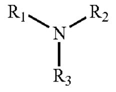

wherein $R_1$, $R_2$ and $R_3$ are independently hydrogen, hydrocarbyl, substituted hydrocarbyl provided, however, at least one of $R_1$, $R_2$ and $R_3$ is other than hydrogen. Stated differently, at least one of $R_1$, $R_2$ and $R_3$ is hydrocarbyl or substituted hydrocarbyl, and the others of $R_1$, $R_2$ and $R_3$ are independently hydrogen, hydrocarbyl, or substituted hydrocarbyl. In one embodiment, for example, $R_1$, $R_2$ and $R_3$ are independently hydrogen, aryl, aliphatic, heteroaryl, or heteroaliphatic provided, however, each of $R_1$, $R_2$ and $R_3$ are not hydrogen. By way of further example, in one such embodiment $R_1$, $R_2$ and $R_3$ are independently hydrogen, saturated hydrocarbons, unsaturated aliphatic, unsaturated heteroaliphatic, heteroalkyl, heterocyclic, aryl or heteroaryl, provided, however, each of $R_1$, $R_2$ and $R_3$ are not hydrogen. By way of further example, in one such embodiment $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ are not hydrogen. By way of further example, in one such embodiment $R_1$, $R_2$ and $R_3$ are independently hydrogen, alkyl, aminoalkyl, alkanol, aryl, haloalkyl, hydroxyalkyl, ethereal, heteroaryl or heterocyclic provided, however, each of $R_1$, $R_2$ and $R_3$ are not hydrogen. By way of further example, in one such embodiment $R_1$ and $R_2$ (in combination with the nitrogen atom to which they are attached) together constitute part of a ring structure, so that the monomer as described by Formula 1 is a nitrogen-containing heterocycle (e.g., piperidine) and $R_3$ is hydrogen, or heteroaliphatic. By way of further example, in one embodiment $R_1$, $R_2$ and $R_3$ are independently hydrogen, aliphatic or heteroaliphatic provided, however, at least one of $R_1$, $R_2$ and $R_3$ is other than hydrogen. By way of further example, in one embodiment $R_1$, $R_2$ and $R_3$ are independently hydrogen, allyl, or aminoalkyl.

In one embodiment, the crosslinked polymer comprises the residue of an amine corresponding to Formula 1 wherein $R_1$, $R_2$, and $R_3$ are independently hydrogen, heteroaryl, aryl, aliphatic or heteroaliphatic provided, however, at least one of $R_1$, $R_2$, and $R_3$ is aryl or heteroaryl. For example, in this embodiment $R_1$ and $R_2$, in combination with the nitrogen atom to which they are attached, may form a saturated or unsaturated nitrogen-containing heterocyclic ring. By way of further example, $R_1$ and $R_2$, in combination with the nitrogen atom to which they are attached may constitute part of a pyrrolidino, pyrrole, pyrazolidine, pyrazole, imidazolidine, imidazole, piperidine, pyridine, piperazine, diazine, or triazine ring structure. By way of further example, $R_1$ and $R_2$, in combination with the nitrogen atom to which they are attached may constitute part of a piperidine ring structure.

In one embodiment, the crosslinked polymer comprises the residue of an amine corresponding to Formula 1 wherein $R_1$, $R_2$, and $R_3$ are independently hydrogen, aliphatic, or heteroaliphatic provided, however, at least one of $R_1$, $R_2$, and $R_3$ is other than hydrogen. For example, in this embodiment $R_1$, $R_2$, and $R_3$ may independently be hydrogen, alkyl, alkenyl, allyl, vinyl, aminoalkyl, alkanol, haloalkyl, hydroxyalkyl, ethereal, or heterocyclic provided, however, at least one of $R_1$, $R_2$, and $R_3$ is other than hydrogen. By way of further example, in one such embodiment $R_1$ and $R_2$, in combination with the nitrogen atom to which they are attached, may form a saturated or unsaturated nitrogen-containing heterocyclic ring. By way of further example, in one such embodiment $R_1$ and $R_2$, in combination with the nitrogen atom to which they are attached may constitute part of a pyrrolidino, pyrrole, pyrazolidine, pyrazole, imidazolidine, imidazole, piperidine, piperazine, or diazine ring structure. By way of further example, in one such embodiment $R_1$ and $R_2$, in combination with the nitrogen atom to which they are attached may constitute part of a piperidine ring structure. By way of further example, in one such embodiment the amine corresponding to Formula 1 is acyclic and at least one of $R_1$, $R_2$, and $R_3$ is aliphatic or heteroaliphatic. By way of further example, in one such embodiment $R_1$, $R_2$, and $R_3$ are independently hydrogen, alkyl, allyl, vinyl, alicyclic, aminoalkyl, alkanol, or heterocyclic, provided at least one of $R_1$, $R_2$, and $R_3$ is other than hydrogen.

In one embodiment, the crosslinked polymer comprises the residue of an amine corresponding to Formula 1 and the crosslinked polymer is prepared by substitution polymerization of the amine corresponding to Formula 1 with a polyfunctional crosslinker (optionally also comprising amine moieties) wherein $R_1$, $R_2$, and $R_3$ are independently hydrogen, alkyl, aminoalkyl, or alkanol, provided at least one of $R_1$, $R_2$, and $R_3$ is other than hydrogen.

In some embodiments, the molecular weight per nitrogen of the polymers of the present disclosure may range from about 40 to about 1000 Daltons. In one embodiment, the molecular weight per nitrogen of the polymer is from about 40 to about 500 Daltons. In another embodiment, the molecular weight per nitrogen of the polymer is from about 50 to about 170 Daltons. In another embodiment, the molecular weight per nitrogen of the polymer is from about 60 to about 110 Daltons.

In some embodiments, an amine-containing monomer is polymerized and the polymer is concurrently crosslinked in a substitution polymerization reaction in the first reaction step. The amine reactant (monomer) in the concurrent polymerization and crosslinking reaction can react more than one time for the substitution polymerization. In one such embodiment, the amine monomer is a linear amine possessing at least two reactive amine moieties to participate in the substitution polymerization reaction. In another embodiment, the amine monomer is a branched amine possessing at least two reactive amine moieties to participate in the substitution polymerization reaction. Crosslinkers for the concurrent substitution polymerization and crosslinking typically have at least two amine-reactive moieties such as alkyl-chlorides, and alkyl-epoxides. In order to be incorporated into the polymer, primary amines react at least once and potentially may react up to three times with the crosslinker, secondary amines can react up to twice with the crosslinkers, and tertiary amines can only react once with the crosslinker. In general, however, the formation of a significant number of quaternary nitrogens/amines is generally not preferred because quaternary amines cannot bind protons.

Exemplary amines that may be used in substitution polymerization reactions described herein include 1,3-Bis[bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino]ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl)ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, 3-(Methylamino)pyrrolidine Exemplary crosslinking agents that may be used in substitution polymerization reactions and post-polymerization crosslinking reactions include, but are not limited to, one or more multifunctional crosslinking agents such as: dihaloalkanes, haloalkyloxiranes, alkyloxirane sulfonates, di(haloalkyl)amines, tri(haloalkyl) amines, diepoxides, triepoxides, tetraepoxides, bis(halomethyl)benzenes, tri(halomethyl)

benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl) amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol diglycidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl) tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1,3,5,7,9,11,14-heptacyclopentyltricyclo [7,3,3,15, 11]heptasiloxane, 4,4'methylenebis(N,N-diglycidylaniline), bis(halomethyl) benzene, bis(halomethyl)biphenyl and bis(halomethyl) naphthalene, toluene diisocyanate, acryloyl chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino) ethane, Bis(3-chloropropyl)amine, 1,3-Dichloro-2-propanol, 1,3-Dichloropropane, 1-chloro-2,3-epoxypropane, tris [(2-oxiranyl)methyl]amine.

In some embodiments, the carbon to nitrogen ratio of the polymers of the present disclosure may range from about 2:1 to about 6:1, respectively. For example, in one such embodiment, the carbon to nitrogen ratio of the polymers of the present disclosure may range from about 2.5:1 to about 5:1, respectively. By way of further example, in one such embodiment, the carbon to nitrogen ratio of the polymers of the present disclosure may range from about 3:1 to about 4.5:1, respectively. By way of further example, in one such embodiment, the carbon to nitrogen ratio of the polymers of the present disclosure may range from about 3.25:1 to about 4.25:1, respectively. By way of further example, in one such embodiment, the carbon to nitrogen ratio of the polymers of the present disclosure may range from about 3.4:1 to about 4:1, respectively. In another embodiment, the molecular weight per nitrogen of the polymer is from about 60 to about 110 Daltons.

In some embodiments, the crosslinked polymer comprises the residue of an amine corresponding to Formula 1a and the crosslinked polymer is prepared by radical polymerization of an amine corresponding to Formula 1a:

Formula 1a

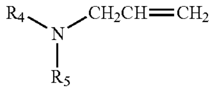

wherein $R_4$ and $R_5$ are independently hydrogen, hydrocarbyl, or substituted hydrocarbyl. In one embodiment, for example, $R_4$ and $R_5$ are independently hydrogen, saturated hydrocarbon, unsaturated aliphatic, aryl, heteroaryl, unsaturated heteroaliphatic, heterocyclic, or heteroalkyl. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, allyl, aminoalkyl, alkanol, aryl, haloalkyl, hydroxyalkyl, ethereal, or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl.

In some embodiments, the crosslinked polymer comprises the residue of an amine corresponding to Formula 1b and the crosslinked polymer is prepared by substitution polymerization of the amine corresponding to Formula 1b with a polyfunctional crosslinker (optionally also comprising amine moieties):

Formula 1b

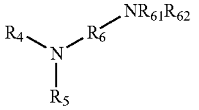

wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic. In one embodiment, for example, $R_4$ and $R_5$ are independently hydrogen, saturated hydrocarbon, unsaturated aliphatic, aryl, heteroaryl, heteroalkyl, or unsaturated heteroaliphatic. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, alkenyl, aminoalkyl, alkanol, aryl, haloalkyl, hydroxyalkyl, ethereal, heteroaryl or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl. By way of further example, in each of the embodiments recited in this paragraph, $R_6$ may be methylene, ethylene or propylene, and $R_{61}$ and $R_{62}$ may independently be hydrogen, allyl or aminoalkyl.

In some embodiments, the crosslinked polymer comprises the residue of an amine corresponding to Formula 1c:

Formula 1c

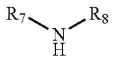

wherein $R_7$ is hydrogen, aliphatic or heteroaliphatic and $R_8$ is aliphatic or heteroaliphatic. For example, in one such embodiment, for example, $R_7$ is hydrogen and $R_8$ is aliphatic or heteroaliphatic. By way of further example, in one such embodiment $R_7$ and $R_8$ are independently aliphatic or heteroaliphatic. By way of further example, in one such embodiment at least one of $R_7$ and $R_8$ comprises an allyl moiety. By way of further example, in one such embodiment at least one of $R_7$ and $R_8$ comprises an aminoalkyl moiety. By way of further example, in one such embodiment $R_7$ and $R_8$ each comprise an allyl moiety. By way of further example, in one such embodiment $R_7$ and $R_8$ each comprise an aminoalkyl moiety. By way of further example, in one such embodiment $R_7$ comprises an allyl moiety and $R_8$ comprises an aminoalkyl moiety.

In some embodiments, the crosslinked polymer comprises the residue of an amine corresponding to Formula 2:

Formula 2

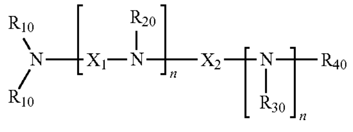

wherein m and n are independently non-negative integers;

$R_{10}$, $R_{20}$, $R_{30}$, and $R_{40}$ are independently hydrogen, hydrocarbyl, or substituted hydrocarbyl;

$X_1$ is

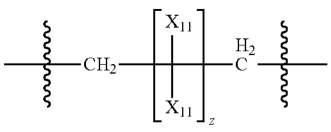 ;

$X_2$ is hydrocarbyl or substituted hydrocarbyl;

each $X_{11}$ is independently hydrogen, hydrocarbyl, substituted hydrocarbyl, hydroxyl, amino, boronic acid, or halo; and z is a non-negative number.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and $R_{10}$, $R_{20}$, $R_{30}$, and $R_{40}$ are independently hydrogen, aliphatic, aryl, heteroaliphatic, or heteroaryl. By way of further example, in one such embodiment $R_{10}$, $R_{20}$, $R_{30}$, and $R_{40}$ are independently hydrogen, aliphatic, or heteroaliphatic. By way of further example, in one such embodiment $R_{10}$, $R_{20}$, $R_{30}$, and $R_{40}$ are independently hydrogen, alkyl, allyl, vinyl, or aminoalkyl. By way of further example, in one such embodiment $R_{10}$, $R_{20}$, $R_{30}$, and $R_{40}$ are independently hydrogen, alkyl, allyl, vinyl, $-(CH_2)_dNH_2$, $-(CH_2)_dN[(CH_2)_eNH_2)]_2$ where d and e are independently 2-4. In each of the foregoing exemplary embodiments of this paragraph, m and z may independently be 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and $X_2$ is aliphatic or heteroaliphatic. For example, in one such embodiment $X_2$ is aliphatic or heteroaliphatic and $R_{10}$, $R_{20}$, $R_{30}$, and $R_{40}$ are independently hydrogen, aliphatic, heteroaliphatic. By way of further example, in one such embodiment $X_2$ is alkyl or aminoalkyl and $R_{10}$, $R_{20}$, $R_{30}$, and $R_{40}$ are independently hydrogen, aliphatic, or heteroaliphatic. By way of further example, in one such embodiment $X_2$ is alkyl or aminoalkyl and $R_{10}$, $R_{20}$, $R_{30}$, and $R_{40}$ are independently hydrogen, alkyl, allyl, vinyl, or aminoalkyl. In each of the foregoing exemplary embodiments of this paragraph, m and z may independently be 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m is a positive integer. For example, in one such embodiment m is a positive integer, z is zero and $R_{20}$ is hydrogen, aliphatic or heteroaliphatic. By way of further example, in one such embodiment m is a positive integer (e.g., 1 to 3), z is a positive integer (e.g., 1 to 2), $X_{11}$ is hydrogen, aliphatic or heteroaliphatic, and $R_{20}$ is hydrogen, aliphatic or heteroaliphatic. By way of further example, in one such embodiment m is a positive integer, z is zero, one or two, $X_{11}$ is hydrogen alkyl, alkenyl, or aminoalkyl, and $R_{20}$ is hydrogen, alkyl, alkenyl, or aminoalkyl.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and n is a positive integer and $R_{30}$ is hydrogen, aliphatic or heteroaliphatic. By way of further example, in one such embodiment n is 0 or 1, and $R_{30}$ is hydrogen, alkyl, alkenyl, or aminoalkyl.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently non-negative integers and $X_2$ is aliphatic or heteroaliphatic. For example, in one such embodiment m is 0 to 2, n is 0 or 1, $X_2$ is aliphatic or heteroaliphatic, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, alkyl, alkenyl, or aminoalkyl.

In some embodiments, the crosslinked polymer comprises the residue of an amine corresponding to Formula 2a and the crosslinked polymer is prepared by substitution polymerization of the amine corresponding to Formula 2a with a polyfunctional crosslinker (optionally also comprising amine moieties):

Formula 2a

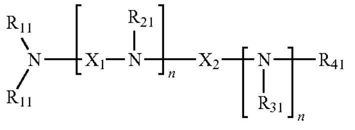

wherein m and n are independently non-negative integers;

each $R_{11}$ is independently hydrogen, hydrocarbyl, heteroaliphatic, or heteroaryl;

$R_{21}$ and $R_{31}$, are independently hydrogen or heteroaliphatic;

$R_{41}$ is hydrogen, substituted hydrocarbyl, or hydrocarbyl;

$X_1$ is

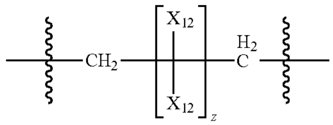

;

$X_2$ is alkyl or substituted hydrocarbyl;

each $X_{12}$ is independently hydrogen, hydroxy, amino, aminoalkyl, boronic acid or halo; and z is a non-negative number.

In one embodiment, the crosslinked polymer comprises the residue of an amine corresponding to Formula 2a, the crosslinked polymer is prepared by substitution polymerization of the amine corresponding to Formula 1 with a polyfunctional crosslinker (optionally also comprising amine moieties). For example, in one such embodiment, m and z are independently 0, 1, 2 or 3, and n is 0 or 1.

In one embodiment, the crosslinked polymer comprises the residue of an amine corresponding to Formula 2a, the crosslinked polymer is prepared by substitution polymerization of the amine corresponding to Formula 2a with a polyfunctional crosslinker (optionally also comprising amine moieties), and each $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl. For example, in one such embodiment each $R_{11}$ is hydrogen, aliphatic, aminoalkyl, or haloalkyl, $R_{21}$ and $R_{31}$ are independently hydrogen or heteroaliphatic and $R_{41}$ is hydrogen, alkylamino, aminoalkyl, aliphatic, or heteroaliphatic. By way of further example, in one such embodiment each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic. By way of further example, in one such embodiment each $R_{11}$ and $R_{41}$ is independently hydrogen, alkyl, or aminoalkyl, and $R_{21}$ and $R_{31}$ are independently hydrogen or heteroaliphatic. By way of further example, in one such embodiment each $R_{11}$ and $R_{41}$ is independently hydrogen, alkyl, $-(CH_2)_dNH_2$, $-(CH_2)_dN[(CH_2)_eNH_2]_2$ where d and e are independently 2-4, and $R_{21}$ and $R_{31}$ are independently hydrogen or heteroaliphatic. In each of the foregoing exemplary embodiments of this paragraph, m and z may independently be 0, 1, 2 or 3, and n is 0 or 1.

Exemplary amines for the synthesis of polymers comprising repeat units corresponding to Formula 2a include, but are not limited to, amines appearing in Table A.

TABLE A

| Abbreviation | IUPAC name | Other names | | MW (g/mol) |
|---|---|---|---|---|
| C2A3BTA | 1,3-Bis[bis(2-aminoethyl) amino]propane | | 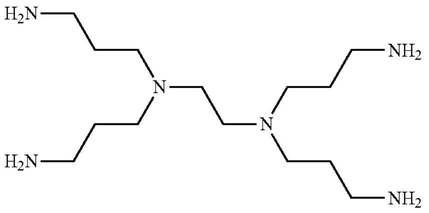 | 288.48 |

TABLE A-continued

| Abbreviation | IUPAC name | Other names | | MW (g/mol) |
|---|---|---|---|---|
| C2A3G2 | 3-Amino-1-{[2-(bis{2-[bis(3-aminopropyl)amino]ethyl}amino)ethyl](3-aminopropyl)amino}propane | | 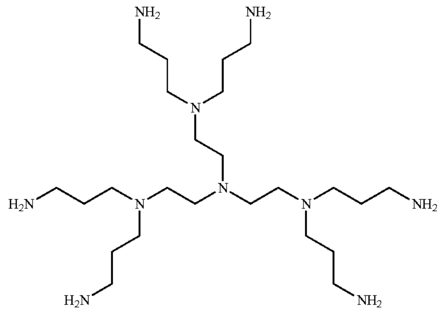 [SMILES: NCCCN(CCCN)CCN(CCN(CCCN)CCCN)CCN(CCCN)CCCN] | 488.81 |
| C2PW | 2-[Bis(2-aminoethyl)amino]ethanamine | 2,2',2"-Triaminotriethylamine or 2,2',2"-Nitrilotriethylamine | 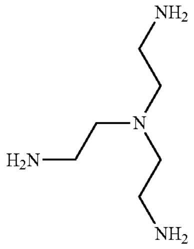 | 146.24 |
| C3PW | Tris(3-aminopropyl)amine | | 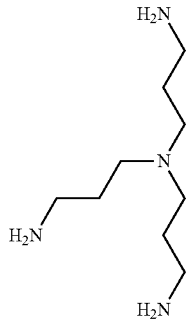 [SMILES: NCCCN(CCCN)CCCN] | 188.32 |
| C4A3BTA | 1,4-Bis[bis(3-aminopropyl)amino]butane | | 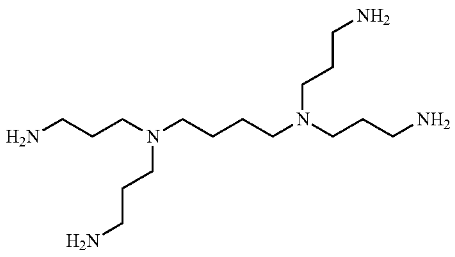 [SMILES: NCCCN(CCCN)CCCCN(CCCN)CCCN] | 316.54 |
| EDA1 | 1,2-Ethanediamine | | 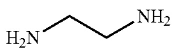 | 60.1 |
| EDA2 | 2-Amino-1-(2-aminoethylamino)ethane | Bis(2-aminoethyl)amine or 2,2'-Diaminodiethylamine | 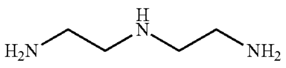 | 103.17 |
| EDA3 | 1,2-Bis(2-aminoethylamino)ethane | N,N'-Bis(2-aminoethyl)ethane-1,2-diamine | 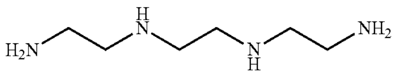 | 146.24 |
| PDA1 | 1,3-Propanediamine | | 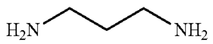 | 74.3 |
| PDA2 | 3,3'-Diaminodipropylamine | | 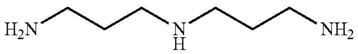 | 131.22 |

Exemplary crosslinkers for the synthesis of polymers comprising the residue of amines corresponding to Formula 2a include but are not limited to crosslinkers appearing in Table B.

TABLE B

| Abbreviation | Common name | IUPAC name | | MW (g/mol) |
|---|---|---|---|---|
| BCPA | Bis(3-chloropropyl)amine | Bis(3-chloropropyl)amine | 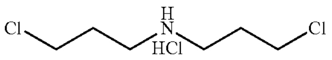 | 206.54 |
| DC2OH | 1,3-dichloroisopropanol | 1,3-Dichloro-2-propanol | 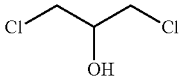 | 128.98 |
| DCE | dichloroethane | 1,2-dichloroethane | 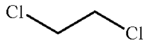 | 98.96 |
| DCP | Dichloropropane | 1,3-Dichloropropane | 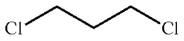 | 112.98 |
| ECH | Epichlorohydrin | 1-chloro-2,3-epoxypropane | 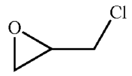 | 92.52 |
| TGA | Triglycidyl amine | Tris[(2-oxiranyl)methyl]amine | 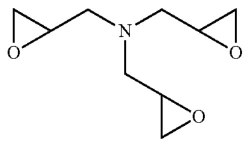 [SMILES: C1OC1CN(CC1CO1)CC1CO1] | 185.22 |
| BCPOH | Bis(3-chloropropyl) amine-OH | 3-Chloro-1-(3-chloropropylamino)-2-propanol | 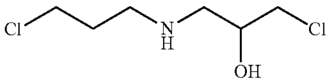 | 186.08 |
| BCPEDA | Bis(chloropropyl) ethylenediamine | 1,2-Bis(3-chloropropylamino) ethane | 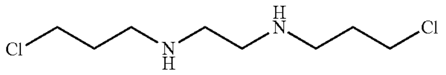 [SMILES: ClCCCNCCNCCCCl] | 213.15 |

In some embodiments, the crosslinked polymer comprises the residue of an amine corresponding to Formula 2b and the crosslinked polymer is prepared by radical polymerization of an amine corresponding to Formula 2b:

Formula 2b

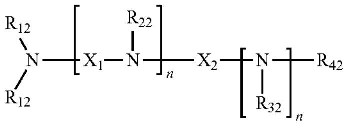

wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

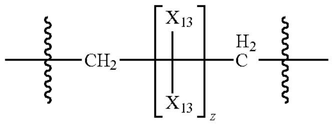

;

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

z is a non-negative number, and the amine corresponding to Formula 2b comprises at least one allyl group.

In one embodiment, the crosslinked polymer comprises the residue of an amine corresponding to Formula 2b, the crosslinked polymer is prepared by radical polymerization of an amine corresponding to Formula 2b, and m and z are independently 0, 1, 2 or 3, and n is 0 or 1.

In one embodiment, the crosslinked polymer comprises the residue of an amine corresponding to Formula 2b, the crosslinked polymer is prepared by radical polymerization of an amine corresponding to Formula 1, and (i) $R_{12}$ or $R_{42}$ independently comprise at least one allyl or vinyl moiety, (ii) m is a positive integer and $R_{22}$ comprises at least one allyl or vinyl moiety, and/or (iii) n is a positive integer and $R_{32}$ comprises at least one allyl moiety. For example, in one such embodiment, m and z are independently 0, 1, 2 or 3 and n is 0 or 1. For example, in one such embodiment $R_{12}$ or $R_{42}$, in combination comprise at least two allyl or vinyl moieties. By way of further example, in in one such embodiment, m is a positive integer and $R_{12}$, $R_{22}$ and $R_{42}$, in combination comprise at least two allyl or vinyl moieties. By way of further example, in in one such embodiment, n is a positive integer and $R_{12}$, $R_{32}$ and $R_{42}$, in combination comprise at least two allyl or vinyl moieties. By way of further example, in in one such embodiment, m is a positive integer, n is a positive integer and $R_{12}$, $R_{22}$, $R_{32}$ and $R_{42}$, in combination, comprise at least two allyl or vinyl moieties.

In one embodiment, the crosslinked polymer comprises the residue of an amine corresponding to Formula 2b, the crosslinked polymer is prepared by radical polymerization of an amine corresponding to Formula 2b, and each $R_{12}$ is independently hydrogen, aminoalkyl, allyl, or vinyl, $R_{22}$ and $R_{32}$ are independently hydrogen, alkyl, aminoalkyl, haloalkyl, alkenyl, alkanol, heteroaryl, alicyclic heterocyclic, or aryl, and $R_{42}$ is hydrogen or substituted hydrocarbyl. For example, in one such embodiment each $R_{12}$ is aminoalkyl, allyl or vinyl, $R_{22}$ and $R_{32}$ are independently hydrogen, alkyl, aminoalkyl, haloalkyl, alkenyl, or alkanol, and $R_{42}$ is hydrogen or substituted hydrocarbyl. By way of further example, in one such embodiment each $R_{12}$ and $R_{42}$ is independently hydrogen, alkyl, allyl, vinyl, $—(CH_2)_dNH_2$ or $—(CH_2)_dN[(CH_2)_eNH_2]_2$ where d and e are independently 2-4, and $R_{22}$ and $R_{32}$ are independently hydrogen or heteroaliphatic.

Exemplary amines and crosslinkers (or the salts thereof, for example the hydrochloric acid, phosphoric acid, sulfuric acid, or hydrobromic acid salts thereof) for the synthesis of polymers described by Formula 2b include but are not limited to the ones in Table C.

TABLE C

| Abbreviation | Common name | IUPAC name | | MW (g/mol) |
|---|---|---|---|---|
| DABDA1 | Diallylbutyldiamine | 1,4-Bis(allylamino)butane | 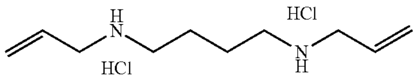 | 241.2 |
| DAEDA1 | Diallylethyldiamine | 1,2-Bis(allylamino)butane | 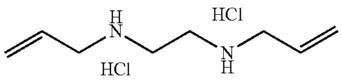 | 213.15 |
| DAEDA2 | Diallyldiethylenetriamine | 2-(Allylamino)-1-[2-(allylamino) ethylamino]ethane | 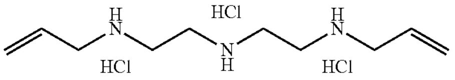 | 292.67 |
| DAPDA | Diallylpropyldiamine | 1,3-Bis(allylamino) propane | 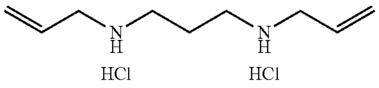 | 227.17 |
| POHDA | Diallylamineisopropanol | 1,3-Bis(allylamino)-2-propanol | 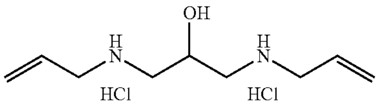 | 243.17 |
| AAH | Allylamine | 2-Propen-1-ylamine | 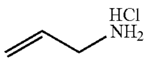 | 93.5 |
| AEAAH | Aminoethylallylamine | 1-(Allylamino)-2-aminoethane | 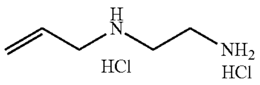 | 173.08 |
| BAEAAH | Bis(2-aminoethyl)allylamine | 1-[N-Allyl(2-aminoethyl)amino]-2-aminoethane | 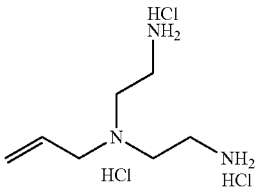 | 252.61 |

TABLE C-continued

| Abbreviation | Common name | IUPAC name | | MW (g/mol) |
|---|---|---|---|---|
| TAA | Triallylamine | N,N,N-triallylamine | 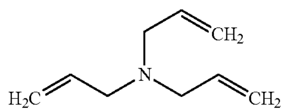 | 137.22 |

In some embodiments, the crosslinked polymer is derived from a reaction of the resulting polymers that utilize monomers described in any of Formulae 1, 1a, 1b, 1c, 2, 2a and 2b or a linear polymer comprised of a repeat unit described by Formula 3 with external crosslinkers or pre-existing polymer functionality that can serve as crosslinking sites. Formula 3 can be a repeat unit of a copolymer or terpolymer where $X_{15}$ is either a random, alternating, or block copolymer. The repeating unit in Formula 3 can also represent the repeating unit of a polymer that is branched, or hyperbranched, wherein the primary branch point can be from any atom in the main chain of the polymer:

Formula 3

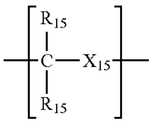

wherein $R_{15}$, $R_{16}$ and $R_{17}$ are independently hydrogen, hydrocarbyl, substituted hydrocarbyl, hydroxyl, amino, boronic acid or halo;

$X_{15}$ is

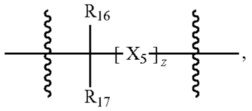

$X_5$ is hydrocarbyl, substituted hydrocarbyl, oxo (—O—), or amino and z is a non-negative number.

In one embodiment, $R_{15}$, $R_{16}$ and $R_{17}$ are independently hydrogen, aryl, or heteroaryl, $X_5$ is hydrocarbyl, substituted hydrocarbyl, oxo or amino, and m and z are non-negative integers. In another embodiment, $R_{15}$, $R_{16}$ and $R_{17}$ are independently aliphatic or heteroaliphatic, $X_5$ is hydrocarbyl, substituted hydrocarbyl, oxo (—O—) or amino, and m and z are non-negative integers. In another embodiment, $R_{15}$, $R_{16}$ and $R_{17}$ are independently unsaturated aliphatic or unsaturated heteroaliphatic, $X_5$ is hydrocarbyl, substituted hydrocarbyl, oxo, or amino, and z is a non-negative integer. In another embodiment, $R_{15}$, $R_{16}$ and $R_{17}$ are independently alkyl or heteroalkyl, $X_5$ is hydrocarbyl, substituted hydrocarbyl, oxo, or amino, and z is a non-negative integer. In another embodiment, $R_{15}$, $R_{16}$ and $R_{17}$ are independently alkylamino, aminoalkyl, hydroxyl, amino, boronic acid, halo, haloalkyl, alkanol, or ethereal, $X_5$ is hydrocarbyl, substituted hydrocarbyl, oxo, or amino, and z is a non-negative integer. In another embodiment, $R_{15}$, $R_{16}$ and $R_{17}$ are independently hydrogen, hydrocarbyl, substituted hydrocarbyl, hydroxyl, amino, boronic acid or halo, $X_5$ is oxo, amino, alkylamino, ethereal, alkanol, or haloalkyl, and z is a non-negative integer.

Exemplary crosslinking agents that may be used in radical polymerization reactions include, but are not limited to, one or more multifunctional crosslinking agents such as: 1,4-bis(allylamino)butane, 1,2-bis(allylamino)ethane, 2-(allylamino)-1-[2-(allylamino)ethylamino]ethane, 1,3-bis(allylamino)propane, 1,3-bis(allylamino)-2-propanol, triallylamine, diallylamine, divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, divinylbenzene, 1,4-divinyloxybutane, and combinations thereof.

Crosslinked polymers derived from the monomers and polymers in formulas 1 through 3 may be synthesized either in solution or bulk or in dispersed media. Examples of solvents that are suitable for the synthesis of polymers of the present disclosure include, but are not limited to water, low boiling alcohols (methanol, ethanol, propanol, butanol), dimethyformamide, dimethylsulfoxide, heptane, chlorobenzene, toluene.

Alternative polymer processes may include, a lone polymerization reaction, stepwise addition of individual starting material monomers via a series of reactions, the stepwise addition of blocks of monomers, combinations or any other method of polymerization such as living polymerization, direct polymerization, indirect polymerization, condensation, radical, emulsion, precipitation approaches, spray dry polymerization or using some bulk crosslinking reaction methods and size reduction processes such as grinding, compressing, extrusion. Processes can be carried out as a batch, semi-continuous and continuous processes. For processes in dispersed media, the continuous phase can be non-polar solvents, such as toluene, benzene, hydrocarbon, halogenated solvents, super critical carbon dioxide. With a direct suspension reaction, water can be used and salt can be used to tune the properties of the suspension.

The starting molecules described in formulas 1 through 3 may be copolymerized with one or more other monomers of the invention, oligomers or other polymerizable groups. Such copolymer architectures can include, but are not limited to, block or block-like polymers, graft copolymers, and random copolymers. Incorporation of monomers described by formulas 1 through 3 can range from 1% to 99%. In some embodiments, the incorporation of comonomer is between 20% and 80%.

Non-limiting examples of comonomers which may be used alone or in combination include: styrene, allylamine hydrochloride, substituted allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacryl amide, N-Nbutylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinylether, butadiene, isoprene, chloroprene, ethylene, vinyl acetate, and combinations thereof.

Additional modification to the preformed crosslinked polymer can be achieved through the addition of modifiers, including but not limited to amine monomers, additional crosslinkers, and polymers. Modification can be accomplished through covalent or non-covalent methods. These modifications can be evenly or unevenly dispersed throughout the preformed polymer material, including modifications biased to the surface of the preformed crosslinked polymer. Furthermore, modifications can be made to change the physical properties of the preformed crosslinked polymer, including but not limited to reactions that occur with remaining reactive groups such as haloalkyl groups and allyl groups in the preformed polymer. Reactions and modifications to the preformed crosslinked polymer can include but are not limited to acid-base reactions, nucleophilic substitution reactions, Michael reactions, non-covalent electrostatic interactions, hydrophobic interactions, physical interactions (crosslinking) and radical reactions.

In one embodiment, the post-polymerization crosslinked amine polymer is a crosslinked amine polymer comprising a structure corresponding to Formula 4:

Formula 4

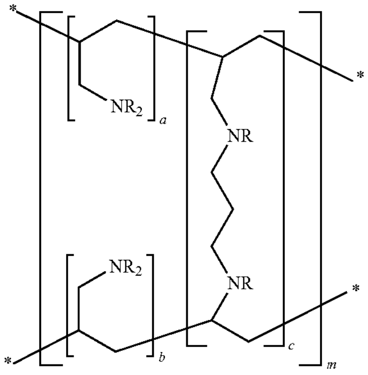

wherein each R is independently hydrogen or an ethylene crosslink between two nitrogen atoms of the crosslinked amine polymer

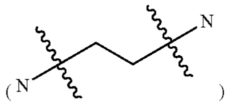

and a, b, c, and m are integers. Typically, m is a large integer indicating an extended polymer network. In one such embodiment, a ratio of the sum of a and b to c (i.e., a+b:c) is in the range of about 1:1 to 5:1. For example, in one such embodiment a ratio of the sum of a and b to c (i.e., a+b:c) is in the range of about 1.5:1 to 4:1. By way of further example, in one such embodiment a ratio of the sum of a and b to c (i.e., a+b:c) is in the range of about 1.75:1 to 3:1. For example, in one such embodiment a ratio of the sum of a and b is 57, c is 24 and m is large integer indicating an extended polymer network. In each of the foregoing embodiments a ratio of the sum of a and b to c (i.e., a+b:c) may be in the range of about 2:1 to 2.5:1. For example, in such embodiments the ratio of the sum of a and b to c (i.e., a+b:c) may be in the range of about 2.1:1 to 2.2:1. By way of further example, in such embodiments the ratio of the sum of a and b to c (i.e., a+b:c) may be in the range of about 2.2:1 to 2.3:1. By way of further example, in such embodiments the ratio of the sum of a and b to c (i.e., a+b:c) may be in the range of about 2.3:1 to 2.4:1. By way of further example, in such embodiments the ratio of the sum of a and b to c (i.e., a+b:c) may be in the range of about 2.4:1 to 2.5:1. In each of the foregoing embodiments, each R may independently be hydrogen or an ethylene crosslink between two nitrogen atoms. Typically, however, 35-95% of the R substituents will be hydrogen and 5-65% will be an ethylene crosslink

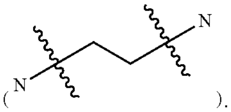

).

For example, in one such embodiment, 50-95% of the R substituents will be hydrogen and 5-50% will be an ethylene crosslink

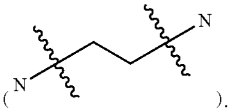

).

For example, in one such embodiment, 55-90% of the R substituents are hydrogen and 10-45% are an ethylene crosslink

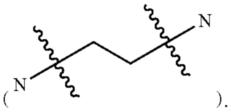

).

By way of further example, in one such embodiment, 60-90% of the R substituents are hydrogen and 10-40% are an ethylene crosslink. By way of further example, in one such embodiment, 65-90% of the R substituents are hydrogen and 10-35% are an ethylene crosslink.

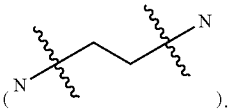

).

By way of further example, in one such embodiment, 70-90% of the R substituents are hydrogen and 10-30% are an ethylene crosslink. By way of further example, in one such embodiment, 75-85% of the R substituents are hydrogen and 15-25% are an ethylene crosslink. By way of further example, in one such embodiment, 65-75% of the R substituents are hydrogen and 25-35% are an ethylene crosslink. By way of further example, in one such embodiment, 55-65% of the R substituents are hydrogen and 35-45% are an ethylene crosslink. In some embodiments, a, b, c and R are such that the carbon to nitrogen ratio of the polymer of Formula 4 may range from about 2:1 to about 6:1, respectively. For example, in one such embodiment, the carbon to nitrogen ratio of the polymer of Formula 4 may range from about 2.5:1 to about 5:1, respectively. By way of further example, in one such embodiment, the carbon to nitrogen ratio of the polymer of Formula 4 may range from about 3:1 to about 4.5:1, respectively. By way of further example, in one such embodiment, the carbon to nitrogen ratio of the polymer of Formula 4 may range from about 3.25:1 to about 4.25:1, respectively. By way of further example, in one such embodiment, the carbon to nitrogen ratio of the polymer of Formula 4 may range from about 3.4:1 to about 4:1, respectively. By way of further example, in one such embodiment, the carbon to nitrogen ratio of the polymer of Formula 4 may range from about 3.5:1 to about 3.9:1, respectively. By way of further example, in one such embodiment, the carbon to nitrogen ratio of the polymer of Formula 4 may range from about 3.55:1 to about 3.85:1, respectively. In each of the foregoing embodiments recited in this paragraph, the polymer of Formula 4 is derived from monomers and crosslinkers, each of which comprise less than 5 wt % oxygen.

In certain embodiments, polymers in which crosslinking and/or entanglement were increased were found to have lower swelling than those with lower crosslinking and/or entanglement, yet also had a binding capacity for target ion (e.g., chloride) that was as great as or greater than the lower crosslinking and/or entanglement polymers while binding of interfering ions such as phosphate were significantly reduced. The selectivity effect may be introduced in two different manners: 1) Overall capacity was sacrificed for chloride specificity. Crosslinkers that don't include chloride binding sites (e.g., epichlorohydrin) allow for increased crosslinking while overall capacity is decreased proportional to the amount of crosslinker incorporated into the polymer. 2) Overall capacity is preserved for chloride specificity: Crosslinkers that include chloride binding sites (e.g., diallylamines) allow for increased crosslinking while overall capacity is staying the same or is reduced by only a small amount.

As previously noted, crosslinked polymers having a high capacity for chloride binding and high selectivity for chloride over other competing anions such as phosphate may be prepared in a two-step process in accordance with one embodiment of the present disclosure. In general, the selectivity of the polymer is a function of its crosslinking density and the capacity of the polymer is a function of the free amine density of the crosslinked polymer. Advantageously, the two-step process disclosed herein provides both, high capacity for chloride binding, and high selectivity for chloride over other competing ions by relying primarily upon carbon-carbon crosslinking in the first step, and nitrogen-nitrogen crosslinking in the second step.

In the first step, the crosslinking is preferably capacity-sparing, i.e., free amine sparing, crosslinking from carbon to carbon. In the second step, the crosslinking is amine-consuming and is directed towards tuning for selectivity. Based on the desired high capacity, the C—N ratio is preferably optimized to maximize amine functionalities for HCl binding, while still maintaining a spherical polymer particle of controlled particle size to ensure nonabsorption and acceptable mouth feel that is stable under GI conditions. The preferred extent of carbon-carbon crosslinking achieved after the first step is sufficient to permit the resulting bead to swell between 4× and 6× in water (i.e., a Swelling Ratio of 4 to 6).

In one embodiment, crosslinked polymers having a high capacity for chloride binding and high selectivity for chloride over other competing anions such as phosphate may be prepared in a two-step process, and the product of the first polymerization step is preferably in the form of beads whose diameter is controlled in the 5 to 1000 micromer range, preferably 10 to 500 micrometers and most preferred 40-180 micrometers.

The product of the first polymerization step is preferably in the form of beads whose Swelling Ratio in water is between 2 and 10, more preferably about 3 to about 8, and most preferably about 4 to about 6.

Additionally, if the crosslinked polymer beads resulting from the first polymerization step are protonated, this may reduce the amount of nitrogen-nitrogen crosslinking in the second crosslinking step. Accordingly, in certain embodiments the preformed amine polymer is at least partially deprotonated by treatment with a base, preferably a strong base such as a hydroxide base. For example, in one embodiment the base may be NaOH, KOH, $NH_4OH$, $NaHCO_3$, $Na_2CO_3$, $K_2CO_3$, LiOH, $Li_2CO_3$, CsOH or other metal hydroxides. If the charges are removed from the preformed crosslinked amine polymer bead by deprotonation, the bead will tend to collapse and the crosslinking agent used in the second step may not be able to access binding sites on the polymer unless the bead is prevented from collapsing. One means of preventing the crosslinked polymer bead from collapsing is the use of a swelling agent such as water to swell the bead, thereby allowing the second-step crosslinker to access binding sites.

The preformed polymer may be crosslinked to form the post-polymerization crosslinked polymer using any of a range of crosslinking compounds containing at least two amine-reactive functional groups. In one such embodiment, the crosslinker is a compound containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. The crosslinker may be, for example, any of the crosslinkers disclosed herein, including a crosslinker selected from Table B. By way of further example, in one such embodiment the crosslinker is a dihalide such as a dichloroalkane.

As noted above, in certain embodiments a swelling agent for the preformed amine polymer may be included in the reaction mixture for the second polymerization step along with the crosslinking agent. In general, the swelling agent and the crosslinking agent may be miscible or immiscible and the swelling agent may be any composition or combination of compositions that have the capacity to swell the preformed amine polymer. Exemplary swelling agents include polar solvents such as water, methanol, ethanol, n-propanol, isopropanol, n-butanol, formic acid, acetic acid, acetonitrile, dimethylformamide, dimethylsulfoxide, nitromethane, propylene carbonate, or a combination thereof. Additionally, the amount of swelling agent included in the reaction mixture will typically be less than absorption capacity of the preformed amine polymer for the swelling agent. For example, it is generally preferred that the weight ratio of swelling agent to preformed polymer in the reaction mixture be less than 4:1. By way of further example, in some embodiments the weight ratio of swelling agent to preformed polymer in the reaction mixture will be less than 3:1. By way of further example, in some embodiments the weight ratio of swelling agent to preformed polymer in the reaction mixture will be less than 2:1. By way of further example, in some embodiments the weight ratio of swelling agent to preformed polymer in the reaction mixture will be less than 1:1. By way of further example, in some embodiments the weight ratio of swelling agent to preformed polymer in the reaction mixture will be less than 0.5:1. By way of further example, in some embodiments the weight ratio of swelling agent to preformed polymer in the reaction mixture will be less than 0.4:1. By way of further example, in some embodiments the weight ratio of swelling agent to preformed polymer in the reaction mixture will be less than 0.3:1. In general, however, the weight ratio of swelling agent to preformed polymer in the reaction mixture will typically be at least 0.05:1, respectively.

In general, the crosslinked polymers may be crosslinked homopolymers or crosslinked copolymers comprising free amine moieties. The free amine moieties may be separated, for example, by the same or varying lengths of repeating linker (or intervening) units. In some embodiments, the polymers comprise repeat units containing an amine moiety and an intervening linker unit. In other embodiments, multiple amine-containing repeat units are separated by one or more linker units. Additionally, the polyfunctional crosslinkers may comprise HCl binding functional groups, e.g., amines, ("active crosslinkers") or may lack HCl binding functional groups such as amines ("passive crosslinkers").

In a preferred embodiment, the first polymerization (crosslinking) step yields preformed amine polymer beads having a target size and chloride binding capacity. For example, in one such embodiment the beads have a chloride binding capacity of at least 10 mmol/g in Simulated Gastric Fluid ("SGF") and a Swelling Ratio in the range of 1 to 6. The resulting preformed amine polymer is then preferably (at least partially) deprotonated with a base and combined with a non-protonating swelling agent to swell the free amine polymer without protonating the amine functions. Furthermore, the amount of the non-protonating swelling agent is selected to tune the subsequent degree of crosslinking effectively forming a template that is then locked into place via the amine consuming crosslinking step. In the second crosslinking step, the swollen, deprotonated preformed amine polymer is crosslinked with a crosslinker containing amine reactive moieties to form a post-polymerization crosslinked polymer.

In general, selectivity for chloride over other competing ions is achieved with highly crosslinked polymers. For example, relatively high chloride binding capacity maybe be attained by reacting a preformed amine polymer bead with neat crosslinker in the presence of a swelling agent (water). While this "non-dispersed" reaction provides access to high selectivity for chloride over competing ions in the SIB assay, it also results in macroscopically (and microscopically) aggregated polymer beads. Accordingly, it is advantageous to include a solvent (e.g., heptane) in the second crosslinking step to disperse the preformed crosslinked polymer beads so as to avoid inter-bead reactions and resulting aggregation. The use of too much solvent (dispersant), however, can dilute the reaction solution to the point where the resulting bead is not sufficiently crosslinked to have the desired selectivity for chloride over other competing anions. By using a crosslinking agent that also functions as a solvent (dispersant), however, sufficient solvent (dispersant) may be included in the reaction mixture to avoid inter-bead reactions and aggregation without diluting the mixture to the point where the degree of amine-consuming crosslinking is insufficient. For example, in an effort to utilize the dispersing properties of a solvent (to avoid aggregation during the reaction) while maintaining reactivity, DCE and DCP were used neat, thus performing a dual purpose role, as both solvent (dispersant) and crosslinker. Interestingly, DCE was discovered to have excellent dispersal properties as a solvent, when compared to similar reactions with DCP and/or heptane. Additionally, less aggregation was observed when the beads were first dispersed in DCE and then in a second operation, the water is added to swell the beads. If water is added to the preformed amine polymer before the bead is dispersed in the DCE, aggregation may occur.

The use of 1,2-dichloroethane ("DCE") as the crosslinking solvent also generates HCl molecules during the second step. These HCl molecules protonate some of the free amine sites which block the reaction sites for the crosslinking reaction and thereby limit the number of binding sites available for crosslinking. Consequently, the use of DCE creates a self-limiting effect on the secondary crosslinking.

In each of the foregoing embodiments, the reaction mixture may contain a wide range of amounts of crosslinking agents. For example, in one embodiment the crosslinker may be used in large excess relative to the amount of preformed amine polymer in the reaction mixtures. Stated differently, in such embodiments the crosslinking agent is a crosslinking solvent, i.e., it is both a solvent for the reaction mixture and a crosslinking agent for the preformed amine polymer. In such embodiments, other solvents may optionally be included in the reaction mixture but are not required. Alternatively, the preformed amine polymer, swelling agent and crosslinker may be dispersed in a solvent that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, N,N-dimethylformamide, dimethylsulfoxide, nitromethane, or a combination thereof. By way of further example, when the swelling agent comprises a polar solvent, the solvent system for the reaction mixture will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent may be the same; i.e., the solvent is a crosslinking solvent such as 1,2-dichloroethane, 1,3-dichloropropane, 1,4-dichlorobutane or a combination thereof.

It is notable that in a crosslinking solvent (e.g., a DCE-dispersed reaction), there is a large excess of crosslinker regardless of the amount of crosslinking solvent (e.g., DCE) used to disperse the bead (e.g., both 1 g:3 mL:bead:DCE and 1 g:10 mL:bead:DCE are a large excess of crosslinker, most of which is not consumed during the reaction). Despite this, the relative degree of crosslinking, and the performance in SIB assay, are unaffected by changes in the ratio of reactive crosslinker to polymer bead. This is possible because the reaction is limited by the acid-neutralizing capacity of the polymer bead, rather than the amount of crosslinker (e.g., DCE).

To more efficiently react with DCE or other crosslinker, the amines of the preformed polymer bead preferably have a free electron pair (neutral, deprotonated). As the free amines of the preformed polymer bead react with the crosslinker (e.g., DCE), HCl is produced and the amines become protonated, thus limiting the reaction. For this reason, the preformed amine polymer beads preferably start as the free amine in the second crosslinking step. If the preformed amine polymer bead is protonated after the first step of carbon-carbon crosslinking, amine-consuming crosslinking in the second step will be limited, thus reducing the desired selectivity for chloride over other competing ions. This has been demonstrated by adding known quantities of HCl to preformed amine polymer beads immediately before second step crosslinking with DCE (TABLE 7). When less than 3 mol % HCl (to amine in preformed polymer amine bead) is added prior to second step crosslinking, total chloride capacity (SGF) and chloride selectivity in SIB are similar to beads not treated with HCl in the second step. When greater than 5 mol % HCl (to amine in preformed polymer amine bead) is added prior to second step crosslinking, total chloride capacity (SGF) increases and chloride selectivity in SIB decreases, indicating lower incorporation of crosslinker.

The benefits of deprotonated preformed polymer beads in the second step crosslinking highlights the advantages of using two steps to achieve the final product. In the first step, to form the amine polymer bead, all monomers (e.g., allylamine and DAPDA) are protonated to remain in the aqueous phase and to avoid the radical transfer reactions that severely limit the polymerization of non-protonated allylamine (and derivatives). Once the bead is formed through carbon-carbon crosslinks, the bead can then be deprotonated and further crosslinked with an amine reactive crosslinker in a second step.

Given the large excess of dual crosslinker/solvent, mono-incorporation of this reagent can occur leading to alkyl chloride functional groups on the crosslinked polymer bead that are hydrophobic in nature and can increase non-specific interactions with undesirable solutes other than HCl that are more hydrophobic in nature. Washing with ammonium hydroxide solution converts the alkyl-chloride to alkyl-amine functions that are hydrophilic and minimize non-specific interactions with undesirable solutes. Other modifications that yield more hydrophilic groups than alkyl chloride such as —OH are suitable to quench mono-incorporated crosslinker/solvent.

Any of a range of polymerization chemistries may be employed in the first reaction step, provided that the crosslinking mechanism is primarily carbon-carbon crosslinking. Thus, in one exemplary embodiment, the first reaction step comprises radical polymerization. In such reactions, the amine monomer will typically be a mono-functional vinyl, allyl, or acrylamide (e.g., allylamine) and crosslinkers will have two or more vinyl, allyl or acrylamide functionalities (e.g., diallylamine). Concurrent polymerization and crosslinking occurs through radically initiated polymerization of a mixture of the mono- and multifunctional allylamines. The resulting polymer network is thusly crosslinked through the carbon backbone. Each crosslinking reaction forms a carbon-carbon bond (as opposed to substitution reactions in which a carbon-heteroatom bond is formed during crosslinking). During the concurrent polymerization and crosslinking, the amine functionalities of the monomers do not undergo crosslinking reactions and are preserved in the final polymer (i.e., primary amines remain primary, secondary amines remain secondary, and tertiary amines remain tertiary).

In those embodiments in which the first reaction step comprises radical polymerization, a wide range of initiators may be used including cationic and radical initiators. Some examples of suitable initiators that may be used include: the free radical peroxy and azo type compounds, such as azodiisobutyronitrile, azodiisovaleronitrile, dimethylazodiisobutyrate, 2,2'azo bis(isobutyronitrile), 2,2'-azobis(N,N'-dimethyl-eneisobutyramidine)dihydrochloride, 2,2'-azobis (2-amidinopropane)dihydrochloride, 2,2'-azobis(N,N'-dimethyleneisobutyramidine), 1,1'-azo bis(I-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, dimethyl bis(butylperoxy)hexane.

Exemplary amine-containing polymers as described above are more fully disclosed and exemplified in WO2016/094685 and WO2014/197725, the entire contents of which are incorporated herein by reference.

In one embodiment, the pharmaceutical composition comprises a mixture of any of the previously-identified nonabsorbable materials. For example, in one embodiment the pharmaceutical composition comprises a mixture of a cation exchange composition with at least one anion exchange composition, amphoteric ion exchange composition, or neutral composition having the capacity to bind both protons and anions. In another embodiment, the pharmaceutical composition comprises a mixture of an anion exchange composition with at least one cation exchange composition, amphoteric ion exchange composition, or neutral composition having the capacity to bind both protons and anions. In yet another embodiment, the pharmaceutical composition comprises a mixture of a neutral composition having the capacity to bind both protons and anions with at least one cation exchange composition, amphoteric ion exchange composition, or anion exchange composition.

Figure 1B:
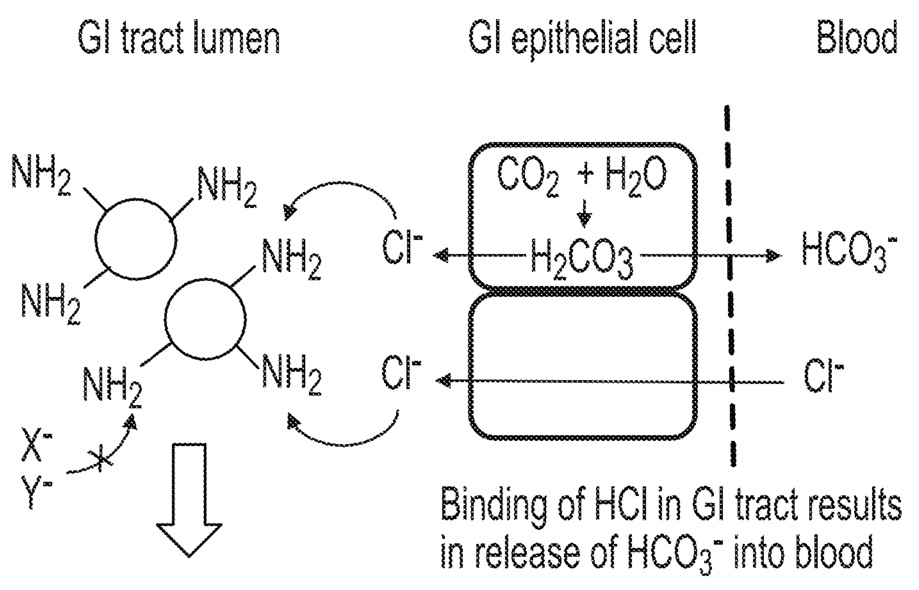
Figure 1C:
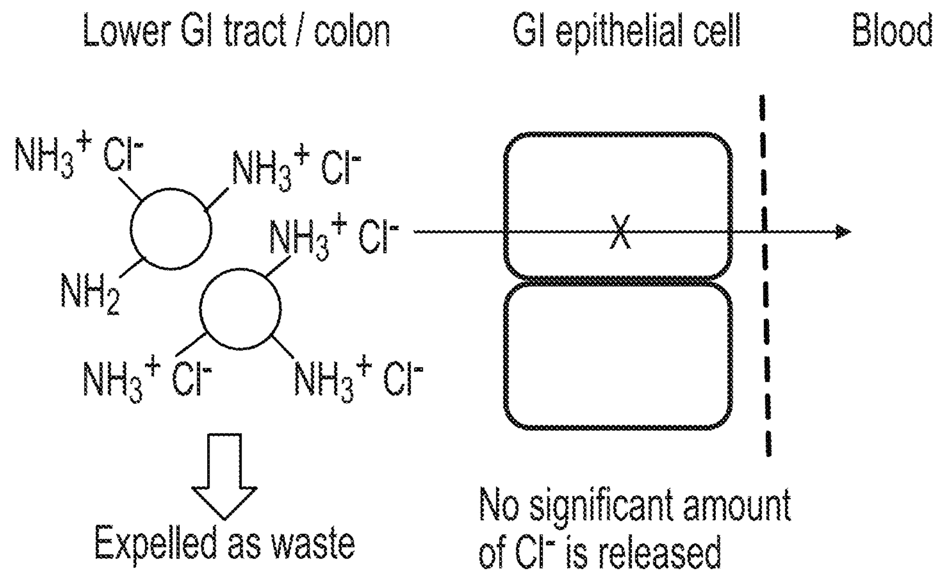

As schematically depicted in FIGS. 1A-1C and in accordance with one embodiment, a nonabsorbable free-amine polymer of the present disclosure is orally ingested and used to treat metabolic acidosis (including by increasing serum bicarbonate and normalizing blood pH) in a mammal by binding HCl in the gastrointestinal ("GI") tract and removing HCl through the feces. Free-amine polymer is taken orally (FIG. 1A) at compliance enhancing dose targeted to chronically bind sufficient amounts of HCl to enable clinically meaningful increase in serum bicarbonate of 3 mEq/L. In the stomach (FIG. 1B), free amine becomes protonated by binding $H^+$. Positive charge on polymer is then available to bind $Cl^-$; by controlling access of binding sites through crosslinking and hydrophilicity/hydrophobicity properties, other larger organic anions (e.g., acetate, propionate, butyrate, etc., depicted as $X^-$ and $Y^-$) are bound to a lesser degree, if at all. The net effect is therefore binding of HCl. In the lower GI tract/colon (FIG. 1C), $Cl^-$ is not fully released and HCl is removed from the body through regular bowel movement and fecal excretion, resulting in net alkalinization in the serum. $Cl^-$ bound in this fashion is not available for exchange via the $Cl^-/HCO_3^-$ antiporter system.

In one embodiment, the polymer is designed to simultaneously maximize efficacy (net HCl binding and excretion) and minimize GI side effects (through low swelling particle design and particle size distribution). Optimized HCl binding may be accomplished through a careful balance of capacity (number of amine binding sites), selectivity (preferred binding of chloride versus other anions, in particular organic anions in the colon) and retention (not releasing significant amounts of chloride in the lower GI tract to avoid the activity of the $Cl^-/HCO_3^-$ exchanger [antiporter] in the colon and intestine; if chloride is not tightly bound to the polymer the $Cl^-/HCO_3^-$ exchanger can mediate uptake of chloride ion from the intestinal lumen and reciprocal exchange for bicarbonate from the serum, thus effectively decreasing serum bicarbonate.

Competing anions that displace chloride lead to a decrease in net bicarbonate through the following mechanisms. First, displacement of chloride from the polymer in the GI lumen, particularly the colon lumen, provides for a facile exchange with bicarbonate in the serum. The colon has an anion exchanger (chloride/bicarbonate antiporter) that moves chloride from the luminal side in exchange for secreted bicarbonate. When free chloride is released from the polymer in the GI tract it will exchange for bicarbonate, which will then be lost in the stool and cause a reduction in total extracellular bicarbonate (Davis, 1983; D'Agostino, 1953). The binding of short chain fatty acids (SCFA) in exchange for bound chloride on the polymer, will result in the depletion of extracellular $HCO_3^-$ stores. Short chain fatty acids are the product of bacterial metabolism of complex carbohydrates that are not catabolized by normal digestive processes (Chemlarova, 2007). Short chain fatty acids that reach the colon are absorbed and distributed to various tissues, with the common metabolic fate being the generation of $H_2O$ and $CO_2$, which is converted to bicarbonate equivalents. Thus, binding of SCFA to the polymer to neutralize the proton charge would be detrimental to overall bicarbonate stores and buffering capacity, necessitating the design of chemical and physical features in the polymer that limit SCFA exchange. Finally, phosphate binding to the polymer should be limited as well, since phosphate represents an additional source of buffering capacity in the situation where ammoniagenesis and/or hydrogen ion secretion is compromised in chronic renal disease.

For each binding of proton, an anion is preferably bound as the positive charge seeks to leave the human body as a neutral polymer. "Binding" of an ion, is more than minimal binding, i.e., at least about 0.2 mmol of ion/g of polymer, at least about 1 mmol of ion/g of polymer in some embodiments, at least about 1.5 mmol of ion/g of polymer in some embodiments, at least about 3 mmol of ion/g of polymer in some embodiments, at least about 5 mmol of ion/g of polymer in some embodiments, at least about 10 mmol of ion/g of polymer in some embodiments, at least about 12 mmol of ion/g of polymer in some embodiments, at least about 13 mmol of ion/g of polymer in some embodiments, or even at least about 14 mmol of ion/g of polymer in some embodiments. In one embodiment, the polymers are characterized by their high capacity of proton binding while at the same time providing selectivity for anions; selectivity for chloride is accomplished by reducing the binding of interfering anions that include but are not limited to phosphate, citrate, acetate, bile acids and fatty acids. For example, in some embodiments, polymers of the present disclosure bind phosphate with a binding capacity of less than about 5 mmol/g, less than about 4 mmol/g, less than about 3 mmol/g, less than about 2 mmol/g or even less than about 1 mmol/g. In some embodiments, polymers of the invention bind bile and fatty acids with a binding capacity of less than about less than about 5 mmol/g, less than about 4 mmol/g, less than about 3 mmol/g, less than about 2 mmol/g, less than about 1 mmol/g in some embodiments, less than about 0.5 mmol/g in some embodiments, less than about 0.3 mmol/g in some embodiments, and less than about 0.1 mmol/g in some embodiments.

Pharmaceutical Compositions & Administration

In general, the dosage levels of the nonabsorbable compositions for therapeutic and/or prophylactic uses may range from about 0.5 g/day to about 100 g/day. To facilitate patient compliance, it is generally preferred that the dose be in the range of about 1 g/day to about 50 g/day. For example, in one such embodiment, the dose will be about 2 g/day to about 25 g/day. By way of further example, in one such embodiment, the dose will be about 3 g/day to about 25 g/day. By way of further example, in one such embodiment, the dose will be about 4 g/day to about 25 g/day. By way of further example, in one such embodiment, the dose will be about 5 g/day to about 25 g/day. By way of further example, in one such embodiment, the dose will be about 2.5 g/day to about 20 g/day. By way of further example, in one such embodiment, the dose will be about 2.5 g/day to about 15 g/day. By way of further example, in one such embodiment, the dose will be about 1 g/day to about 10 g/day. Optionally, the daily dose may be administered as a single dose (i.e., one time a day), or divided into multiple doses (e.g., two, three or more doses) over the course of a day. In general, the nonabsorbable compositions may be administered as a fixed daily dose or titrated based on the serum bicarbonate values of the patient in need of treatment or other indicators of acidosis. The titration may occur at the onset of treatment or throughout, as required, and starting and maintenance dosage levels may differ from patient to patient based on severity of the underlying disease.

The effectiveness of the nonabsorbable composition may be established in animal models, or in human volunteers and patients. In addition, in vitro, ex vivo and in vivo approaches are useful to establish HCl binding. In vitro binding solutions can be used to measure the binding capacity for proton, chloride and other ions at different pHs. Ex vivo extracts, such as the gastrointestinal lumen contents from human volunteers or from model animals can be used for similar purposes. The selectivity of binding and/or retaining certain ions preferentially over others can also be demonstrated in such in vitro and ex vivo solutions. In vivo models of metabolic acidosis can be used to test the effectiveness of the nonabsorbable composition in normalizing acid/base balance—for example 5/6 nephrectomized rats fed casein-containing chow (as described in Phisitkul S, Hacker C, Simoni J, Tran R M, Wesson D E. Dietary protein causes a decline in the glomerular filtration rate of the remnant kidney mediated by metabolic acidosis and endothelin receptors. Kidney international. 2008; 73(2):192-9), or adenine-fed rats (Terai K, K Mizukami and M Okada. 2008. Comparison of chronic renal failure rats and modification of the preparation protocol as a hyperphosphatemia model. Nephrol. 13:139-146).

In one embodiment, the nonabsorbable compositions are provided (by oral administration) to an animal, including a human, in a dosing regimen of one, two or even multiple (i.e., at least three) doses per day to treat an acid-base disorder (e.g., metabolic acidosis) and achieve a clinically significant and sustained increase of serum bicarbonate as previously described. For example, in one embodiment a daily dose of the nonabsorbable composition (whether orally administered in a single dose or multiple doses over the course of the day) has sufficient capacity to remove at least 5 mmol of protons, chloride ions or each per day. By way of further example, in one such embodiment a daily dose of the nonabsorbable composition has sufficient capacity to remove at least 10 mmol of protons, chloride ions or each per day. By way of further example, in one such embodiment a daily dose of the nonabsorbable composition has sufficient capacity to remove at least 20 mmol of protons, the conjugate base of a strong acid (e.g., $Cl^-$, $HSO_4^-$ and $SO_4^{2-}$) and/or a strong acid (e.g., HCl or $H_2SO_4$) each per day. By way of further example, in one such embodiment a daily dose of the nonabsorbable composition has sufficient capacity to remove at least 30 mmol of protons, the conjugate base of a strong acid, and/or a strong acid each per day. By way of further example, in one such embodiment a daily dose of the nonabsorbable composition has sufficient capacity to remove at least 40 mmol of protons, the conjugate base of a strong acid, and/or a strong acid each per day. By way of further example, in one such embodiment a daily dose of the nonabsorbable composition has sufficient capacity to remove at least 50 mmol of protons, the conjugate base of a strong acid, and/or a strong acid each per day.

The dosage unit form of the pharmaceutical comprising the nonabsorbable composition may be any form appropriate for oral administration. Such dosage unit forms include powders, tablets, pills, lozenges, sachets, cachets, elixirs, suspensions, syrups, soft or hard gelatin capsules, and the like. In one embodiment, the pharmaceutical composition comprises only the nonabsorbable composition. Alternatively, the pharmaceutical composition may comprise a carrier, a diluent, or excipient in addition to the nonabsorbable composition. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc. Pharmaceutical excipients useful in the pharmaceutical compositions further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumarate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), Remington's Pharmaceutical Sciences, 20th Edition.

In one embodiment, the nonabsorbable composition may be co-administered with other active pharmaceutical agents depending on the condition being treated. This co-administration may include simultaneous administration of the two agents in the same dosage form, simultaneous administration in separate dosage forms, and separate administration. For example, for the treatment of metabolic acidosis, the nonabsorbable composition may be co-administered with common treatments that are required to treat underlying co-morbidities including but not limited to edema, hypertension, diabetes, obesity, heart failure and complications of Chronic Kidney Disease. These medications and the nonabsorbable composition can be formulated together in the same dosage form and administered simultaneously as long as they do not display any clinically significant drug-drug-interactions. Alternatively, these treatments and the nonabsorbable composition may be separately and sequentially administered with the administration of one being followed by the administration of the other.

In one embodiment, the daily dose of the chronic metabolic acidosis treatment is compliance enhancing (approximately 15 g or less per day) and achieves a clinically significant and sustained increase of serum bicarbonate of approximately 3 mEq/L at these daily doses. The non-absorbed nature of the polymer and the lack of sodium load and/or introduction of other deleterious ions for such an oral drug enable for the first time a safe, chronic treatment of metabolic acidosis without worsening blood pressure/hypertension and/or without causing increased fluid retention and fluid overload. Another benefit is further slowing of the progression of kidney disease and time to onset of lifelong renal replacement therapy (End Stage Renal Disease "ESRD" including 3 times a week dialysis) or need for kidney transplants. Both are associated with significant mortality, low quality of life and significant burden to healthcare systems around the world. In the United States alone, approximately 20% of the 400,000 ESRD patients die and 100,000 new patients start dialysis every year.

A further aspect of the present disclosure is a pharmaceutical product comprising a sealed package and the nonabsorbable composition of the present disclosure within the sealed package. The sealed package is preferably substantially impermeable to moisture and oxygen to increase the stability of the pharmaceutical composition. For example, the dosage unit form may comprise a sealed container (e.g., a sealed sachet) that prevents or reduces ingress of moisture and oxygen upon packaging the nonabsorbable composition in the container. The container size can be optimized to reduce head space in the container after packaging and any head space may be filled with an inert gas such as nitrogen. Furthermore, container material of construction can be chosen to minimize the moisture and oxygen ingress inside the container after packaging. For example, the nonabsorbable composition may be packaged in a multilayer sachet containing at least one or more layer that serves as a barrier layer to moisture and oxygen ingress. In another example, the nonabsorbable composition may be packaged in a single layer or multilayer plastic, metal or glass container that has at least one or more barrier layers incorporated in the structure that limits oxygen and/or moisture ingress after packaging. For example, in one such embodiment the sachet (or other container or package) may comprise a multi-layer laminate of an inner contact layer, an outer layer; and a barrier layer disposed between the contact layer and outer layer. In one exemplary embodiment, the container includes one or more oxygen-scavenging layers.

In further embodiments, enumerated as embodiments 1-849 below, the present disclosure includes:

Embodiment 1. A method of treating an individual afflicted with an acid-base disorder characterized by a baseline serum bicarbonate value of less than 22 mEq/l, the method comprising oral administration of a daily dose of a pharmaceutical composition having the capacity to bind at least 5 mEq of protons and chloride ions as it transits the digestive system to achieve a clinically significant increase in the serum bicarbonate value of at least 1 mEq/l from baseline within a treatment period not greater than 1 month.

Embodiment 2. A method of treating an individual afflicted with an acid-base disorder characterized by a baseline serum bicarbonate value of less than 22 mEq/l, the method comprising oral administration of a pharmaceutical composition, wherein the pharmaceutical composition given orally binds at least 5 mEq per day on average of protons and chloride ions in the digestive system, said oral administration achieving a clinically significant increase in the serum bicarbonate value of at least 1 mEq/l from baseline within a treatment period not greater than 1 month.

Embodiment 3. The method of embodiment 2 wherein the oral administration is as frequent as at least weekly within the treatment period.

Embodiment 4. The method of embodiment 2 pharmaceutical composition wherein the oral administration is as frequent as at least semi-weekly within the treatment period.

Embodiment 5. The method of embodiment 2 pharmaceutical composition wherein the oral administration is as frequent as at least daily within the treatment period.

Embodiment 6. The method of embodiment 1, 2, 3 or 5 wherein the acid-base disorder is characterized by a baseline serum bicarbonate value of less than 21 mEq/l.

Embodiment 7. The method of embodiment 1, 2, 3 or 5 wherein the acid-base disorder is characterized by a baseline serum bicarbonate value of less than 20 mEq/l.

Embodiment 8. The method of embodiment 1, 2, 3 or 5 wherein the acid-base disorder is characterized by a baseline serum bicarbonate value of less than 19 mEq/l.

Embodiment 9. The method of embodiment 1, 2, 3 or 5 wherein the acid-base disorder is characterized by a baseline serum bicarbonate value of less than 18 mEq/l.

Embodiment 10. The method of embodiment 1, 2, 3 or 5 wherein the acid-base disorder is characterized by a baseline serum bicarbonate value of less than 17 mEq/l.

Embodiment 11. The method of embodiment 1, 2, 3 or 5 wherein the acid-base disorder is characterized by a baseline serum bicarbonate value of less than 16 mEq/l.

Embodiment 12. The method of embodiment 1, 2, 3 or 5 wherein the acid-base disorder is characterized by a baseline serum bicarbonate value of less than 15 mEq/l.

Embodiment 13. The method of embodiment 1, 2, 3 or 5 wherein the acid-base disorder is characterized by a baseline serum bicarbonate value of less than 14 mEq/l.

Embodiment 14. The method of embodiment 1, 2, 3 or 5 wherein the acid-base disorder is characterized by a baseline serum bicarbonate value of less than 13 mEq/l.

Embodiment 15. The method of embodiment 1, 2, 3 or 5 wherein the acid-base disorder is characterized by a baseline serum bicarbonate value of less than 12 mEq/l.

Embodiment 16. The method of embodiment 1, 2, 3 or 5 wherein the acid-base disorder is characterized by a baseline serum bicarbonate value of less than 11 mEq/l.

Embodiment 17. The method of embodiment 1, 2, 3 or 5 wherein the acid-base disorder is characterized by a baseline serum bicarbonate value of less than 10 mEq/l.

Embodiment 18. The method of any preceding enumerated embodiment wherein the acid-base disorder is characterized by a baseline serum bicarbonate value of at least 9 mEq/l.

Embodiment 19. The method of any of embodiments 1-16 wherein the acid-base disorder is characterized by a baseline serum bicarbonate value of at least 10 mEq/l.

Embodiment 20. The method of any of embodiments 1-15 wherein the acid-base disorder is characterized by a baseline serum bicarbonate value of at least 11 mEq/l.

Embodiment 21. The method of any of embodiments 1-14 wherein the acid-base disorder is characterized by a baseline serum bicarbonate value of at least 12 mEq/l.

Embodiment 22. The method of any of embodiments 1-13 wherein the acid-base disorder is characterized by a baseline serum bicarbonate value of at least 13 mEq/l.

Embodiment 23. The method of any of embodiments 1-12 wherein the acid-base disorder is characterized by a baseline serum bicarbonate value of at least 14 mEq/l.

Embodiment 24. The method of any of embodiments 1-11 wherein the acid-base disorder is characterized by a baseline serum bicarbonate value of at least 15 mEq/l.

Embodiment 25. The method of any of embodiments 1-10 wherein the acid-base disorder is characterized by a baseline serum bicarbonate value of at least 16 mEq/l.

Embodiment 26. The method of any of embodiments 1-9 wherein the acid-base disorder is characterized by a baseline serum bicarbonate value of at least 17 mEq/l.

Embodiment 27. The method of any of embodiments 1-8 wherein the acid-base disorder is characterized by a baseline serum bicarbonate value of at least 18 mEq/l.

Embodiment 28. The method of any of embodiments 1-7 wherein the acid-base disorder is characterized by a baseline serum bicarbonate value of at least 19 mEq/l.

Embodiment 29. The method of any of embodiments 1-6 wherein the acid-base disorder is characterized by a baseline serum bicarbonate value of at least 20 mEq/l.

Embodiment 30. The method of embodiment 1, 2, 3 or 5 wherein the acid-base disorder is characterized by a baseline serum bicarbonate value of at least 21 mEq/l.

Embodiment 31. The method of any preceding enumerated embodiment wherein the method increases the serum bicarbonate value from the baseline serum bicarbonate value to an increased serum bicarbonate value of at least 22 mEq/l.

Embodiment 32. The method of any preceding enumerated embodiment wherein the method increases the serum bicarbonate value from the baseline serum bicarbonate value to an increased serum bicarbonate value of at least 23 mEq/l.

Embodiment 33. The method of any preceding enumerated embodiment wherein the method increases the serum bicarbonate value from the baseline serum bicarbonate value to an increased serum bicarbonate value of at least 24 mEq/l.

Embodiment 34. The method of any preceding enumerated embodiment wherein the method increases the serum bicarbonate value from the baseline serum bicarbonate value to an increased serum bicarbonate value of at least 25 mEq/l.

Embodiment 35. The method of any preceding enumerated embodiment wherein the method increases the serum bicarbonate value from the baseline serum bicarbonate value to an increased serum bicarbonate value of at least 26 mEq/l.

Embodiment 36. The method of any preceding enumerated embodiment wherein the method increases the serum bicarbonate value from the baseline serum bicarbonate value to an increased serum bicarbonate value of at least 27 mEq/l.

Embodiment 37. The method of any preceding enumerated embodiment wherein the method increases the serum bicarbonate value from the baseline serum bicarbonate value to an increased serum bicarbonate value of at least 28 mEq/l.

Embodiment 38. The method of any preceding enumerated embodiment wherein the method increases the baseline serum bicarbonate value to an increased serum bicarbonate value not in excess of 29 mEq/l.

Embodiment 39. The method of any of embodiments 1 to 36 wherein the method increases the baseline serum bicarbonate value to an increased serum bicarbonate value not in excess of 28 mEq/l.

Embodiment 40. The method of any of embodiments 1 to 35 wherein the method increases the baseline serum bicarbonate value to an increased serum bicarbonate value not in excess of 27 mEq/l.

Embodiment 41. The method of any of embodiments 1 to 34 wherein the method increases the baseline serum bicarbonate value to an increased serum bicarbonate value not in excess of 26 mEq/l.

Embodiment 42. The method of any of embodiments 1 to 33 wherein the method increases the baseline serum bicarbonate value to an increased serum bicarbonate value not in excess of 25 mEq/l.

Embodiment 43. The method of any preceding enumerated embodiment wherein the method increases the baseline serum bicarbonate value to an increased serum bicarbonate value not in excess of 24 mEq/l.

Embodiment 44. The method of any preceding enumerated embodiment wherein the method increases the baseline serum bicarbonate value to an increased serum bicarbonate value not in excess of 23 mEq/l.

Embodiment 45. The method of any preceding enumerated embodiment wherein the clinically significant increase is at least 1 mEq/l.

Embodiment 46. The method of any preceding enumerated embodiment wherein the clinically significant increase is at least 1.5 mEq/l.

Embodiment 47. The method of any preceding enumerated embodiment wherein the clinically significant increase is at least 2 mEq/l.

Embodiment 48. The method of any preceding enumerated embodiment wherein the clinically significant increase is at least 2.5 mEq/l.

Embodiment 49. The method of any preceding enumerated embodiment wherein the clinically significant increase is at least 3 mEq/l.

Embodiment 50. The method of any preceding enumerated embodiment wherein the clinically significant increase is at least 3.5 mEq/l.

Embodiment 51. The method of any preceding enumerated embodiment wherein the clinically significant increase is at least 4 mEq/l.

Embodiment 52. The method of any preceding enumerated embodiment wherein the clinically significant increase is at least 4.5 mEq/l.

Embodiment 53. The method of any preceding enumerated embodiment wherein the clinically significant increase is at least 5 mEq/l.

Embodiment 54. The method of any preceding enumerated embodiment wherein the clinically significant increase is at least 5.5 mEq/l.

Embodiment 55. The method of any preceding enumerated embodiment wherein the clinically significant increase is at least 6 mEq/l.

Embodiment 56. The method of any preceding enumerated embodiment wherein the clinically significant increase is at least 6.5 mEq/l.

Embodiment 57. The method of any preceding enumerated embodiment wherein the clinically significant increase is at least 7 mEq/l.

Embodiment 58. The method of any preceding enumerated embodiment wherein the clinically significant increase is at least 7.5 mEq/l.

Embodiment 59. The method of any preceding enumerated embodiment wherein the clinically significant increase is at least 8 mEq/l.

Embodiment 60. The method of any preceding enumerated embodiment wherein the clinically significant increase is at least 8.5 mEq/l.

Embodiment 61. The method of any preceding enumerated embodiment wherein the clinically significant increase is at least 9 mEq/l.

Embodiment 62. The method of any preceding enumerated embodiment wherein the clinically significant increase is achieved within a treatment period of less than one month.

Embodiment 63. The method of any preceding enumerated embodiment wherein the clinically significant increase is achieved within a treatment period of 25 days.

Embodiment 64. The method of any preceding enumerated embodiment wherein the clinically significant increase is achieved within a treatment period of 3 weeks.

Embodiment 65. The method of any preceding enumerated embodiment wherein the clinically significant increase is achieved within a treatment period of 15 days.

Embodiment 66. The method of any preceding enumerated embodiment wherein the clinically significant increase is achieved within a treatment period of 2 weeks.

Embodiment 67. The method of any preceding enumerated embodiment wherein the clinically significant increase is achieved within a treatment period of 10 days.

Embodiment 68. The method of any preceding enumerated embodiment wherein the clinically significant increase is achieved within a treatment period of 1 week.

Embodiment 69. The method of any preceding enumerated embodiment wherein the clinically significant increase is achieved within 6 days of the initiation of the treatment.

Embodiment 70. The method of any preceding enumerated embodiment wherein the clinically significant increase is achieved within a treatment period of 5 days.

Embodiment 71. The method of any preceding enumerated embodiment wherein the clinically significant increase is achieved within a treatment period of 4 days.

Embodiment 72. The method of any preceding enumerated embodiment wherein the clinically significant increase is achieved within a treatment period of 3 days.

Embodiment 73. The method of any preceding enumerated embodiment wherein the clinically significant increase is achieved within a treatment period of 2 days.

Embodiment 74. The method of any preceding enumerated embodiment wherein the clinically significant increase is achieved within a treatment period of 1 day.

Embodiment 75. The method of any preceding enumerated embodiment wherein the clinically significant increase is achieved within a treatment period of 12 hours.

Embodiment 76. The method of any preceding enumerated embodiment wherein the clinically significant increase is achieved without any change in the individual's diet or dietary habits relative to the period immediately preceding the initiation of treatment.

Embodiment 77. The method of any preceding enumerated embodiment wherein the clinically significant increase is achieved independent of the individual's diet or dietary habits.

Embodiment 78. The method of any preceding enumerated embodiment wherein the individual's serum bicarbonate value returns to the baseline value ±2.5 mEq/l within 1 month of the cessation of treatment.

Embodiment 79. The method of any preceding enumerated embodiment wherein the individual's serum bicarbonate value returns to the baseline value ±2.5 mEq/l within 3 weeks of the cessation of treatment.

Embodiment 80. The method of any preceding enumerated embodiment wherein the individual's serum bicarbonate value returns to the baseline value ±2.5 mEq/l within 2 weeks of the cessation of treatment.

Embodiment 81. The method of any preceding enumerated embodiment wherein the individual's serum bicarbonate value returns to the baseline value ±2 mEq/l within 1 month of the cessation of treatment.

Embodiment 82. The method of any preceding enumerated embodiment wherein the individual's serum bicarbonate value returns to the baseline value ±2 mEq/l within 3 weeks of the cessation of treatment.

Embodiment 83. The method of any preceding enumerated embodiment wherein the individual's serum bicarbonate value returns to the baseline value ±2 mEq/l within 2 weeks of the cessation of treatment.

Embodiment 84. The method of any preceding enumerated embodiment wherein the individual's serum bicarbonate value returns to the baseline value ±1.5 mEq/l within 1 month of the cessation of treatment.

Embodiment 85. The method of any preceding enumerated embodiment wherein the individual's serum bicarbonate value returns to the baseline value ±1.5 mEq/l within 3 weeks of the cessation of treatment.

Embodiment 86. The method of any preceding enumerated embodiment wherein the individual's serum bicarbonate value returns to the baseline value ±1.5 mEq/l within 2 weeks of the cessation of treatment.

Embodiment 87. The method of any preceding enumerated embodiment wherein the individual's serum bicarbonate value returns to the baseline value ±1 mEq/l within 1 month of the cessation of treatment.

Embodiment 88. The method of any preceding enumerated embodiment wherein the individual's serum bicarbonate value returns to the baseline value ±1 mEq/l within 3 weeks of the cessation of treatment.

Embodiment 89. The method of any preceding enumerated embodiment wherein the individual's serum bicarbonate value returns to the baseline value ±1 mEq/l within 2 weeks of the cessation of treatment.

Embodiment 90. The method of any preceding enumerated embodiment wherein, upon cessation of the treatment, the individual's serum bicarbonate value decreases by at least 1 mEq/l within 1 month of the cessation of treatment.

Embodiment 91. The method of any preceding enumerated embodiment wherein, upon cessation of the treatment, the individual's serum bicarbonate value decreases by at least 1 mEq/l within 3 weeks of the cessation of treatment.

Embodiment 92. The method of any preceding enumerated embodiment wherein, upon cessation of the treatment, the individual's serum bicarbonate value decreases by at least 1 mEq/l within 2 weeks of the cessation of treatment.

Embodiment 93. The method of any preceding enumerated embodiment wherein, upon cessation of the treatment, the individual's serum bicarbonate value decreases by at least 1.5 mEq/l within 1 month of the cessation of treatment.

Embodiment 94. The method of any preceding enumerated embodiment wherein, upon cessation of the treatment, the individual's serum bicarbonate value decreases by at least 1.5 mEq/l within 3 weeks of the cessation of treatment.

Embodiment 95. The method of any preceding enumerated embodiment wherein, upon cessation of the treatment, the individual's serum bicarbonate value decreases by at least 1.5 mEq/l within 2 weeks of the cessation of treatment.

Embodiment 96. The method of any preceding enumerated embodiment wherein, upon cessation of the treatment, the individual's serum bicarbonate value decreases by at least 2 mEq/l within 1 month of the cessation of treatment.

Embodiment 97. The method of any preceding enumerated embodiment wherein, upon cessation of the treatment, the individual's serum bicarbonate value decreases by at least 2 mEq/l within 3 weeks of the cessation of treatment.

Embodiment 98. The method of any preceding enumerated embodiment wherein, upon cessation of the treatment, the individual's serum bicarbonate value decreases by at least 2 mEq/l within 2 weeks of the cessation of treatment.

Embodiment 99. The method of any preceding enumerated embodiment wherein, upon cessation of the treatment, the individual's serum bicarbonate value decreases by at least 2.5 mEq/l within 1 month of the cessation of treatment.

Embodiment 100. The method of any preceding enumerated embodiment wherein, upon cessation of the treatment, the individual's serum bicarbonate value decreases by at least 2.5 mEq/l within 3 weeks of the cessation of treatment.

Embodiment 101. The method of any preceding enumerated embodiment wherein, upon cessation of the treatment, the individual's serum bicarbonate value decreases by at least 2.5 mEq/l within 2 weeks of the cessation of treatment.

Embodiment 102. The method of any preceding enumerated embodiment wherein, upon cessation of the treatment, the individual's serum bicarbonate value decreases by at least 3 mEq/l within 1 month of the cessation of treatment.

Embodiment 103. The method of any preceding enumerated embodiment wherein, upon cessation of the treatment, the individual's serum bicarbonate value decreases by at least 3 mEq/l within 3 weeks of the cessation of treatment.

Embodiment 104. The method of any preceding enumerated embodiment wherein, upon cessation of the treatment, the individual's serum bicarbonate value decreases by at least 3 mEq/l within 2 weeks of the cessation of treatment.

Embodiment 105. The method of any preceding enumerated embodiment wherein, upon cessation of the treatment, the individual's serum bicarbonate value decreases by at least 3.5 mEq/l within 1 month of the cessation of treatment.

Embodiment 106. The method of any preceding enumerated embodiment wherein, upon cessation of the treatment, the individual's serum bicarbonate value decreases by at least 3.5 mEq/l within 3 weeks of the cessation of treatment.

Embodiment 107. The method of any preceding enumerated embodiment wherein, upon cessation of the treatment, the individual's serum bicarbonate value decreases by at least 3.5 mEq/l within 2 weeks of the cessation of treatment.

Embodiment 108. The method of any preceding enumerated embodiment wherein, upon cessation of the treatment, the individual's serum bicarbonate value decreases by at least 4 mEq/l within 1 month of the cessation of treatment.

Embodiment 109. The method of any preceding enumerated embodiment wherein, upon cessation of the treatment, the individual's serum bicarbonate value decreases by at least 4 mEq/l within 3 weeks of the cessation of treatment.

Embodiment 110. The method of any preceding enumerated embodiment wherein, upon cessation of the treatment, the individual's serum bicarbonate value decreases by at least 4 mEq/l within 2 weeks of the cessation of treatment.

Embodiment 111. The method of any preceding enumerated embodiment wherein, upon cessation of the treatment, the individual's serum bicarbonate value decreases by at least 4.5 mEq/l within 1 month of the cessation of treatment.

Embodiment 112. The method of any preceding enumerated embodiment wherein, upon cessation of the treatment, the individual's serum bicarbonate value decreases by at least 4.5 mEq/l within 3 weeks of the cessation of treatment.

Embodiment 113. The method of any preceding enumerated embodiment wherein, upon cessation of the treatment, the individual's serum bicarbonate value decreases by at least 4.5 mEq/l within 2 weeks of the cessation of treatment.

Embodiment 114. The method of any preceding enumerated embodiment wherein, upon cessation of the treatment, the individual's serum bicarbonate value decreases by at least 5 mEq/l within 1 month of the cessation of treatment.

Embodiment 115. The method of any preceding enumerated embodiment wherein, upon cessation of the treatment, the individual's serum bicarbonate value decreases by at least 5 mEq/l within 3 weeks of the cessation of treatment.

Embodiment 116. The method of any preceding enumerated embodiment wherein, upon cessation of the treatment, the individual's serum bicarbonate value decreases by at least 5 mEq/l within 2 weeks of the cessation of treatment.

Embodiment 117. The method of any preceding enumerated embodiment wherein the baseline serum bicarbonate value is the value of the serum bicarbonate concentration determined at a single time point.

Embodiment 118. The method of any of embodiments 1 to 116 wherein the baseline serum bicarbonate value is the mean value of at least two serum bicarbonate concentrations determined at different time-points.

Embodiment 119. The method of any of embodiments 1 to 116 wherein the baseline serum bicarbonate value is the mean value of at least two serum bicarbonate concentrations for serum samples drawn on different days.

Embodiment 120. The method of embodiment 119 wherein the baseline serum bicarbonate value is the mean value of at least two serum bicarbonate concentrations for serum samples drawn on consecutive days.

Embodiment 121. The method of embodiment 119 wherein the baseline serum bicarbonate value is the mean value of at least two serum bicarbonate concentrations for serum samples drawn on two consecutive days and prior to the initiation of the treatment.

Embodiment 122. The method of embodiment 119 wherein the baseline serum bicarbonate value is the mean or median value of at least two serum bicarbonate concentrations for serum samples drawn on non-consecutive days.

Embodiment 123. The method of embodiment 122 wherein the non-consecutive days are separated by at least two days.

Embodiment 124. The method of embodiment 122 wherein the non-consecutive days are separated by at least one week.

Embodiment 125. The method of embodiment 122 wherein the non-consecutive days are separated by at least two weeks.

Embodiment 126. The method of embodiment 122 wherein the non-consecutive days are separated by at least three weeks.

Embodiment 127. The method of any preceding enumerated embodiment wherein the individual is being treated for acute metabolic acidosis.

Embodiment 128258. The method of any preceding enumerated embodiment wherein the individual is being treated for chronic metabolic acidosis.

Embodiment 129. The method of any preceding enumerated embodiment wherein the daily dose has the capacity to remove at least 7.5 mEq each of protons and chloride ions as it transits the digestive system.

Embodiment 130. The method of any preceding enumerated embodiment wherein the daily dose has the capacity to remove at least 10 mEq each of protons and chloride ions as it transits the digestive system.

Embodiment 131. The method of any preceding enumerated embodiment wherein the daily dose has the capacity to remove at least 15 mEq each of protons and chloride ions as it transits the digestive system.

Embodiment 132. The method of any preceding enumerated embodiment wherein the daily dose has the capacity to remove at least 20 mEq each of protons and chloride ions as it transits the digestive system.

Embodiment 133. The method of any preceding enumerated embodiment wherein the daily dose has the capacity to remove at least 25 mEq each of protons and chloride ions as it transits the digestive system.

Embodiment 134. The method of any preceding enumerated embodiment wherein the daily dose has the capacity to remove at least 30 mEq each of protons and chloride ions as it transits the digestive system.

Embodiment 135. The method of any preceding enumerated embodiment wherein the daily dose has the capacity to remove at least 35 mEq each of protons and chloride ions as it transits the digestive system.

Embodiment 136. The method of any preceding enumerated embodiment wherein the daily dose has the capacity to remove at least 40 mEq each of protons and chloride ions as it transits the digestive system.

Embodiment 137. The method of any preceding enumerated embodiment wherein the daily dose has the capacity to remove at least 45 mEq each of protons and chloride ions as it transits the digestive system.

Embodiment 138. The method of any preceding enumerated embodiment wherein the daily dose has the capacity to remove at least 50 mEq each of protons and chloride ions as it transits the digestive system.

Embodiment 139. The method of any preceding enumerated embodiment wherein the daily dose is no more than 100 g/day.

Embodiment 140. The method of any preceding enumerated embodiment wherein the daily dose is less than 50 g/day.

Embodiment 141. The method of any preceding enumerated embodiment wherein the daily dose is less than 40 g/day.

Embodiment 142. The method of any preceding enumerated embodiment wherein the daily dose is less than 30 g/day.

Embodiment 143. The method of any preceding enumerated embodiment wherein the daily dose is less than 25 g/day.

Embodiment 144. The method of any preceding enumerated embodiment wherein the daily dose is less than 20 g/day.

Embodiment 145. The method of any preceding enumerated embodiment wherein the daily dose is less than 15 g/day.

Embodiment 146. The method of any preceding enumerated embodiment wherein the daily dose is less than 10 g/day.

Embodiment 147. The method of any preceding enumerated embodiment wherein the daily dose is less than 5 g/day.

Embodiment 148. The method of any preceding enumerated embodiment wherein the individual is treated for at least one day.

Embodiment 149. The method of any preceding enumerated embodiment wherein the individual is treated for at least one week.

Embodiment 150. The method of any preceding enumerated embodiment wherein the individual is treated for at least one month.

Embodiment 151. The method of any preceding enumerated embodiment wherein the individual is treated for at least several months.

Embodiment 152. The method of any preceding enumerated embodiment wherein the individual is treated for at least six months.

Embodiment 153. The method of any preceding enumerated embodiment wherein the individual is treated for at least one year.

Embodiment 154. The method of any preceding enumerated embodiment wherein the pharmaceutical composition is a nonabsorbable composition comprising a population of particles having a median particle diameter size (volume distribution) of at least 3 microns.

Embodiment 155. The method of any preceding enumerated embodiment wherein the pharmaceutical composition is a nonabsorbable composition comprising a population of particles having a median particle diameter size (volume distribution) in the range of 5 to 1,000 microns.

Embodiment 156. The method of any preceding enumerated embodiment wherein the pharmaceutical composition is a nonabsorbable composition comprising a population of particles having a median particle diameter size (volume distribution) in the range of 5 to 500 microns.

Embodiment 157. The method of any preceding enumerated embodiment wherein the pharmaceutical composition is a nonabsorbable composition comprising a population of particles having a median particle diameter size (volume distribution) in the range of 10 to 400 microns.

Embodiment 158. The method of any preceding enumerated embodiment wherein the pharmaceutical composition is a nonabsorbable composition comprising a population of particles having a median particle diameter size (volume distribution) in the range of 10 to 300 microns.

Embodiment 159. The method of any preceding enumerated embodiment wherein the pharmaceutical composition is a nonabsorbable composition comprising a population of particles having a median particle diameter size (volume distribution) in the range of 20 to 250 microns.

Embodiment 160. The method of any preceding enumerated embodiment wherein the pharmaceutical composition is a nonabsorbable composition comprising a population of particles having a median particle diameter size (volume distribution) in the range of 30 to 250 microns.

Embodiment 161. The method of any preceding enumerated embodiment wherein the pharmaceutical composition is a nonabsorbable composition comprising a population of particles having a median particle diameter size (volume distribution) in the range of 40 to 180 microns.

Embodiment 162. The method of any preceding enumerated embodiment wherein the pharmaceutical composition is a nonabsorbable composition comprising a population of particles in which less than 7% of the particles in the population (volume distribution) have a diameter less than 10 microns.

Embodiment 163. The method of any preceding enumerated embodiment wherein the pharmaceutical composition is a nonabsorbable composition comprising a population of particles in which less than 5% of the particles in the particles in the population (volume distribution) have a diameter less than 10 microns.

Embodiment 164. The method of any preceding enumerated embodiment wherein the pharmaceutical composition is a nonabsorbable composition comprising a population of particles in which less than 2.5% of the particles in the particles in the population (volume distribution) have a diameter less than 10 microns.

Embodiment 165. The method of any preceding enumerated embodiment wherein the pharmaceutical composition is a nonabsorbable composition comprising a population of particles in which less than 1% of the particles in the particles in the population (volume distribution) have a diameter less than 10 microns.

Embodiment 166. The method of any preceding enumerated embodiment wherein the pharmaceutical composition is a nonabsorbable composition comprising a population of particles having a particle size range that is (i) large enough to avoid passive or active absorption through the GI tract and (ii) small enough to not cause grittiness or unpleasant mouth feel when ingested as a powder, suspension, gel, and/or tablet.

Embodiment 167. The method of any preceding enumerated embodiment wherein the pharmaceutical composition is a nonabsorbable composition comprising a population of particles have a Swelling Ratio of less than 9.

Embodiment 168. The method of any preceding enumerated embodiment wherein the pharmaceutical composition is a nonabsorbable composition comprising a population of particles have a Swelling Ratio of less than 5.

Embodiment 169. The method of any preceding enumerated embodiment wherein the pharmaceutical composition is a nonabsorbable composition comprising a population of particles have a Swelling Ratio of less than 2.

Embodiment 170. The method of any preceding enumerated embodiment wherein the nonabsorbable composition has a theoretical binding capacity for protons and chloride ions of at least about 0.5 mEq/g.

Embodiment 171. The method of any preceding enumerated embodiment wherein the nonabsorbable composition has a theoretical binding capacity for protons and chloride ions of at least about 1 mEq/g.

Embodiment 172. The method of any preceding enumerated embodiment wherein the nonabsorbable composition has a theoretical binding capacity for protons and chloride ions of at least about 2 mEq/g.

Embodiment 173. The method of any preceding enumerated embodiment wherein the nonabsorbable composition has a theoretical binding capacity for protons and chloride ions of at least about 3 mEq/g.

Embodiment 174. The method of any preceding enumerated embodiment wherein the nonabsorbable composition has a theoretical binding capacity for protons and chloride ions of at least about 5 mEq/g.

Embodiment 175. The method of any preceding enumerated embodiment wherein the nonabsorbable composition has a theoretical binding capacity for protons and chloride ions of at least about 7.5 mEq/g.

Embodiment 176. The method of any preceding enumerated embodiment wherein the nonabsorbable composition has a theoretical binding capacity for protons and chloride ions of at least about 10 mEq/g.

Embodiment 177. The method of any preceding enumerated embodiment wherein the nonabsorbable composition has a theoretical binding capacity for protons and chloride ions of at least about 15 mEq/g.

Embodiment 178. The method of any preceding enumerated embodiment wherein the nonabsorbable composition has a theoretical binding capacity for protons and chloride ions of at least about 20 mEq/g.

Embodiment 179. The method of any preceding enumerated embodiment wherein the nonabsorbable composition has a theoretical binding capacity for protons and chloride ions of at least about 25 mEq/g.

Embodiment 180. The method of any preceding enumerated embodiment wherein the nonabsorbable composition has a theoretical binding capacity for protons and chloride ions in the range of 2 to 25 mEq/g.

Embodiment 181. The method of any preceding enumerated embodiment wherein the nonabsorbable composition has a theoretical binding capacity for the protons and chloride ions in the range of 5 to 25 mEq/g.

Embodiment 182. The method of any preceding enumerated embodiment wherein the nonabsorbable composition has a theoretical binding capacity for protons and chloride ions in the range of 10 to 25 mEq/g.

Embodiment 183. The method of any preceding enumerated embodiment wherein the nonabsorbable composition has a theoretical binding capacity for protons and chloride ions in the range of 5 to 20 mEq/g.

Embodiment 184. The method of any preceding enumerated embodiment wherein the nonabsorbable composition has a theoretical binding capacity for protons and chloride ions in the range of 7.5 to 20 mEq/g.

Embodiment 185. The method of any preceding enumerated embodiment wherein the nonabsorbable composition has a theoretical binding capacity for protons and chloride ions in the range of 10 to 20 mEq/g.

Embodiment 186. The method of any preceding enumerated embodiment wherein the theoretical binding capacity for protons and chloride ions is the theoretical binding capacity as determined in a SGF assay.

Embodiment 187. The method of any preceding enumerated embodiment wherein the nonabsorbable composition is characterized by a chloride ion binding capacity of at least 1 mEq/g in a SIB assay.

Embodiment 188. The method of any preceding enumerated embodiment wherein the nonabsorbable composition is characterized by a chloride ion binding capacity of at least 1.5 mEq/g in a SIB assay.

Embodiment 189. The method of any preceding enumerated embodiment wherein the nonabsorbable composition is characterized by a chloride ion binding capacity of at least 2 mEq/g in a SIB assay.

Embodiment 190. The method of any preceding enumerated embodiment wherein the nonabsorbable composition is characterized by a chloride ion binding capacity of at least 2.5 mEq/g in a SIB assay.

Embodiment 191. The method of any preceding enumerated embodiment wherein the nonabsorbable composition is characterized by a chloride ion binding capacity of at least 3 mEq/g in a SIB assay.

Embodiment 192. The method of any preceding enumerated embodiment wherein the nonabsorbable composition is characterized by a chloride ion binding capacity of at least 3.5 mEq/g in a SIB assay.

Embodiment 193. The method of any preceding enumerated embodiment wherein the nonabsorbable composition is characterized by a chloride ion binding capacity of at least 4 mEq/g in a SIB assay.

Embodiment 194. The method of any preceding enumerated embodiment wherein the nonabsorbable composition is characterized by a chloride ion binding capacity of at least 4.5 mEq/g in a SIB assay.

Embodiment 195. The method of any preceding enumerated embodiment wherein the nonabsorbable composition is characterized by a chloride ion binding capacity of at least 5 mEq/g in a SIB assay.

Embodiment 196. The method of any preceding enumerated embodiment wherein the ratio of the amount of bound chloride to bound phosphate in a SIB assay is at least 0.1:1, respectively.

Embodiment 197. The method of any preceding enumerated embodiment wherein the ratio of the amount of bound chloride to bound phosphate in a SIB assay is at least 0.3:1, respectively.

Embodiment 198. The method of any preceding enumerated embodiment wherein the ratio of the amount of bound chloride to bound phosphate in a SIB assay is at least 0.35:1, respectively.

Embodiment 199. The method of any preceding enumerated embodiment wherein the ratio of the amount of bound chloride to bound phosphate in a SIB assay is at least 0.4:1, respectively.

Embodiment 200. The method of any preceding enumerated embodiment wherein the ratio of the amount of bound chloride to bound phosphate in a SIB assay is at least 0.45:1, respectively.

Embodiment 201. The method of any preceding enumerated embodiment wherein the ratio of the amount of bound chloride to bound phosphate in a SIB assay is at least 0.5:1, respectively.

Embodiment 202. The method of any preceding enumerated embodiment wherein the ratio of the amount of bound chloride to bound phosphate in a SIB assay is at least 0.75:1, respectively.

Embodiment 203. The method of any preceding enumerated embodiment wherein the ratio of the amount of bound chloride to bound phosphate in a SIB assay is at least 1:1, respectively.

Embodiment 204. The method of any preceding enumerated embodiment wherein the ratio of the amount of bound chloride to bound phosphate in a SIB assay is at least 1.25:1, respectively.

Embodiment 205. The method of any preceding enumerated embodiment wherein the ratio of the amount of bound chloride to bound phosphate in a SIB assay is at least 1.5:1, respectively.

Embodiment 206. The method of any preceding enumerated embodiment wherein the ratio of the amount of bound chloride to bound phosphate in a SIB assay is at least 1.75:1, respectively.

Embodiment 207. The method of any preceding enumerated embodiment wherein the ratio of the amount of bound chloride to bound phosphate in a SIB assay is at least 2:1, respectively.

Embodiment 208. The method of any preceding enumerated embodiment wherein the ratio of the amount of bound chloride to bound phosphate in a SIB assay is at least 2.5:1, respectively.

Embodiment 209. The method of any preceding enumerated embodiment wherein the ratio of the amount of bound chloride to bound phosphate in a SIB assay is at least 3:1, respectively.

Embodiment 210. The method of any preceding enumerated embodiment wherein the ratio of the amount of bound chloride to bound phosphate in a SIB assay is at least 4:1, respectively.

Embodiment 211. The method of any preceding enumerated embodiment wherein the ratio of the amount of bound chloride to bound phosphate in a SIB assay is at least 5:1, respectively.

Embodiment 212. The method of any preceding enumerated embodiment wherein the daily dose has the capacity to remove at least about 5 mEq/day of each of protons and chloride ions.

Embodiment 213. The method of any preceding enumerated embodiment wherein the daily dose has the capacity to remove at least about 7 mEq/day each of protons and chloride ions.

Embodiment 214. The method of any preceding enumerated embodiment wherein the daily dose has the capacity to remove at least about 10 mEq/day of each of protons and chloride ions.

Embodiment 215. The method of any preceding enumerated embodiment wherein the daily dose has the capacity to remove at least about 15 mEq/day of each of protons and chloride ions.

Embodiment 216. The method of any preceding enumerated embodiment wherein the daily dose has the capacity to remove at least about 20 mEq/day of each of protons and chloride ions.

Embodiment 217. The method of any preceding enumerated embodiment wherein the daily dose has the capacity to remove at least about 25 mEq/day of each of protons and chloride ions.

Embodiment 218. The method of any preceding enumerated embodiment wherein the daily dose has the capacity to remove at least about 30 mEq/day of each of protons and chloride ions.

Embodiment 219. The method of any preceding enumerated embodiment wherein the daily dose has the capacity to remove at least about 35 mEq/day of each of protons and chloride ions.

Embodiment 220. The method of any preceding enumerated embodiment wherein the daily dose has the capacity to remove at least about 40 mEq/day of each of protons and chloride ions.

Embodiment 221. The method of any preceding enumerated embodiment wherein the daily dose has the capacity to remove at least about 45 mEq/day of each of protons and chloride ions.

Embodiment 222. The method of any preceding enumerated embodiment wherein the daily dose has the capacity to remove at least about 50 mEq/day of each of protons and chloride ions.

Embodiment 223. The method of any preceding enumerated embodiment wherein the daily dose removes less than 60 mEq/day of each of protons and chloride ions.

Embodiment 224. The method of any preceding enumerated embodiment wherein the daily dose removes less than 55 mEq/day of each of protons and chloride ions.

Embodiment 225. The method of any of embodiments 1 to 221 wherein the daily dose removes less than 50 mEq/day of the target species.

Embodiment 226. The method of any of embodiments 1 to 220 wherein the daily dose removes less than 45 mEq/day of each of protons and chloride ions.

Embodiment 227. The method of any of embodiments 1 to 219 wherein the daily dose removes less than 40 mEq/day of the target species.

Embodiment 228. The method of any of embodiments 1 to 218 wherein the daily dose removes less than 35 mEq/day of the target species.

Embodiment 229. The method of any of embodiments 1 to 217 wherein the daily dose removes less than 30 mEq/day of the target species.

Embodiment 230. The method of any of embodiments 1 to 216 wherein the daily dose removes less than 25 mEq/day of the target species.

Embodiment 231. The method of any of embodiments 1 to 215 wherein the daily dose removes less than 20 mEq/day of the target species.

Embodiment 232. The method of any of embodiments 1 to 214 wherein the daily dose removes less than 15 mEq/day of each of protons and chloride ions.

Embodiment 233. The method of any of embodiments 1 to 213 wherein the daily dose removes less than 10 mEq/day of each of protons and chloride ions.

Embodiment 234. The method of any preceding enumerated embodiment wherein the pharmaceutical composition contains exchangeable sodium ions and the composition contains less than 0.1% by weight sodium.

Embodiment 235. The method of any preceding enumerated embodiment wherein the pharmaceutical composition contains exchangeable sodium ions and the composition contains less than 0.01% by weight sodium.

Embodiment 236. The method of any preceding enumerated embodiment wherein the pharmaceutical composition is an anion exchange material comprising an insoluble (in the gastric environment) support structure and exchangeable anions.

Embodiment 237. The method of any preceding enumerated embodiment wherein the pharmaceutical composition is an anion exchange material comprising an insoluble (in the gastric environment) support structure and exchangeable anions and the anion exchange material is organic, inorganic, or a composite thereof.

Embodiment 238. The method of any preceding enumerated embodiment wherein the pharmaceutical composition is a strongly basic anion exchange material.

Embodiment 239. The method of any preceding enumerated embodiment wherein the pharmaceutical composition is a weakly basic anion exchange material.

Embodiment 240. The method of any preceding enumerated embodiment wherein the pharmaceutical composition is an anion exchange material comprising at least 1 mEq/g of an anion selected from the group consisting of hydroxide, carbonate, citrate or other bicarbonate equivalent anion, or a combination thereof.

Embodiment 241. The method of any preceding enumerated embodiment wherein the pharmaceutical composition is an anion exchange material comprising at least 2 mEq/g of an anion selected from the group consisting of hydroxide, carbonate, citrate or other bicarbonate equivalent anion.

Embodiment 242. The method of any preceding enumerated embodiment wherein the pharmaceutical composition is an anion exchange material comprising at least 5 mEq/g of an anion selected from the group consisting of hydroxide, carbonate, citrate or other bicarbonate equivalent anion.

Embodiment 243. The method of any preceding enumerated embodiment wherein the pharmaceutical composition is an anion exchange material comprising at least 10 mEq/g of an anion selected from the group consisting of hydroxide, carbonate, citrate or other bicarbonate equivalent anion.

Embodiment 244. The method of any of embodiments 1 to 242 wherein the pharmaceutical composition is an anion exchange material comprising less than 10 mEq/g of an anion selected from the group consisting of hydroxide, carbonate, citrate or other bicarbonate equivalent anion, or a combination thereof.

Embodiment 245. The method of any of embodiments 1 to 241 wherein the pharmaceutical composition is an anion exchange material comprising less than 5 mEq/g of an anion selected from the group consisting of hydroxide, carbonate, citrate or other bicarbonate equivalent anion.

Embodiment 246. The method of any of embodiments 1 to 241 wherein the pharmaceutical composition is an anion exchange material comprising less than 2.5 mEq/g of an anion selected from the group consisting of hydroxide, carbonate, citrate or other bicarbonate equivalent anion.

Embodiment 247. The method of any of embodiments 1 to 239 wherein the pharmaceutical composition is an anion exchange material comprising less than 1 mEq/g of an anion selected from the group consisting of hydroxide, carbonate, citrate or other bicarbonate equivalent anion.

Embodiment 248. The method of any of embodiments 240 to 247 wherein the bicarbonate equivalent anion is selected from the group consisting of acetate, lactate and the conjugate bases of other short chain carboxylic acids.

Embodiment 249. The method of any preceding enumerated embodiment wherein the pharmaceutical composition is an amphoteric ion exchange resin.

Embodiment 250. The method of any preceding enumerated embodiment wherein the pharmaceutical composition is a neutral composition having the capacity to bind both protons and chloride ions selected from the group consisting of polymers functionalized with propylene oxide, polymers functionalized with Michael acceptors, expanded porphyrins, covalent organic frameworks, and polymers containing amine and/or phosphine functional groups.

Embodiment 251. The method of any preceding enumerated embodiment wherein the pharmaceutical composition (i) removes more chloride ions than bicarbonate equivalent anions (ii) removes more chloride ions than phosphate anions, and (iii) removes more chloride ions than the conjugate bases of bile and fatty acids.

Embodiment 252. The method of any preceding enumerated embodiment wherein the treatment with the pharmaceutical composition does not have a clinically significant impact upon the serum or colon levels of a metabolically relevant species.

Embodiment 253. The method of any preceding enumerated embodiment wherein the treatment with the pharmaceutical composition does not have a clinically significant impact upon the serum or colon levels of a metabolically relevant cationic species.

Embodiment 254. The method of any preceding enumerated embodiment wherein the treatment with the pharmaceutical composition does not have a clinically significant impact upon the serum or colon levels of a metabolically relevant anionic species.

Embodiment 255. The method of any preceding enumerated embodiment wherein the treatment with the pharmaceutical composition does not have a clinically significant impact upon the serum potassium levels of a statistically significant number of individuals.

Embodiment 256. The method of any preceding enumerated embodiment wherein the treatment with the pharmaceutical composition does not have a clinically significant impact upon the serum phosphate levels of a statistically significant number of individuals.

Embodiment 257. The method of any preceding enumerated embodiment wherein the treatment with the pharmaceutical composition does not have a clinically significant impact upon the serum low density lipoprotein (LDL) levels of a statistically significant number of individuals.

Embodiment 258. The method of any preceding enumerated embodiment wherein the pharmaceutical composition is a nonabsorbable composition comprising a proton-binding, crosslinked amine polymer comprising the residue of an amine corresponding to Formula 1:

Formula 1

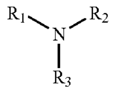

wherein $R_1$, $R_2$ and $R_3$ are independently hydrogen, hydrocarbyl, or substituted hydrocarbyl provided, however, at least one of $R_1$, $R_2$ and $R_3$ is other than hydrogen.

Embodiment 259. The method of any preceding enumerated embodiment wherein the pharmaceutical composition is a nonabsorbable composition comprising a proton-binding, crosslinked amine polymer comprising the residue of an amine corresponding to Formula 1:

Formula 1

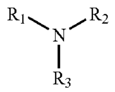

wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

Embodiment 260. The method of any preceding enumerated embodiment wherein the pharmaceutical composition is a nonabsorbable composition comprising the residue of an amine corresponding to Formula 1:

Formula 1

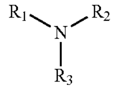

wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein the interfering ions are phosphate ions and the interfering ion buffer is a buffered solution at pH 5.5 of 36 mM chloride and 20 mM phosphate.

Embodiment 261. The method of any preceding enumerated embodiment wherein the pharmaceutical composition has an equilibrium chloride binding capacity of at least 7.5 mmol/g in an aqueous simulated gastric fluid buffer ("SGF") containing 35 mM NaCl and 63 mM HCl at pH 1.2 and 37° C.

Embodiment 262. The method of any preceding enumerated embodiment wherein the pharmaceutical composition has an equilibrium chloride binding capacity of at least 10 mmol/g in an aqueous simulated gastric fluid buffer ("SGF") containing 35 mM NaCl and 63 mM HCl at pH 1.2 and 37° C.

Embodiment 263. The method of any of embodiments 258 to 262 wherein $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ is not hydrogen.

Embodiment 264. The method of any of embodiments 258 to 262 wherein $R_1$, $R_2$ and $R_3$ are independently hydrogen, aliphatic or heteroaliphatic provided, however, at least one of $R_1$, $R_2$ and $R_3$ is other than hydrogen.

Embodiment 247. The method of any of embodiments 258 to 264 wherein the crosslinked amine polymer is prepared by substitution polymerization of the amine with a polyfunctional crosslinker, optionally also comprising amine moieties.

Embodiment 248. The method of any of embodiments 258 to 247 wherein the crosslinked amine polymer comprises the residue of an amine corresponding to Formula 1a and the crosslinked amine polymer is prepared by radical polymerization of an amine corresponding to Formula 1a:

Formula 1a

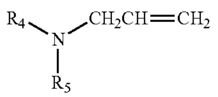

wherein $R_4$ and $R_5$ are independently hydrogen, hydrocarbyl, or substituted hydrocarbyl.

Embodiment 249. The method of embodiment 248 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 250. The method of embodiment 248 wherein $R_4$ and $R_5$ are independently hydrogen, aliphatic or heteroaliphatic.

Embodiment 251. The method of any preceding enumerated embodiment wherein the pharmaceutical composition is a nonabsorbable composition comprising a crosslinked amine polymer containing the residue of an amine corresponding to Formula 1b and the crosslinked amine polymer is prepared by substitution polymerization of the amine corresponding to Formula 1b with a polyfunctional crosslinker:

Fromula 1b

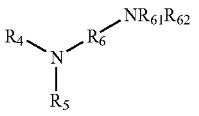

wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic.

Embodiment 252. The method of embodiment 251 wherein $R_4$ and $R_5$ are independently hydrogen, saturated hydrocarbon, unsaturated aliphatic, aryl, heteroaryl, heteroalkyl, or unsaturated heteroaliphatic.

Embodiment 253. The method of embodiment 251 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 254. The method of embodiment 251 wherein $R_4$ and $R_5$ are independently hydrogen, allyl, or aminoalkyl.

Embodiment 255. The method of any previous embodiment wherein the pharmaceutical composition is a polymer comprising a structure corresponding to Formula 4:

Formula 4

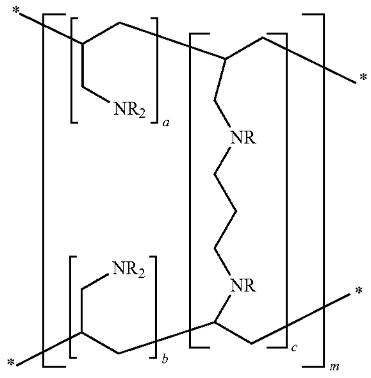

wherein each R is independently hydrogen or an ethylene crosslink between two nitrogen atoms of the crosslinked amine polymer

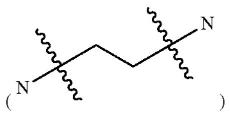

and a, b, and c are integers.

Embodiment 256. The method of embodiment 255 wherein a ratio of the sum of a and b to c (i.e., a+b:c) is in the range of about 1:1 to 5:1.

Embodiment 257. The method of embodiment 255 wherein a ratio of the sum of a and b to c (i.e., a+b:c) is in the range of about 1.5:1 to 4:1.

Embodiment 258. The method of embodiment 255 wherein a ratio of the sum of a and b to c (i.e., a+b:c) is in the range of about 1.75:1 to 3:1.

Embodiment 259. The method of embodiment 255 wherein a ratio of the sum of a and b to c (i.e., a+b:c) is in the range of about 2:1 to 2.5:1.

Embodiment 260. The method of any of embodiments 255 to 259 wherein the polymer has a carbon to nitrogen ratio of 2.5:1 to 5:1.

Embodiment 261. The method of any of embodiments 255 to 259 wherein the polymer has a carbon to nitrogen ratio of 3:1 to 4:1.

Embodiment 262. The method of any of embodiments 255 to 259 wherein the polymer has a carbon to nitrogen ratio of 3:5:1 to 3.9:1.

Embodiment 263. The method of any of embodiments 255 to 259 wherein the polymer has a carbon to nitrogen ratio of 3:7:1 to 3.9:1.

Embodiment 264. The method of any of embodiments 255 to 263 wherein 35-95% of the R substituents are hydrogen and 5-65% are an ethylene crosslink between two nitrogens of the crosslinked amine polymer.

Embodiment 265. The method of any of embodiments 255 to 263 wherein 50-95% of the R substituents are hydrogen and 5-50% are an ethylene crosslink between two nitrogens of the crosslinked amine polymer.

Embodiment 266. The method of any of embodiments 255 to 263 wherein 55-85% of the R substituents are hydrogen and 15-45% are an ethylene crosslink between two nitrogens of the crosslinked amine polymer.

Embodiment 267. The method of any of embodiments 255 to 263 wherein 55-90% of the R substituents are hydrogen and 10-45% are an ethylene crosslink between two nitrogens of the crosslinked amine polymer.

Embodiment 268. The method of any of embodiments 255 to 263 wherein 60-90% of the R substituents are hydrogen and 10-40% are an ethylene crosslink between two nitrogens of the crosslinked amine polymer.

Embodiment 269. The method of any of embodiments 255 to 263 wherein 65-90% of the R substituents are hydrogen and 10-35% are an ethylene crosslink between two nitrogens of the crosslinked amine polymer.

Embodiment 270. The method of any of embodiments 255 to 263 wherein 70-90% of the R substituents are hydrogen and 10-30% are an ethylene crosslink between two nitrogens of the crosslinked amine polymer.

Embodiment 271. The method of any of embodiments 255 to 263 wherein 75-85% of the R substituents are hydrogen and 15-25% are an ethylene crosslink between two nitrogens of the crosslinked amine polymer.

Embodiment 272. The method of any of embodiments 255 to 263 wherein 80-85% of the R substituents are hydrogen and 15-20% are an ethylene crosslink between two nitrogens of the crosslinked amine polymer.

Embodiment 273. The method of any preceding enumerated embodiment wherein the pharmaceutical composition is in a dosage unit form.

Embodiment 274. The method of embodiment 273 wherein the dosage unit form is a capsule, tablet or sachet dosage form.

Embodiment 275. The method of any preceding enumerated embodiment wherein the pharmaceutical composition comprises a pharmaceutically acceptable carrier, excipient, or diluent.

Embodiment 276. The method of any preceding enumerated embodiment wherein the daily dose is administered once-a-day (QD).

Embodiment 277. The method of any preceding enumerated embodiment wherein the daily dose is administered twice-a-day (BID).

Embodiment 278. The method of any preceding enumerated embodiment wherein the daily dose is administered three times a day.

Embodiment 279. The method of any preceding enumerated embodiments wherein the daily dose is obtained from a pharmaceutical product comprising a sealed container and the nonabsorbable composition within the sealed container.

Embodiment 280. The method of embodiment 279 wherein the sealed container comprises a moisture barrier.

Embodiment 281. The method of embodiment 279 or 280 wherein the sealed container comprises an oxygen barrier.

Embodiment 282. The method of any of embodiments 279 to 281 wherein the sealed container is a sealed sachet.

Embodiment 283. The method of any of embodiments 279 to 281 wherein the sealed container comprises a multilayer laminate of an inner contact layer, an outer layer; and a barrier layer disposed between the contact layer and outer layer.

Embodiment 284. The method of any of embodiments 279 to 281 wherein the sealed container comprises a multilayer laminate of an inner contact layer, an outer layer; and an oxygen-barrier layer disposed between the contact layer and outer layer.

Embodiment 285. The method of any of embodiments 279 to 281 wherein the sealed container comprises a multilayer laminate of an inner contact layer, an outer layer; and a moisture-barrier layer disposed between the contact layer and outer layer.

Embodiment 286. The method of any of embodiments 279 to 281 wherein the sealed container comprises a multilayer laminate of an inner contact layer, an outer layer; and an oxygen-barrier layer and a moisture-barrier layer disposed between the contact layer and outer layer.

Embodiment 287. The method of any of embodiments 279 to 281 wherein the sealed container comprises a multilayer laminate of an inner contact layer, an outer layer; and an oxygen-scavenging layer disposed between the contact layer and the outer layer.

Embodiments 288-570. Intentionally omitted.

Embodiment 571. A composition for use in a method of treating metabolic acidosis in an adult human patient wherein in said treatment 0.1-12 g of said composition is administered to the patient per day, said composition being a nonabsorbable composition having the capacity to remove protons from the patient, wherein the nonabsorbable composition is characterized by a chloride ion binding capacity of at least 2.5 mEq/g in a Simulated Small Intestine Inorganic Buffer ("SIB") assay.

Embodiment 572. A composition for use in a method of treating metabolic acidosis in an adult human patient, said patient having a serum bicarbonate level of less than 20 mEq/L prior to treatment, said composition being a nonabsorbable composition having the capacity to remove protons from the patient.

Embodiment 573. The composition for use according to embodiment 571 or 572, wherein the patient's serum bicarbonate level is less than 19 mEq/L prior to treatment.

Embodiment 574. The composition for use according to embodiment 571 or 572, wherein the patient's serum bicarbonate level is less than 18 mEq/L prior to treatment.

Embodiment 575. The composition for use according to embodiment 571 or 572, wherein the patient's serum bicarbonate level is less than 17 mEq/L prior to treatment.

Embodiment 576. The composition for use according to embodiment 571 or 572, wherein the patient's serum bicarbonate level is less than 16 mEq/L prior to treatment.

Embodiment 577. The composition for use according to embodiment 571 or 572, wherein the patient's serum bicarbonate level is less than 15 mEq/L prior to treatment.

Embodiment 578. The composition for use according to embodiment 571 or 572, wherein the patient's serum bicarbonate level is less than 14 mEq/L prior to treatment.

Embodiment 579. The composition for use according to embodiment 571 or 572, wherein the patient's serum bicarbonate level is less than 13 mEq/L prior to treatment.

Embodiment 580. The composition for use according to embodiment 571 or 572, wherein the patient's serum bicarbonate level is less than 12 mEq/L prior to treatment.

Embodiment 581. The composition for use according to embodiment 571 or 572, wherein the patient's serum bicarbonate level is less than 11 mEq/L prior to treatment.

Embodiment 582. The composition for use according to embodiment 571 or 572, wherein the patient's serum bicarbonate level is less than 10 mEq/L prior to treatment.

Embodiment 583. The composition for use according to embodiment 571 to 582 wherein said patient's serum bicarbonate value is increased by at least 1 mEq/L over 15 days of treatment.

Embodiment 584. The composition of embodiment 571 to 583 wherein in said treatment 0.1-12 g of said polymer is administered to the patient per day.

Embodiment 585. The composition of any one of embodiments 571 to 584 wherein the nonabsorbable composition is characterized by a chloride ion binding capacity of at least 2.5 mEq/g in a Simulated Small Intestine Inorganic Buffer ("SIB") assay.

Embodiment 586. A composition for use in a method of treating metabolic acidosis in an adult human patient by increasing that patient's serum bicarbonate value by at least 1 mEq/L over 15 days of treatment, said composition being a nonabsorbable composition having the capacity to remove protons from the patient.

Embodiment 587. The composition of embodiment 571 to 586 wherein in said treatment 0.1-12 g of said polymer is administered to the patient per day.

Embodiment 588. The composition of any one of embodiments 572 to 587 wherein the nonabsorbable composition is characterized by a chloride ion binding capacity of at least 2.5 mEq/g in a Simulated Small Intestine Inorganic Buffer ("SIB") assay.

Embodiment 589. The composition according to any one of embodiments 586 to 588 wherein the patient's serum bicarbonate level value is increased by at least 1 mEq/L over 15 days of treatment.

Embodiment 590. The composition for use according to any one of embodiments 586 to 589, wherein the increase in serum bicarbonate level is at least 1.5 mEq/L.

Embodiment 591. The composition for use according to any one of embodiments 586 to 590, wherein the increase in serum bicarbonate level is at least 2 mEq/L.

Embodiment 592. The composition for use according to any one of embodiments 586 to 591, wherein the increase in serum bicarbonate level is at least 2.5 mEq/L.

Embodiment 593. The composition for use according to any one of embodiments 586 to 592, wherein the increase in serum bicarbonate level is at least 3 mEq/L.

Embodiment 594. The composition for use according to any one of embodiments 586 to 593, wherein the increase in serum bicarbonate level is at least 3.5 mEq/L.

Embodiment 595. The composition for use according to any one of embodiments 586 to 594, wherein the increase in serum bicarbonate level is at least 4 mEq/L.

Embodiment 596. The composition for use according to any one of embodiments 586 to 595, wherein the increase in serum bicarbonate level is at least 4.5 mEq/L.

Embodiment 597. The composition for use according to any one of embodiments 586 to 596, wherein the increase in serum bicarbonate level is at least 5 mEq/L.

Embodiment 598. The composition for use according to embodiment any one of embodiments 586 to 597, wherein the increase is observed during 14 days of treatment.

Embodiment 599. The composition for use according to embodiment any one of embodiments 586 to 598, wherein the increase is observed during 13 days of treatment.

Embodiment 600. The composition for use according to embodiment any one of embodiments 586 to 599, wherein the increase is observed during 12 days of treatment.

Embodiment 601. The composition for use according to embodiment any one of embodiments 586 to 600, wherein the increase is observed during 11 days of treatment.

Embodiment 602. The composition for use according to embodiment any one of embodiments 586 to 601, wherein the increase is observed during 10 days of treatment.

Embodiment 603. The composition for use according to embodiment any one of embodiments 586 to 602, wherein the increase is observed during 9 days of treatment.

Embodiment 604. The composition for use according to embodiment any one of embodiments 586 to 603, wherein the increase is observed during 8 days of treatment.

Embodiment 605. The composition for use according to embodiment any one of embodiments 586 to 604, wherein the increase is observed during 7 days of treatment.

Embodiment 606. The composition for use according to embodiment any one of embodiments 586 to 605, wherein the increase is observed during 6 days of treatment.

Embodiment 607. The composition for use according to embodiment any one of embodiments 586 to 606, wherein the increase is observed during 5 days of treatment.

Embodiment 608. The composition for use according to embodiment any one of embodiments 586 to 607, wherein the increase is observed during 4 days of treatment.

Embodiment 609. The composition for use according to embodiment any one of embodiments 586 to 608, wherein the increase is observed during 3 days of treatment.

Embodiment 610. The composition for use according to embodiment any one of embodiments 586 to 609, wherein the increase is observed during 2 days of treatment.

Embodiment 611. The composition for use according to embodiment any one of embodiments 586 to 610, wherein the increase is observed during 1 day of treatment.

Embodiment 612. The composition for use according to any one of embodiments 571 to 611 wherein the specified number of days of treatment are the first days of treatment with the composition.

Embodiment 613. The composition for use according to embodiment 572-601, wherein in said treatment 0.1-12 g of said polymer is administered to the patient per day.

Embodiment 614. The composition for use according to embodiment 613, wherein in said treatment 1-11 g of said polymer is administered to the patient per day.

Embodiment 615. The composition for use according to embodiment 613, wherein in said treatment 2-10 g of said polymer is administered to the patient per day.

Embodiment 616. The composition for use according to embodiment 613, wherein in said treatment 3-9 g of said polymer is administered to the patient per day.

Embodiment 617. The composition for use according to embodiment 613, wherein in said treatment 3-8 g of said polymer is administered to the patient per day.

Embodiment 618. The composition for use according to embodiment 613, wherein in said treatment 3-7 g of said polymer is administered to the patient per day.

Embodiment 619. The composition for use according to embodiment 613, wherein in said treatment 3-6 g of said polymer is administered to the patient per day.

Embodiment 620. The composition for use according to embodiment 613, wherein in said treatment 3.5-5.5 g of said polymer is administered to the patient per day.

Embodiment 621. The composition for use according to embodiment 613, wherein in said treatment 4-5 g of said polymer is administered to the patient per day.

Embodiment 622. The composition for use according to embodiment 613, wherein in said treatment 1-3 g of said polymer is administered to the patient per day.

Embodiment 623. The composition for use according to embodiment 571 or 572, wherein about 0.5 g of the composition is administered to the patient per day.

Embodiment 624. The composition for use according to embodiment 571 or 572, wherein about 1 g of the composition is administered to the patient per day.

Embodiment 625. The composition for use according to embodiment 571 or 572, wherein about 1.5 g of the composition is administered to the patient per day.

Embodiment 626. The composition for use according to embodiment 571 or 572, wherein about 2 g of the composition is administered to the patient per day.

Embodiment 627. The composition for use according to embodiment 571 or 572, wherein about 2.5 g of the composition is administered to the patient per day.

Embodiment 628. The composition for use according to embodiment 571 or 572, wherein about 3 g of the composition is administered to the patient per day.

Embodiment 629. The composition for use according to embodiment 571 or 572, wherein about 3.5 g of the composition is administered to the patient per day.

Embodiment 630. The composition for use according to embodiment 571 or 572, wherein about 4.0 g of the composition is administered to the patient per day.

Embodiment 631. The composition for use according to embodiment 571 or 572, wherein about 4.5 g of the composition is administered to the patient per day.

Embodiment 632. The composition for use according to embodiment 571 or 572, wherein about 5.0 g of the composition is administered to the patient per day.

Embodiment 633. The composition for use according to any one of embodiments 571 to 632, wherein the chloride ion binding capacity in a Simulated Small Intestine Inorganic Buffer ("SIB") assay is at least 3 mEq/g.

Embodiment 634. The composition for use according to any one of embodiments 571 to 633, wherein the chloride ion binding capacity in a Simulated Small Intestine Inorganic Buffer ("SIB") assay is at least 3.5 mEq/g.

Embodiment 635. The composition for use according to any one of embodiments 571 to 634, wherein the chloride ion binding capacity in a Simulated Small Intestine Inorganic Buffer ("SIB") assay is at least 4 mEq/g.

Embodiment 636. The composition for use according to any one of embodiments 571 to 635, wherein the chloride ion binding capacity in a Simulated Small Intestine Inorganic Buffer ("SIB") assay is at least 4.5 mEq/g.

Embodiment 637. The composition for use according to any one of embodiments 571 to 636, wherein the chloride ion binding capacity in a Simulated Small Intestine Inorganic Buffer ("SIB") assay is at least 5 mEq/g.

Embodiment 638. The composition for use according any one of embodiments 571 to 637, wherein the chloride ion binding capacity in a SIB assay is less than 10 mEq/g.

Embodiment 639. The composition for use according any one of embodiments 571 to 638, wherein the chloride ion binding capacity in a SIB assay is less than 9 mEq/g.

Embodiment 640. The composition for use according any one of embodiments 571 to 639, wherein the chloride ion binding capacity in a SIB assay is less than 8 mEq/g.

Embodiment 641. The composition for use according any one of embodiments 571 to 640, wherein the chloride ion binding capacity in a SIB assay is less than 7 mEq/g.

Embodiment 642. The composition for use according any one of embodiments 571 to 641, wherein the chloride ion binding capacity in a SIB assay is less than 6 mEq/g.

Embodiment 643. The composition for use according any one of embodiments 571 to 642, wherein the chloride ion binding capacity in a SIB assay is less than 5 mEq/g.

Embodiment 644. A composition for use in a method of treating metabolic acidosis in an adult human patient wherein in said treatment >12-100 g of said composition is administered to the patient per day, said composition being a nonabsorbable composition having the capacity to remove protons from the patient, wherein the nonabsorbable composition is characterized by a chloride ion binding capacity of less than 2.5 mEq/g in a Simulated Small Intestine Inorganic Buffer ("SIB") assay.

Embodiment 645. The composition according to embodiments 644 wherein the patient's serum bicarbonate value is increased by at least 1 mEq/L over 15 days of treatment.

Embodiment 646. A composition for use in a method of treating metabolic acidosis in an adult human patient by increasing that patient's serum bicarbonate value by at least 1 mEq/L over 15 days of treatment, wherein in said treatment >12-100 g of said polymer is administered to the patient per day, said composition being a nonabsorbable composition having the capacity to remove protons from the patient, wherein the nonabsorbable composition is characterized by a chloride ion binding capacity of at least 2.5 mEq/g in a Simulated Small Intestine Inorganic Buffer ("SIB") assay.

Embodiment 647. The composition for use according to embodiment 645 or 646, wherein the increase in serum bicarbonate level is at least 1 mEq/L.

Embodiment 648. The composition for use according to embodiment 645 or 646, wherein the increase in serum bicarbonate level is at least 1.5 mEq/L.

Embodiment 649. The composition for use according to embodiment 645 or 646, wherein the increase in serum bicarbonate level is at least 2 mEq/L.

Embodiment 650. The composition for use according to embodiment 645 or 646, wherein the increase in serum bicarbonate level is at least 2.5 mEq/L.

Embodiment 651. The composition for use according to embodiment 645 or 646, wherein the increase in serum bicarbonate level is at least 3 mEq/L.

Embodiment 652. The composition for use according to embodiment 645 or 646, wherein the increase in serum bicarbonate level is at least 3.5 mEq/L.

Embodiment 653. The composition for use according to embodiment 645 or 646, wherein the increase in serum bicarbonate level is at least 4 mEq/L.

Embodiment 654. The composition for use according to embodiment 645 or 646, wherein the increase in serum bicarbonate level is at least 4.5 mEq/L.

Embodiment 655. The composition for use according to embodiment 645 or 646, wherein the increase in serum bicarbonate level is at least 5 mEq/L.

Embodiment 656. The composition for use according to embodiment 645 or 646, wherein the increase is observed during 14 days of treatment.

Embodiment 657. The composition for use according to embodiment 645 or 646, wherein the increase is observed during 13 days of treatment.

Embodiment 658. The composition for use according to embodiment 645 or 646, wherein the increase is observed during 12 days of treatment.

Embodiment 659. The composition for use according to embodiment 645 or 646, wherein the increase is observed during 11 days of treatment.

Embodiment 660. The composition for use according to embodiment 645 or 646, wherein the increase is observed during 10 days of treatment.

Embodiment 661. The composition for use according to embodiment 645 or 646, wherein the increase is observed during 9 days of treatment.

Embodiment 662. The composition for use according to embodiment 645 or 646, wherein the increase is observed during 8 days of treatment.

Embodiment 663. The composition for use according to embodiment 645 or 646, wherein the increase is observed during 7 days of treatment.

Embodiment 664. The composition for use according to embodiment 645 or 646, wherein the increase is observed during 6 days of treatment.

Embodiment 665. The composition for use according to embodiment 645 or 646, wherein the increase is observed during 5 days of treatment.

Embodiment 666. The composition for use according to embodiment 645 or 646, wherein the increase is observed during 4 days of treatment.

Embodiment 667. The composition for use according to embodiment 645 or 646, wherein the increase is observed during 3 days of treatment.

Embodiment 668. The composition for use according to embodiment 645 or 646, wherein the increase is observed during 2 days of treatment.

Embodiment 669. The composition for use according to embodiment 645 or 646, wherein the increase is observed during 1 day of treatment.

Embodiment 670. The composition for use according to any one of embodiments 644 to 654 wherein the specified number of days of treatment are the first days of treatment with the composition.

Embodiment 671. A composition for use according to embodiment 644 to 670 wherein 12-100 g is administered to the patient per day.

Embodiment 672. A composition for use according to embodiment 644 to 671 wherein 20-90 g is administered to the patient per day.

Embodiment 673. A composition for use according to embodiment 644 to 672 wherein 20-80 g is administered to the patient per day.

Embodiment 674. A composition for use according to embodiment 644 to 673 wherein 20-70 g is administered to the patient per day.

Embodiment 675. A composition for use according to embodiment 644 to 674 wherein 20-60 g is administered to the patient per day.

Embodiment 676. A composition for use according to embodiment 644 to 675 wherein 20-50 g is administered to the patient per day.

Embodiment 677. A composition for use according to embodiment 644 to 676 wherein 20-40 g is administered to the patient per day.

Embodiment 678. A composition for use according to embodiment 644 to 677 wherein 20-35 g is administered to the patient per day.

Embodiment 679. A composition for use according to embodiment 644 to 678 wherein 20-30 g is administered to the patient per day.

Embodiment 680. A composition for use according to embodiment 644 to 679 wherein 20-25 g is administered to the patient per day.

Embodiment 681. The composition for use according to any one of embodiments 644 to 680, wherein the chloride ion binding capacity in a Simulated Small Intestine Inorganic Buffer ("SIB") assay is less than 2 mEq/g.

Embodiment 682. The composition for use according to any one of embodiments 644 to 681, wherein the chloride ion binding capacity in a Simulated Small Intestine Inorganic Buffer ("SIB") assay is less than 1.5 mEq/g.

Embodiment 683. The composition for use according to any one of embodiments 644 to 682, wherein the chloride ion binding capacity in a Simulated Small Intestine Inorganic Buffer ("SIB") assay is less than 1 mEq/g.

Embodiment 684. The composition for use according to any one of embodiments 644 to 683, wherein the chloride ion binding capacity in a Simulated Small Intestine Inorganic Buffer ("SIB") assay is less than 0.75 mEq/g.

Embodiment 685. The composition for use according to any one of embodiments 644 to 684, wherein the chloride ion binding capacity in a Simulated Small Intestine Inorganic Buffer ("SIB") assay is greater than 0.5 mEq/g.

Embodiment 686. The composition for use according to any one of embodiments 644 to 685, wherein the chloride ion binding capacity in a Simulated Small Intestine Inorganic Buffer ("SIB") assay is greater than 1 mEq/g.

Embodiment 687. The composition for use according to any one of embodiments 644 to 686, wherein the chloride ion binding capacity in a Simulated Small Intestine Inorganic Buffer ("SIB") assay is greater than 1.5 mEq/g.

Embodiment 688. The composition for use according to any one of embodiments 644 to 687, wherein the chloride ion binding capacity in a Simulated Small Intestine Inorganic Buffer ("SIB") assay is greater than 2 mEq/g.

Embodiment 689. The composition for use according to any preceeding embodiment wherein the composition is administered once per day in order to provide the total specified daily dose.

Embodiment 690. The composition for use according to any preceeding embodiment wherein the composition is administered twice per day in order to provide the total specified daily dose.

Embodiment 691. The composition for use according to any preceeding embodiment wherein the composition is administered three times per day in order to provide the total specified daily dose.

Embodiment 692. The composition for use according to any preceding enumerated embodiment wherein said composition is administered orally.

Embodiment 693. The composition for use according to any one of embodiments 571 to 692 wherein the composition is a pharmaceutical composition comprising a proton-binding, crosslinked amine polymer comprising the residue of an amine corresponding to Formula 1:

Formula 1

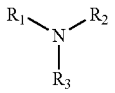

wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

Embodiment 694. The composition for use according to any one of embodiments 571 to 692 wherein the composition is a pharmaceutical composition comprising a proton-binding, crosslinked amine polymer comprising the residue of an amine corresponding to Formula 1:

Formula 1

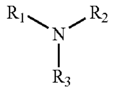

wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein the interfering ions are phosphate ions and the interfering ion buffer is a buffered solution at pH 5.5 of 36 mM chloride and 20 mM phosphate.

Embodiment 695. The composition for use according to any one of embodiments 571 to 692 wherein the composition is the pharmaceutical composition of embodiment 682 wherein the crosslinked amine polymer has an equilibrium chloride binding capacity of at least 7.5 mmol/g in an aqueous simulated gastric fluid buffer ("SGF") containing 35 mM NaCl and 63 mM HCl at pH 1.2 and 37° C.

Embodiment 696. The composition for use according to any one of embodiments 571 to 692 wherein the composition is the pharmaceutical composition of embodiment 682 wherein the crosslinked amine polymer has an equilibrium chloride binding capacity of at least 10 mmol/g in an aqueous simulated gastric fluid buffer ("SGF") containing 35 mM NaCl and 63 mM HCl at pH 1.2 and 37° C.

Embodiment 697. The composition for use according to any one of embodiments 571 to 692 wherein the composition is the pharmaceutical composition of embodiment 683 wherein the crosslinked amine polymer has an equilibrium swelling ratio in deionized water of about 4 or less.

Embodiment 698. The composition for use according to any one of embodiments 571 to 692 wherein the composition is the pharmaceutical composition of embodiment 683 wherein the crosslinked amine polymer has an equilibrium swelling ratio in deionized water of about 3 or less.

Embodiment 699. The composition for use according to any one of embodiments 571 to 692 wherein the composition is the pharmaceutical composition of embodiment 683 wherein the crosslinked amine polymer has an equilibrium swelling ratio in deionized water of about 2 or less.

Embodiment 700. The composition for use according to any one of embodiments 571 to 692 wherein the composition is the pharmaceutical composition of any preceding enumerated embodiment wherein $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ is not hydrogen.

Embodiment 701. The composition for use according to any one of embodiments 571 to 692 wherein the composition is the pharmaceutical composition of any preceding enumerated embodiment wherein $R_1$, $R_2$ and $R_3$ are independently hydrogen, aliphatic or heteroaliphatic provided, however, at least one of $R_1$, $R_2$ and $R_3$ is other than hydrogen.

Embodiment 702. The composition for use according to any one of embodiments 571 to 692 wherein the composition is the pharmaceutical composition of any preceding enumerated embodiment wherein the crosslinked amine polymer is prepared by substitution polymerization of the amine with a polyfunctional crosslinker, optionally also comprising amine moieties.

Embodiment 703. The composition for use according to any one of embodiments 571 to 692 wherein the composition is the pharmaceutical composition of any of embodiments 693 to 701 wherein the crosslinked amine polymer comprises the residue of an amine corresponding to Formula 1a and the crosslinked amine polymer is prepared by radical polymerization of an amine corresponding to Formula 1a:

Formula 1a

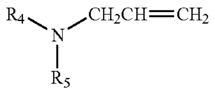

wherein $R_4$ and $R_5$ are independently hydrogen, hydrocarbyl, or substituted hydrocarbyl.

Embodiment 704. The composition for use according to any one of embodiments 571 to 692 wherein the composition is the pharmaceutical composition of embodiment 703 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 705. The composition for use according to any one of embodiments 571 to 692 wherein the composition is the pharmaceutical composition of embodiment 703 wherein $R_4$ and $R_5$ are independently hydrogen, aliphatic or heteroaliphatic.

Embodiment 706. The composition for use according to any one of embodiments 571 to 692 wherein the composition is the pharmaceutical composition of any of embodiments 693 to 701 wherein the crosslinked amine polymer comprises the residue of an amine corresponding to Formula 1b and the crosslinked amine polymer is prepared by substitution polymerization of the amine corresponding to Formula 1b with a polyfunctional crosslinker:

Formula 1b

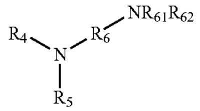

wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic.

Embodiment 707. The composition for use according to any one of embodiments 571 to 692 wherein the composition is the pharmaceutical composition of embodiment 706 wherein $R_4$ and $R_5$ are independently hydrogen, saturated hydrocarbon, unsaturated aliphatic, aryl, heteroaryl, heteroalkyl, or unsaturated heteroaliphatic.

Embodiment 708. The composition for use according to any one of embodiments 571 to 692 wherein the composition is the pharmaceutical composition of embodiment 706 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 709. The composition for use according to any one of embodiments 571 to 692 wherein the composition is the pharmaceutical composition of embodiment 706 wherein $R_4$ and $R_5$ are independently hydrogen, allyl, or aminoalkyl.

Embodiment 710. The composition for use according to any one of embodiments 571 to 692 wherein the composition is the pharmaceutical composition of any preceding enumerated embodiment wherein the crosslinked amine polymer comprises the residue of an amine corresponding to Formula 1c:

Formula 1c

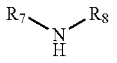

wherein $R_7$ is hydrogen, aliphatic or heteroaliphatic and Ra is aliphatic or heteroaliphatic.

Embodiment 711. The composition for use according to any one of embodiments 571 to 692 wherein the composition is the pharmaceutical composition of any of embodiments 693 to 701 wherein the crosslinked amine polymer comprises the residue of an amine corresponding to Formula 2:

Formula 2

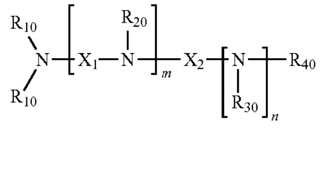

wherein m and n are independently non-negative integers;

$R_{10}$, $R_{20}$, $R_{30}$, and $R_{40}$ are independently hydrogen, hydrocarbyl, or substituted hydrocarbyl;

$X_1$ is

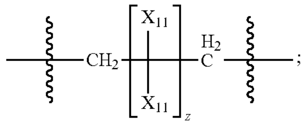

$X_2$ is hydrocarbyl or substituted hydrocarbyl;

each $X_{11}$ is independently hydrogen, hydrocarbyl, substituted hydrocarbyl, hydroxy, or amino; and z is a non-negative number.

Embodiment 712. The composition for use according to any one of embodiments 571 to 692 wherein the composition is the pharmaceutical composition of embodiment 711 wherein $R_{10}$, $R_{20}$, $R_{30}$, and $R_{40}$ are independently hydrogen, aliphatic, aryl, heteroaliphatic, or heteroaryl, m and z are independently 0-3 and n is 0 or 1.

Embodiment 713. The composition for use according to any one of embodiments 571 to 692 wherein the composition is the pharmaceutical composition of embodiment 711 or 712 wherein $X_2$ is aliphatic or heteroaliphatic.

Embodiment 714. The composition for use according to any one of embodiments 571 to 692 wherein the composition is the pharmaceutical composition of embodiment 711, 712 or 713 wherein m is 1-3 and $X_{11}$ is hydrogen, aliphatic or heteroaliphatic.

Embodiment 715. The composition for use according to any one of embodiments 571 to 692 wherein the composition is the pharmaceutical composition of any of embodiments 693 to 701 wherein the crosslinked amine polymer comprises the residue of an amine corresponding to Formula 2a:

Formula 2a

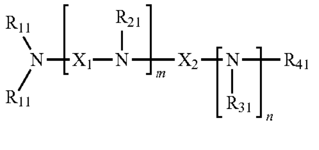

wherein m and n are independently non-negative integers;

each $R_{11}$ is independently hydrogen, hydrocarbyl, heteroaliphatic, or heteroaryl;

$R_{21}$ and $R_{31}$, are independently hydrogen or heteroaliphatic;

$R_{41}$ is hydrogen, substituted hydrocarbyl, or hydrocarbyl;

$X_1$ is

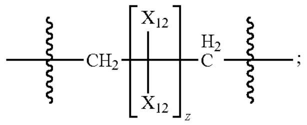

$X_2$ is alkyl or substituted hydrocarbyl;

each $X_{12}$ is independently hydrogen, hydroxy, amino, aminoalkyl, boronic acid or halo; and z is a non-negative number.

Embodiment 716. The composition for use according to any one of embodiments 571 to 692 wherein the composition is the pharmaceutical composition of embodiment 715 wherein m and z are independently 0-3 and n is 0 or 1.

Embodiment 717. The composition for use according to any one of embodiments 571 to 692 wherein the composition is the pharmaceutical composition of embodiment 715 or 716 wherein $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl.

Embodiment 718. The composition for use according to any one of embodiments 571 to 692 wherein the composition is the pharmaceutical composition of embodiment 715 or 716 wherein each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic.

Embodiment 719. The composition for use according to any one of embodiments 571 to 692 wherein the composition is the pharmaceutical composition of any of embodiments 693 to 701 wherein the crosslinked amine polymer comprises the residue of an amine corresponding to Formula 2b:

Formula 2b

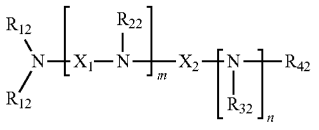

wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

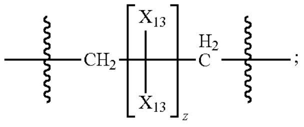

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

z is a non-negative number; and the amine corresponding to Formula 2b comprises at least one allyl group.

Embodiment 720. The composition for use according to any one of embodiments 571 to 692 wherein the composition is the pharmaceutical composition of embodiment 719 wherein m and z are independently 0-3 and n is 0 or 1.

Embodiment 721. The composition for use according to any one of embodiments 571 to 692 wherein the composition is the pharmaceutical composition of embodiment 719 or 720 wherein $R_{12}$ or $R_{42}$ independently comprise at least one allyl or vinyl moiety.

Embodiment 722. The composition for use according to any one of embodiments 571 to 692 wherein the composition is the pharmaceutical composition of embodiment 719 or 720 wherein (i) m is a positive integer and $R_{12}$, $R_{22}$ and $R_{42}$, in combination comprise at least two allyl or vinyl moieties or (ii) n is a positive integer and $R_{12}$, $R_{32}$ and $R_{42}$, in combination, comprise at least two allyl or vinyl moieties.

Embodiment 723. The composition for use according to any one of embodiments 571 to 692 wherein the composition is the pharmaceutical composition of embodiment 719 or 720 wherein the crosslinked amine polymer comprises the residue of an amine appearing in Table A.

Embodiment 724. The composition for use according to any one of embodiments 571 to 692 wherein the composition is the pharmaceutical composition of embodiment 719, 720 or 723 wherein the crosslinked amine polymer is crosslinked with a crosslinking agent appearing in Table B.

Embodiment 725. The composition for use according to any one of embodiments 571 to 692 wherein the composition is the pharmaceutical composition of any preceding enumerated embodiment wherein the crosslinked amine polymer comprises a repeat unit corresponding to Formula 3:

Formula 3

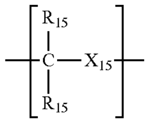

wherein $R_{15}$, $R_{16}$ and $R_{17}$ are independently hydrogen, hydrocarbyl, substituted hydrocarbyl, hydroxyl, amino, boronic acid or halo;

$X_{15}$ is

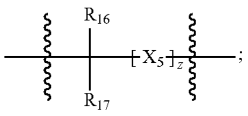

$X_5$ is hydrocarbyl, substituted hydrocarbyl, oxo (—O—), or amino; and z is a non-negative number.

Embodiment 726. The composition for use according to any one of embodiments 571 to 692 wherein the composition is the pharmaceutical composition of embodiment 725 wherein $R_{15}$, $R_{16}$ and $R_{17}$ are independently aliphatic or heteroaliphatic.

Embodiment 727. The composition for use according to any one of embodiments 571 to 692 wherein the composition is the pharmaceutical composition of embodiment 725 or 726 wherein $X_5$ is oxo, amino, alkylamino, ethereal, alkanol, or haloalkyl.

Embodiment 728. The composition for use according to any one of embodiments 571 to 692 wherein the composition is the pharmaceutical composition of any of embodiments 693 to 701 wherein the crosslinked amine polymer is prepared by (i) substitution polymerization of polyfunctional reagents at least one of which comprises amine moieties, (2) radical polymerization of a monomer comprising at least one amine moiety or nitrogen containing moiety, or (3) crosslinking of an amine-containing intermediate with a crosslinking agent, optionally containing amine moieties.

Embodiment 729. The composition for use according to any one of embodiments 571 to 692 wherein the composition is the pharmaceutical composition of embodiment 728 wherein the crosslinked amine polymer is a crosslinked homopolymer or a crosslinked copolymer.

Embodiment 730. The composition for use according to any one of embodiments 571 to 692 wherein the composition is the pharmaceutical composition of embodiment 728 wherein the crosslinked amine polymer comprises free amine moieties, separated by the same or varying lengths of repeating linker units.

Embodiment 731. The composition for use according to any one of embodiments 571 to 692 wherein the composition is the pharmaceutical composition of embodiment 728 wherein the crosslinked amine polymer is prepared by polymerizing an amine-containing monomer with a crosslinking agent in a substitution polymerization reaction.

Embodiment 732. The composition for use according to any one of embodiments 571 to 692 wherein the composition is the pharmaceutical composition of embodiment 731 wherein the amine-containing monomer is a linear amine possessing at least two reactive amine moieties to participate in the substitution polymerization reaction.

Embodiment 733. The composition for use according to any one of embodiments 571 to 692 wherein the composition is the pharmaceutical composition of embodiment 731 or 732 wherein the amine-containing monomer is 1,3-Bis [bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino] ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino) ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl) ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, or 3-(Methylamino)pyrrolidino.

Embodiment 734. The composition for use according to any one of embodiments 571 to 692 wherein the composition is the pharmaceutical composition of any of embodiments 728, 730, 732, and 733 wherein the crosslinking agent is selected from the group consisting of dihaloalkanes, haloalkyloxiranes, alkyloxirane sulfonates, di(haloalkyl)amines, tri(haloalkyl) amines, diepoxides, triepoxides, tetraepoxides, bis (halomethyl)benzenes, tri(halomethyl)benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol diglycidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis (glycidyloxy) diphenylmethane, bisphenol F diglycidyl ether, 1,4-bis(2',3'epoxypropyl)perfluoro-n-butane, 2,6-di (oxiran-2-ylmethyl)-1,2,3,5,6,7-hexahydropyrrolo[3,4-f] isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl) tetramethyldisiloxane, 9,9-bis [4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1,3,5,7,9,11, 14-heptacyclopentyltricyclo [7,3,3,15, 11]heptasiloxane, 4,4'methylenebis(N,N-diglycidylaniline), bis(halomethyl) benzene, bis(halomethyl)biphenyl and bis(halomethyl) naphthalene, toluene diisocyanate, acryloyl chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino) ethane, Bis(3-chloropropyl)amine, 1,3-Dichloro-2-propanol, 1,3-Dichloropropane, 1-chloro-2,3-epoxypropane, tris [(2-oxiranyl)methyl]amine, and combinations thereof.

Embodiment 735. The composition for use according to any one of embodiments 571 to 692 wherein the composition is the pharmaceutical composition of embodiment 728 wherein the preparation of the crosslinked amine polymer comprises radical polymerization of an amine monomer comprising at least one amine moiety or nitrogen containing moiety.

Embodiment 736. The composition for use according to any one of embodiments 571 to 692 wherein the composition is the pharmaceutical composition of any preceding enumerated embodiment wherein the crosslinked amine polymer has an equilibrium swelling ratio in deionized water of about 1.5 or less.

Embodiment 737. The composition for use according to any one of embodiments 571 to 692 wherein the composition is the pharmaceutical composition of any preceding enumerated embodiment wherein the crosslinked amine polymer has an equilibrium swelling ratio in deionized water of about 1 or less.

Embodiment 738. The composition for use according to any one of embodiments 571 to 692 wherein the composition is the pharmaceutical composition of any preceding enumerated embodiment wherein the crosslinked amine polymer has a chloride ion to phosphate ion binding molar ratio of at least 0.5:1, respectively, in an aqueous simulated small intestine inorganic buffer (“SIB”) containing 36 mM NaCl, 20 mM $NaH_2PO_4$, and 50 mM 2-(N-morpholino) ethanesulfonic acid (MES) buffered to pH 5.5 and at 37° C.

Embodiment 739. The composition for use according to any one of embodiments 571 to 692 wherein the composition is the pharmaceutical composition of any preceding enumerated embodiment wherein the crosslinked amine polymer has a chloride ion to phosphate ion binding molar ratio of at least 1:1, respectively, in an aqueous simulated small intestine inorganic buffer ("SIB") containing 36 mM NaCl, 20 mM $NaH_2PO_4$, and 50 mM 2-(N-morpholino) ethanesulfonic acid (MES) buffered to pH 5.5 and at 37° C.

Embodiment 740. The composition for use according to any one of embodiments 571 to 692 wherein the composition is the pharmaceutical composition of any preceding enumerated embodiment wherein the crosslinked amine polymer has a chloride ion to phosphate ion binding molar ratio of at least 2:1, respectively, in an aqueous simulated small intestine inorganic buffer ("SIB") containing 36 mM NaCl, 20 mM $NaH_2PO_4$, and 50 mM 2-(N-morpholino) ethanesulfonic acid (MES) buffered to pH 5.5 and at 37° C.

Embodiment 741. The composition for use according to any one of embodiments 571 to 692 wherein the composition is the pharmaceutical composition of any preceding enumerated embodiment wherein the crosslinked amine polymer has a proton binding capacity of at least 10 mmol/g and a chloride ion binding capacity of at least 10 mmol/g in an aqueous simulated gastric fluid buffer ("SGF") containing 35 mM NaCl and 63 mM HCl at pH 1.2 and 37° C.

Embodiment 742. The composition for use according to any one of embodiments 571 to 692 wherein the composition is the pharmaceutical composition of any preceding enumerated embodiment wherein the crosslinked amine polymer has an equilibrium proton binding capacity of at least 12 mmol/g and a chloride ion binding capacity of at least 12 mmol/g in an aqueous simulated gastric fluid buffer ("SGF") containing 35 mM NaCl and 63 mM HCl at pH 1.2 and 37° C.

Embodiment 743. The composition for use according to any one of embodiments 571 to 692 wherein the composition is the pharmaceutical composition of any preceding enumerated embodiment wherein the crosslinked amine polymer has an equilibrium proton binding capacity of at least 14 mmol/g and a chloride ion binding capacity of at least 14 mmol/g in an aqueous simulated gastric fluid buffer ("SGF") containing 35 mM NaCl and 63 mM HCl at pH 1.2 and 37° C.

Embodiment 744. The composition for use according to any one of embodiments 571 to 692 wherein the composition is the pharmaceutical composition of any preceding enumerated embodiment wherein the percentage of quaternized amines is less than 40%.

Embodiment 745. The composition for use according to any one of embodiments 571 to 692 wherein the composition is the pharmaceutical composition of any preceding enumerated embodiment wherein the percentage of quaternized amines is less than 30%.

Embodiment 746. The composition for use according to any one of embodiments 571 to 692 wherein the composition is the pharmaceutical composition of any preceding enumerated embodiment wherein the percentage of quaternized amines is less than 20%.

Embodiment 747. The composition for use according to any one of embodiments 571 to 692 wherein the composition is the pharmaceutical composition of any preceding enumerated embodiment wherein the percentage of quaternized amines is less than 10%.

Embodiment 748. The composition for use according to any one of embodiments 571 to 692 wherein the composition is the pharmaceutical composition of any preceding enumerated embodiment wherein the percentage of quaternized amines is less than 5%.

Embodiment 749. The composition for use according to any one of embodiments 571 to 692 wherein the composition is the pharmaceutical composition of any preceding enumerated embodiment wherein the crosslinked amine polymer is a gel or a bead having a mean particle size of 40 to 180 micrometers.

Embodiment 750. The composition for use according to any one of embodiments 571 to 692 wherein the composition is the pharmaceutical composition of any preceding enumerated embodiment wherein the crosslinked amine polymer is a gel or a bead having a mean particle size of 60 to 160 micrometers.

Embodiment 751. The composition for use according to any one of embodiments 571 to 692 wherein the composition is the pharmaceutical composition of any preceding enumerated embodiment wherein the crosslinked amine polymer is a gel or a bead having a mean particle size of 80 to 140 micrometers.

Embodiment 752. The composition for use according to any one of embodiments 571 to 692 wherein the composition is the pharmaceutical composition of any one of embodiments 749 to 751 wherein less than about 0.5 volume percent of the particles have a diameter of less than about 10 micrometers.

Embodiment 753. The composition for use according to any one of embodiments 571 to 692 wherein the composition is the pharmaceutical composition of any one of embodiments 749 to 751 wherein less than about 5 volume percent of the particles have a diameter of less than about 20 micrometers.

Embodiment 754. The composition for use according to any one of embodiments 571 to 692 wherein the composition is the pharmaceutical composition of any one of embodiments 749 to 751 wherein less than about 0.5 volume percent of the particles have a diameter of less than about 20 micrometers.

Embodiment 755. The composition for use according to any one of embodiments 571 to 692 wherein the composition is the pharmaceutical composition of any one of embodiments 749 to 751 wherein less than about 5 volume percent of the particles have a diameter of less than about 30 micrometers.

Embodiment 756. The composition for use according to any one of embodiments 571 to 692 wherein the composition is the pharmaceutical composition of any preceding enumerated embodiment in a dosage unit form.

Embodiment 757. The composition for use according to any one of embodiments 571 to 692 wherein the composition is the pharmaceutical composition of embodiment 756 wherein the dosage unit form is a capsule, tablet or sachet dosage form.

Embodiment 758. The composition for use according to any one of embodiments 571 to 692 wherein the composition is the pharmaceutical composition of any preceding enumerated embodiment wherein the pharmaceutical composition comprises a pharmaceutically acceptable carrier, excipient, or diluent.

Embodiment 759. The composition for use according to any one of embodiments 571 to 692 wherein the composition is a method of treating and acid/base disorder in an animal including a human by removing HCl through oral administration of a pharmaceutical composition of any of the preceding enumerated embodiments.

Embodiment 760. The composition for use according to any one of embodiments 571 to 692 wherein the composition is the method of treatment of embodiment 759 wherein the acid/base disorder is metabolic acidosis.

Embodiment 761. The composition for use according to any one of embodiments 571 to 692 wherein the composition is the method of treatment of embodiment 759 wherein the pH is controlled or normalized.

Embodiment 762. The composition for use according to any one of embodiments 571 to 692 wherein the composition is the method of treatment of embodiment 759 wherein the serum bicarbonate is controlled or normalized.

Embodiment 763. The composition for use according to any one of embodiments 571 to 692 wherein the composition is the method of treatment of embodiment 759 wherein less than 1 g of sodium or potassium is administered per day.

Embodiment 764. The composition for use according to any one of embodiments 571 to 692 wherein the composition is the method of treatment of embodiment 759 wherein less than 0.5 g of sodium or potassium is administered per day.

Embodiment 765. The composition for use according to any one of embodiments 571 to 692 wherein the composition is the method of treatment of embodiment 759 wherein less than 0.1 g of sodium or potassium is administered per day.

Embodiment 766. The composition for use according to any one of embodiments 571 to 692 wherein the composition is the method of treatment of embodiment 759 wherein no sodium or potassium is administered.

Embodiment 767. The composition for use according to any one of embodiments 571 to 692 wherein the composition is the pharmaceutical composition of any of embodiments 682-755 wherein a dose of the pharmaceutical composition is titrated based on the serum bicarbonate values of a patient in need of treatment or other indicators of acidosis.

Embodiment 768. The composition for use according to any one of embodiments 571 to 692 wherein the composition is a polymer comprising a structure corresponding to Formula 4:

Formula 4

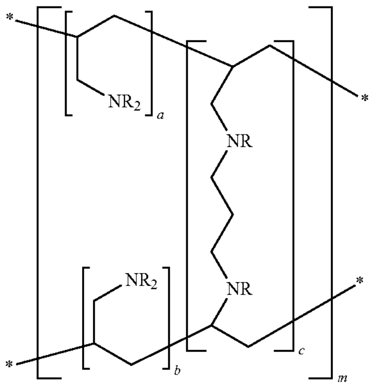

wherein each R is independently hydrogen or an ethylene crosslink between two nitrogen atoms of the crosslinked amine polymer

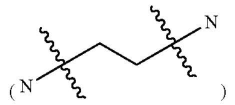

and a, b, c, and m are integers.

Embodiment 769. The composition for use according to any one of embodiments 571 to 692 wherein the composition is the polymer of embodiment 768 wherein m is a large integer indicating an extended polymer network.

Embodiment 770. The composition for use according to any one of embodiments 571 to 692 wherein the composition is the polymer of embodiment 768 or 769 wherein a ratio of the sum of a and b to c (i.e., a+b:c) is in the range of about 1:1 to 5:1.

Embodiment 771. The composition for use according to any one of embodiments 571 to 692 wherein the composition is the polymer of embodiment 768 or 769 wherein a ratio of the sum of a and b to c (i.e., a+b:c) is in the range of about 1.5:1 to 4:1.

Embodiment 772. The composition for use according to any one of embodiments 571 to 692 wherein the composition is the polymer of embodiment 768 or 769 wherein a ratio of the sum of a and b to c (i.e., a+b:c) is in the range of about 1.75:1 to 3:1.

Embodiment 773. The composition for use according to any one of embodiments 571 to 692 wherein the composition is the polymer of embodiment 768 or 769 wherein a ratio of the sum of a and b to c (i.e., a+b:c) is in the range of about 2:1 to 2.5:1.

Embodiment 774. The composition for use according to any one of embodiments 571 to 692 wherein the composition is the polymer of embodiment 768 or 769 wherein the sum of a and b is 57 and c is 24.

Embodiment 775. The composition for use according to any one of embodiments 571 to 692 wherein the composition is the polymer of any of embodiments 768 or 774 wherein 50-95% of the R substituents are hydrogen and 5-50% are an ethylene crosslink between two nitrogens of the crosslinked amine polymer.

Embodiment 776. The composition for use according to any one of embodiments 571 to 692 wherein the composition is the polymer of any of embodiments 768 or 774 wherein 55-90% of the R substituents are hydrogen and 10-45% are an ethylene crosslink between two nitrogens of the crosslinked amine polymer.

Embodiment 777. The composition for use according to any one of embodiments 571 to 692 wherein the composition is the polymer of any of embodiments 768 or 774 wherein 60-90% of the R substituents are hydrogen and 10-40% are an ethylene crosslink between two nitrogens of the crosslinked amine polymer.

Embodiment 778. The composition for use according to any one of embodiments 571 to 692 wherein the composition is the polymer of any of embodiments 768 to 774 wherein 65-90% of the R substituents are hydrogen and 10-35% are an ethylene crosslink between two nitrogens of the crosslinked amine polymer.

Embodiment 779. The composition for use according to any one of embodiments 571 to 692 wherein the composition is the polymer of any of embodiments 768 to 774 wherein 70-90% of the R substituents are hydrogen and 10-30% are an ethylene crosslink between two nitrogens of the crosslinked amine polymer.

Embodiment 780. The composition for use according to any one of embodiments 571 to 692 wherein the composition is the polymer of any of embodiments 768 to 774 wherein 75-85% of the R substituents are hydrogen and 15-25% are an ethylene crosslink between two nitrogens of the crosslinked amine polymer.

Embodiment 781. The composition for use according to any one of embodiments 571 to 692 wherein the composition is the polymer of any of embodiments 768 to 774 wherein 80-85% of the R substituents are hydrogen and 15-20% are an ethylene crosslink between two nitrogens of the crosslinked amine polymer.

Embodiment 782. The composition for use according to any one of embodiments 571 to 692 wherein the composition is the polymer of any of embodiments 768 to 774 wherein about 81% of the R substituents are hydrogen and about 19% are an ethylene crosslink.

Embodiment 783. The composition for use according to any one of embodiments 571 to 592 wherein the method of treatment further includes the feature or features set out in any one of embodiments 1 to 570, or part thereof.

Embodiment 784. A composition for use in a method of treating metabolic acidosis in an adult human patient wherein said treatment is administered to the patient less frequently than once per day, said composition being a nonabsorbable composition having the capacity to remove protons from the patient.

Embodiment 785. The composition of embodiment 784, wherein the composition is administered on a regular schedule.

Embodiment 786. The composition of embodiment 784, wherein the regular schedule is once every two days.

Embodiment 787. The composition of embodiment 785, wherein the regular schedule is once every three days.

Embodiment 788. The composition of embodiment 785, wherein the regular schedule is twice a week.

Embodiment 789. The composition of embodiment 785, wherein the regular schedule is three times a week.

Embodiment 790. The composition of embodiment 785, wherein the regular schedule is four times a week.

Embodiment 791. The composition of any one of embodiments 784 to 790 wherein the composition is as defined in any preceding enumerated embodiment.

Embodiment 792. The composition of any one of embodiments 784 to 791 wherein the method of treatment is as defined in any preceding enumerated embodiment.

Embodiment 793. A method of increasing serum bicarbonate levels in an individual afflicted with an acid-base disorder, the method comprising oral administration of a pharmaceutical composition to increase the individual's serum bicarbonate levels wherein:

(i) the pharmaceutical composition binds a target species in the individual's digestive system when given orally, the target species being selected from the group consisting of protons, strong acids, and conjugate bases of strong acids and (ii) the pharmaceutical composition increases the serum bicarbonate level by at least 1 mEq/l in a placebo controlled study, said increase being the difference between the cohort average serum bicarbonate level in a first cohort at the end of the study, relative to the cohort average serum bicarbonate level in a second cohort at the end of the study, wherein the first cohort's subjects receive the pharmaceutical composition and the second cohort's subjects receive a placebo, wherein the first and second cohorts each comprise at least 25 subjects, each cohort is prescribed the same diet during the study and the study lasts at least two weeks.

Embodiment 794. The method of embodiment 793 wherein the first cohort receives a daily dose of the pharmaceutical composition that does not exceed 100 g/day.

Embodiment 795. The method of embodiment 793 wherein the first cohort receives a daily dose of the pharmaceutical composition that does not exceed 50 g/day.

Embodiment 796. The method of embodiment 793 wherein the first cohort receives a daily dose of the pharmaceutical composition that does not exceed 30 g/day.

Embodiment 797. The method of embodiment 793 wherein the first cohort receives a daily dose of the pharmaceutical composition that does not exceed 25 g/day.

Embodiment 798. The method of embodiment 793 wherein the first cohort receives a daily dose of the pharmaceutical composition that does not exceed 20 g/day.

Embodiment 799. The method of embodiment 793 wherein the first cohort receives a daily dose of the pharmaceutical composition that does not exceed 15 g/day.

Embodiment 800. The method of embodiment 793 wherein the first cohort receives a daily dose of the pharmaceutical composition that does not exceed 10 g/day.

Embodiment 801. The method of embodiment 793 wherein the first cohort receives a daily dose of the pharmaceutical composition that does not exceed 5 g/day.

Embodiment 802. The method of any of embodiments 793 to 801 wherein the target species is protons.

Embodiment 803. The method of any of embodiments 793 to 801 wherein the target species is chloride ions.

Embodiment 804. The method of any of embodiments 793 to 801 wherein the target species is a strong acid.

Embodiment 805. The method of any of embodiments 793 to 801 wherein the target species is HCl.

Embodiment 806. The method of any of embodiments 793 to 805 wherein the pharmaceutical composition is not absorbed when ingested.

Embodiment 807. The method of any of embodiments 793 to 806 wherein the composition is a pharmaceutical composition comprising a proton-binding, crosslinked amine polymer comprising the residue of an amine corresponding to Formula 1:

Formula 1

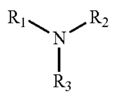

wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

Embodiment 808. The method of any of embodiments 793 to 806 wherein the composition is a pharmaceutical composition comprising a proton-binding, crosslinked amine polymer comprising the residue of an amine corresponding to Formula 1:

Formula 1

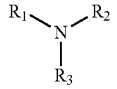

wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein the interfering ions are phosphate ions and the interfering ion buffer is a buffered solution at pH 5.5 of 36 mM chloride and 20 mM phosphate.

Embodiment 809. The method of embodiments 807 or 808 wherein the crosslinked amine polymer has an equilibrium chloride binding capacity of at least 7.5 mmol/g in an aqueous simulated gastric fluid buffer ("SGF") containing 35 mM NaCl and 63 mM HCl at pH 1.2 and 37° C.

Embodiment 810. The method of embodiments 807 or 808 wherein the crosslinked amine polymer has an equilibrium chloride binding capacity of at least 10 mmol/g in an aqueous simulated gastric fluid buffer ("SGF") containing 35 mM NaCl and 63 mM HCl at pH 1.2 and 37° C.

Embodiment 811. The method of embodiments 807 or 808 wherein the crosslinked amine polymer has an equilibrium swelling ratio in deionized water of about 4 or less.

Embodiment 812. The method of embodiments 807 or 808 wherein the crosslinked amine polymer has an equilibrium swelling ratio in deionized water of about 3 or less.

Embodiment 813. The method of embodiments 807 or 808 wherein the crosslinked amine polymer has an equilibrium swelling ratio in deionized water of about 2 or less.

Embodiment 814. The method of any of embodiments 807 to 813 wherein $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ is not hydrogen.

Embodiment 815. The method of any of embodiments 807 to 813 wherein $R_1$, $R_2$ and $R_3$ are independently hydrogen, aliphatic or heteroaliphatic provided, however, at least one of $R_1$, $R_2$ and $R_3$ is other than hydrogen.

Embodiment 816. The method of any of embodiments 807 to 813 wherein the crosslinked amine polymer is prepared by substitution polymerization of the amine with a polyfunctional crosslinker, optionally also comprising amine moieties.

Embodiment 817. The method of any of embodiments 807 to 816 wherein the potential renal acid load (PRAL value) of the diet is, on average, 0.82 mEq/d).

Embodiment 818. The method of any of embodiments 807 to 817 wherein eligible subjects for the study have chronic kidney disease (CKD Stage 3-4; eGFR 20—<60 mL/min/1.73 $m^2$) and a baseline serum bicarbonate value at the start of the study between 12 and 20 mEq/L.

Embodiment 819. The method of any of embodiments 807 to 818 wherein the pharmaceutical composition increases the serum bicarbonate level by at least 2 mEq/l in the placebo controlled study.

Embodiment 820. The method of any of embodiments 807 to 818 wherein the pharmaceutical composition increases the serum bicarbonate level by at least 3 mEq/l in the placebo controlled study.

Embodiment 821. The method or composition of any preceding enumerated embodiment wherein the individual or adult human patient has chronic kidney disease.

Embodiment 822. The method or composition of any preceding enumerated embodiment wherein the individual or adult human patient is not yet in need for kidney replacement therapy (dialysis or transplant).

Embodiment 823. The method or composition of any preceding enumerated embodiment wherein the individual or adult human patient has not yet reached end stage renal disease ("ESRD").

Embodiment 824. The method or composition of any preceding enumerated embodiment wherein the individual or adult human patient has a mGFR of at least 15 mL/min/1.73 $m^2$.

Embodiment 825. The method or composition of any preceding enumerated embodiment wherein the individual or adult human patient has an eGFR of at least 15 mL/min/1.73 $m^2$.

Embodiment 826. The method or composition of any preceding enumerated embodiment wherein the individual or adult human patient has a mGFR of at least 30 mL/min/1.73 $m^2$.

Embodiment 827. The method or composition of any preceding enumerated embodiment wherein the individual or adult human patient has an eGFR of at least 30 mL/min/1.73 $m^2$.

Embodiment 828. The method or composition of any preceding enumerated embodiment wherein the individual or adult human patient has a mGFR of less than 45 mL/min/1.73 $m^2$ for at least three months.

Embodiment 829. The method or composition of any preceding enumerated embodiment wherein the individual or adult human patient has an eGFR of less than 45 mL/min/1.73 $m^2$ for at least three months.

Embodiment 830. The method or composition of any preceding enumerated embodiment wherein the individual or adult human patient has a mGFR of less than 60 mL/min/1.73 $m^2$ for at least three months.

Embodiment 831. The method or composition of any preceding enumerated embodiment wherein the individual or adult human patient has an eGFR of less than 60 mL/min/1.73 $m^2$ for at least three months.

Embodiment 832. The method or composition of any preceding enumerated embodiment wherein the individual or adult human patient has Stage 3A CKD, Stage 3B CKD, or Stage 4 CKD.

Embodiment 833. A method of treating an individual afflicted with an acid-base disorder characterized by a baseline serum bicarbonate value of less than 22 mEq/l, the method comprising oral administration of a daily dose of a pharmaceutical composition containing a nonabsorbable composition;

- wherein said oral administration increases the individual's serum bicarbonate value from baseline to an increased serum bicarbonate value that exceeds the baseline serum bicarbonate value by at least 1 mEq/l; and
- wherein the treatment enables the increased serum bicarbonate value to be sustained over a prolonged period of at least one week, at least one month, at least two months, at least three months, at least six months, or at least one year.

Embodiment 834. The method or pharmaceutical composition of embodiment 833, wherein the method or pharmaceutical composition is one of any preceding enumerated embodiments.

Embodiment 835. The method of any preceding enumerated embodiment wherein the treatment decreases the individual's anion gap by at least 1 mEq/L.

Embodiment 836. The method of any preceding enumerated embodiment wherein the treatment decreases the individual's anion gap by at least 2 mEq/L.

Having described the invention in detail, it will be apparent that modifications and variations are possible without departing the scope of the invention defined in the appended claims. Furthermore, it should be appreciated that all examples in the present disclosure are provided as non-limiting examples.

Exemplary Synthetic Approaches for the Preparation of Nonabsorbed Polymers for the Treatment of Acid-Base Imbalance (Reproduced from WO2016/094685)

Exemplary Synthesis A

Step 1: Two aqueous stock solutions of monomer (50% w/w) were prepared by independently dissolving 43.83 g allylamine hydrochloride and 45.60 g diallylpropyldiamine ("DAPDA") in water. A 3-neck, 2 L round bottom flask with four side baffles equipped with an overhead stirrer (stirring at 180 rpm), Dean-Stark apparatus and condenser, and nitrogen inlet, was charged with 12 g surfactant (Stepan Sulfonic 100) dissolved in 1,200 g of a heptane/chlorobenzene solution (26/74 v/v), followed by the aqueous stock solutions, and an additional portion of water (59.14 g). In a separate vessel, a 15 wt % solution of initiator 2,2'-azobis (2-methylpropionamidine)-dihydrochloride ("V-50") (9.08 g) in water was prepared. The two mixtures were independently sparged with nitrogen while the reaction vessel was brought to 67° C. in an oil bath (approximately 30 min). Under inert atmosphere, the initiator solution was added to the reaction mixture, and subsequently heated at 67° C. for 16 hours. A second aliquot of initiator solution (equal to the first) and the reaction mixture, were sparged with nitrogen for 30 minutes and combined before increasing the temperature to 115° C. for a final dehydration step (Dean-Stark). The reaction was held at 115° C. until water stopped collecting in the Dean-Stark trap (6 h, 235 mL removed, >90% of total water, $T_{internal}$>99° C.). The reaction was allowed to cool to room temperature, and the stirring stopped to allow the beads to settle. The organic phase was removed from the bead cake by decanting. The beads were purified by washing (MeOH two times, $H_2O$ once, 1N HCl two times, $H_2O$ once, 1N NaOH three times, and then $H_2O$ until the pH of solution after washing was 7) and dried by lyophilization.

Step 2: Dry preformed amine polymer beads (15.00 g) prepared in accordance with Step 1 were added to a 250 mL round bottom flask equipped with a stir paddle and nitrogen gas inlet. To the beads was added 1,2-dichloroethane (DCE) (90 mL, resulting in a 1:6 bead to DCE (g/mL) ratio). The beads were dispersed in the DCE using mechanical agitation (~150 rpm stirring). Water (3.75 mL, resulting in a 0.25:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (100 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48 hours. Swelling ratio, particle size, chloride binding capacity in SGF and chloride binding capacity (SIB—Cl) and phosphate binding capacity (SIB—P) in SIB are presented in Table S-1 for the resulting polymers.

TABLE S-1

| | Water: | | Particle Size (microns) | | | Binding (mmol/g dry weight) | | |
|---|---|---|---|---|---|---|---|---|
| Unique ID | Bead | Swelling | D10 | D50 | D90 | SGF | SIB-Cl | SIB-P |
| Averaged from 019069-A1 FA pooled batch* | — | 5.0 | 79 | 129 | 209 | 13.9 | 2.0 | 6.0 |
| 030008-A1 FA | 0.00 | 1.9 | NM | NM | NM | 11.8 | 2.4 | 4.0 |
| 019070-A1 FA | 0.05 | 1.5 | 64 | 99 | 155 | 11.1 | 2.4 | 3.5 |
| 019070-A2 FA | 0.15 | 1.1 | 64 | 97 | 147 | 11.0 | 3.3 | 2.5 |
| 019070-A3 FA | 0.25 | 1.2 | 63 | 102 | 168 | 10.4 | 4.4 | 1.4 |
| 019070-A4 FA | 0.35 | 0.7 | 59 | 91 | 140 | 10.7 | 4.5 | 1.3 |
| 019070-A5 FA | 0.45 | 1.6 | 63 | 105 | 184 | 11.1 | 3.7 | 2.5 |

*Averaged data from 4 batches of preformed polyamine bead

Exemplary Syntheses B-E

Step 1 Exemplary Synthesis B: To a 500 mL round bottom flask, polyallylamine (14 g, 15 kDa), and water (28 mL) were added. The solution was purged with nitrogen and stirred overhead at 220 rpm for 1 hour to completely dissolve the polymer. Next, 30 wt % aqueous NaOH (7 mL) was added and stirred for 5 minutes. A premade solution of DCE (175 mL), n-heptane (105 mL), and Span 80 (2.8 g) was added to the aqueous solution. The solution was heated to 70° C. and stirred for 16 hours. The Dean-Stark step was initiated by adding cyclohexane (100 mL) and heating the reaction to 95° C. to remove the water (>90%) from the beads. Swelling ratio, chloride binding capacity in SGF and chloride binding capacity (SIB—Cl) and phosphate binding capacity (SIB—P) in SIB are presented in Table S-2 (entries 018013-A1 FA and 015026-A1 FA) for the resulting polymer with SGF, SIB—Cl and SIB—P values expressed in mmol/g dry bead.

Step 1 Exemplary Synthesis C: To a 100 mL round bottom flask, DCP (31 mL), n-heptane (19 mL), and Span 80 (0.5 g) were added. A separate aqueous stock solution of polyallylamine (2.3 g, 900 kDa), Aq NaOH (1 mL, 30 wt %), and water (4 mL) was prepared. The aqueous stock solution was added to the organic solution in the round bottom flask. The solution was purged with nitrogen for 15 minutes, heated to 70° C., and stirred for 16 hours. Methanol (30 mL) was added to the reaction mixture and the organic solvent removed by decanting. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (018001-A2b FA) for the resulting polymer with SGF, SIB—Cl and SIB—P values expressed in mmol/g dry bead.

Step 1 Exemplary Synthesis D: Polyallylamine 15 kDa (3.0 g) and water (9.05 g) were dissolved in a conical flask. Sodium hydroxide (0.71 g) was added to the solution and the mixture was stirred for 30 minutes. To a 100 mL round bottom flask, equipped side arm and overhead stirrer was added 0.38 g of sorbitan sesquioleate and 37.9 g of toluene. The overhead stirrer was switched on to provide agitation to the reaction solution. Dichloropropanol (0.41 g) was added directly to the polyallylamine solution while stirring. The resulting aqueous polyallylamine solution was added to the toluene solution in the 100 mL flask. The reaction was heated to 50° C. for 16 hours. After this time, the reaction was heated to 80° C. for 1 hour and then cooled to room temperature. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (entries 002054-A3 FA and 011021-A6 FA) for the resulting polymer with SGF, SIB—Cl and SIB—P values expressed in mmol/g dry bead.

Step 1 Exemplary Synthesis E: Polyallylamine 15 kDa (3.1 g) and water (9.35 g) were dissolved in a conical flask. Sodium hydroxide (0.73 g) was added to the solution and the mixture was stirred for 30 minutes. To a 100 mL round bottom flask, equipped side arm and overhead stirrer was added 0.31 g of sorbitan trioleate and 39.25 g of toluene. The overhead stirrer was switched on to provide agitation to the reaction solution. The aqueous polyallylamine solution was added to the toluene solution in the 100 mL flask. Epichlorohydrin (0.30 g) was added directly to the reaction mixture using a syringe. The reaction was heated to 50° C. for 16 hours. After this time the reaction was heated to 80° C. for 1 hour and then cooled to room temperature. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (entries 002050-A1 FA and 002050-A2 FA) for the resulting polymer with SGF, SIB—Cl and SIB—P values expressed in mmol/g dry bead.

TABLE S-2

| | | | Binding (mmol/g dry weight) | | |
|---|---|---|---|---|---|
| Unique ID | Crosslinker | Swelling | SGF | SIB-CI | SIB-P |
| 018013-A1 FA | DCE | 6.1 | 16.9 | 2.2 | 7.3 |
| 015026-A1 FA | DCE | 5.9 | 16.6 | 2.0 | 7.2 |
| 018001-A2b FA | DCP | 4.6 | 15.9 | 1.9 | 7.1 |
| 002054-A3 FA | DC2OH | 6.5 | 14.3 | 1.6 | 7.1 |
| 011021-A6 FA | DC2OH | 3.0 | 14.3 | 1.5 | 6.1 |
| 002050-A1 FA | ECH | 8.3 | 14.4 | 1.7 | 7.0 |
| 002050-A2 FA | ECH | 8.8 | 14.2 | 1.6 | 7.1 |

Step 1 polymers selected from Exemplary Synthesis B and D were subjected to Step 2 crosslinking according to the following general procedure. Dry preformed amine polymer beads were added to a reactor vessel equipped with a stir paddle and nitrogen gas inlet. To the beads was added 1,2-dichloroethane (DCE). The beads were dispersed in the DCE using mechanical agitation. Water was added directly to the dispersion, and stirring was continued. The flask was immersed into an oil bath held at a chosen temperature. The reaction was held in the oil bath and agitated using mechanical stirring under a nitrogen atmosphere for a chosen amount of time. Methanol was added to the reaction and, solvent was removed by decanting. The beads were then filtered, and then purified by washing. Swelling ratio, chloride binding capacity in SGF and chloride binding capacity (SIB—Cl) and phosphate binding capacity (SIB—P) in SIB are presented in Table S-3.

TABLE S-3

| | Preformed amine | Step 1 | | Binding (mmol/g dry weight) | | |
|---|---|---|---|---|---|---|
| Unique ID | polymer | xlinker | Swelling | SGF | SIB-Cl | SIB-P |
| 018022-A2 FA | 018013-A1 FA | DCE | 1.7 | 14.9 | 4.0 | 4.6 |
| 015032-A1 FA | 015026-A1 FA | DCE | 1.4 | 13.2 | 6.1 | 1.5 |
| 015032-B2 FA | 015026-A1 FA | DCE | 1.2 | 13.0 | 6.1 | 1.5 |
| 002064-B4 FA | 002054-A3 FA | DC2OH | 3.1 | 12.1 | 1.7 | 5.6 |
| 002064-B5 FA | 002054-A3 FA | DC2OH | 2.7 | 12.3 | 1.7 | 5.5 |

Exemplary Synthesis F

Step 2 Exemplary Synthesis F: Dry preformed amine polymer beads (3.00 g) (prepared as described in Step 1 of Exemplary Synthesis A) were added to a 100 mL round bottom flask equipped with a stir paddle and nitrogen gas inlet. To the beads was added DCP (4.30 mL) and DCE (13.70 mL), resulting in a 1:6 bead to DCE mass/volume ratio). The beads were dispersed in the DCE using mechanical agitation (~150 rpm stirring). Water (3.00 mL, resulting in a 1:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (60 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48. Swelling ratio, chloride binding capacity in SGF and chloride binding capacity (SIB—Cl) and phosphate binding capacity (SIB—P) in SIB are presented in Table S-4.

TABLE S-4

| | Vol % | | Binding (mmol/g dry weight) | | |
|---|---|---|---|---|---|
| Unique ID | DCE | Swelling | SGF | SIB-CI | SIB-P |
| 019031-B1 FA | 100 | 1.1 | 11.3 | 5.2 | 1.3 |
| 019031-B2 FA | 92 | 1.0 | 11.2 | 5.2 | 1.4 |
| 019031-B3 FA | 84 | 0.9 | 11.3 | 4.9 | 1.7 |

TABLE S-4-continued

| | Vol % | | Binding (mmol/g dry weight) | | |
|---|---|---|---|---|---|
| Unique ID | DCE | Swelling | SGF | SIB-Cl | SIB-P |
| 019031-B4 FA | 76 | 1.0 | 11.3 | 4.8 | 1.8 |
| 019031-B5 FA | 68 | 1.0 | 11.4 | 4.6 | 1.9 |
| 019031-B6 FA | 0 | 1.1 | 11.2 | 3.1 | 3.5 |

Exemplary Synthesis G

Polyallylamine hydrochloride is dissolved in water. Sodium hydroxide is added to partially deprotonate the polyallylamine hydrochloride (preferably 50 mol %). The aqueous phase generated has a water content (by weight) 2.42 times the weight of the polyallylamine hydrochloride. A baffled 3 necked flask, equipped with an overhead mechanical stirrer, nitrogen inlet, Dean Stark apparatus with condenser is set up to conduct the suspension reaction. A dichloroethane heptane mixture is prepared, such that there is 3 times by weight dichloroethane to heptane. This dichloroethane, heptane mixed solvent is added to the baffled 3 neck flask. The aqueous solution is added to the flask, such that the ratio is 6.4 dichloroethane to one water by volume. The reaction mixture is stirred and heated to 70° C. for 16 hours. At this point beads are formed. The Dean Stark step is initiated to remove all the water from the beads, while returning the dichloromethane and heptane back to the reaction mixture. Once no more water is removed the reaction mixture is cooled. Water and sodium hydroxide is added back to the reaction mixture at a ratio of 0.25 water to polyallylamine and up to 1 equivalent of sodium hydroxide per chloride on allylamine added (both calculated from polyallylamine hydrochloride added at the beginning of the reaction). The reaction is heated for a further 16 hours at 70° C. The reaction is cooled to room temperature. The beads are purified using a filter frit with the following wash solvents; methanol, water, aqueous solution of HCl, water, aqueous solution of sodium hydroxide and 3 water washes or until the filtrate measures a pH of 7.

Example 1

Efficacy of TRC101 in the Treatment of Acidosis in an Adenine-Induced Model of Nephropathy in Rats The drug substance, TRC101, is a non-absorbed free-flowing powder composed of low-swelling, spherical beads, approximately 100 micrometers in diameter; each bead is a single crosslinked, high molecular weight molecule. TRC101 is a highly crosslinked aliphatic amine polymer that is synthesized by first copolymerizing two monomers, allylamine hydrochloride and N,N'-diallyl-1,3-diaminopropane dihydrochloride, followed by crosslinking the polymer with 1,2-dichloroethane as described in Exemplary Synthesis A and in WO2016/094685 A1. TRC101 is the polymer with unique ID 019070-A3 FA in Table S-1 of Exemplary Synthesis A.

TRC101 is administered as a free-amine polymer and contains no counterion. TRC101 is insoluble in aqueous and non-aqueous solvents. TRC101 has both high proton and chloride binding capacity and chloride binding selectivity. The high amine content of the polymer is responsible for the high proton and chloride binding capacity of TRC101; the polymer's extensive crosslinking provides size exclusion properties and selectivity over other potential interfering anions, such as phosphate, citrate, bile acids, and short-chain and long-chain fatty acids.

TRC101 was evaluated in vivo in an adenine-induced rat model of chronic kidney disease (CKD) and metabolic acidosis. The study was designed in two parts. In both parts, male Sprague-Dawley rats weighing 260-280 g (10 per group) were first administered adenine (0.75 wt % in casein diet) for 2 weeks to induce nephropathy. Study Part 1 investigated the effect of early treatment with TRC101 administered in a casein diet with 0.25 wt % adenine for the 4 weeks following the 2-week nephropathy induction period. In contrast, study Part 2 assessed the effect of TRC101 administered after animals had been kept on casein diet with 0.25 wt % adenine for 5 weeks following the induction period, before the 4-week TRC101 treatment period was started. The dose levels of TRC101 were 0, 1.5, 3.0, and 4.5 wt % in the diet. Both study parts assessed the effect of withdrawing TRC101 after the end of the Treatment Phase with a 2-week Withdrawal Phase, in which TRC101 was discontinued in the low (1.5 wt %) and high (4.5 wt %) TRC101 dose groups, while dosing of TRC101 was continued in the mid dose group (3.0 wt %). All animals received casein diet with 0.25 wt % adenine during the Withdrawal Phase.

In both study parts, blood samples were taken from the tail vein of animals before treatments started and weekly during the Treatment and Withdrawal Periods for measurement of blood bicarbonate (SBC) using a HESKA Element POC™ blood gas analyzer. Animals were randomized based on SBC levels at baseline (i.e., following adenine induction of nephropathy and before initiation of the dosing period) so that mean baseline SBC levels were comparable across all dose groups. In addition, 24-h fecal collections were performed for the untreated and 4.5 wt % TRC101 groups. Collected fecal samples were stored at −20° C. before drying in a lyophilizer for 3 days followed by homogenization with a mortar and pestle. Anions (Cl, $SO_4$, and $PO_4$) were extracted from lyophilized, homogenized fecal samples by incubating the samples with NaOH for 18 hours. Sample supernatants were analyzed for by ion chromatography (IC).

Figure 2:
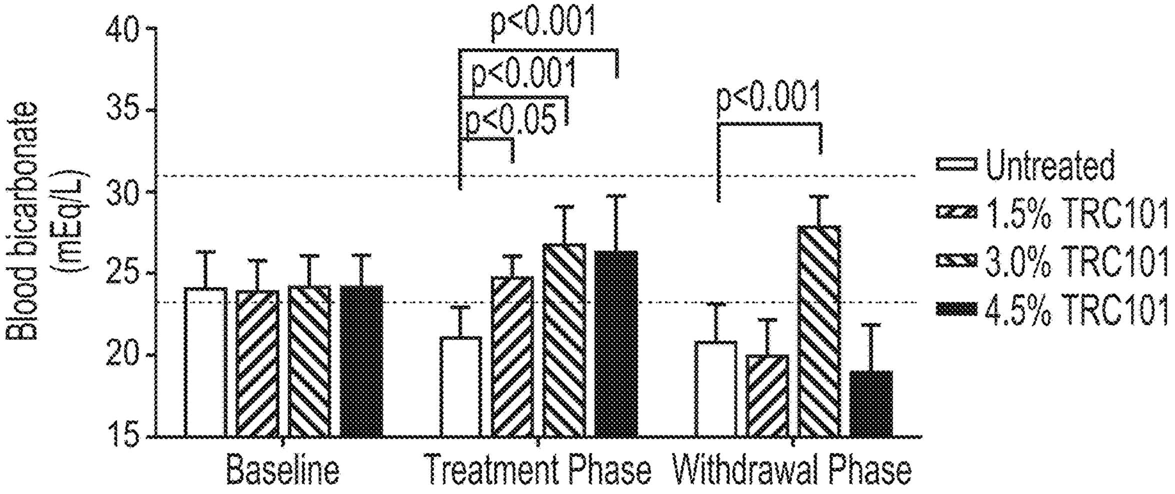
FIG. 2 is a graph of the effect of TRC101 on serum bicarbonate in a rat model of adenine-induced nephropathy and metabolic acidosis in Part 1 of the study described in Example 1.

In Part 1, early treatment with TRC101 resulted in a significant, dose-dependent increase in SBC in all treated groups, relative to the untreated controls (FIG. 2; statistical analysis: 2-way ANOVA with Dunnett's multiple comparisons test vs. untreated group; horizontal dotted lines marked the normal SBC range for male Sprague-Dawley rates of the same age). In contrast to the control group, which had a progressive decline in mean SBC due to adenine-induced renal insufficiency over the 4-week treatment period, mean SBC levels increased and remained in the normal range for low, mid and high treatment groups. Upon withdrawal of TRC101, mean SBC levels fell below the normal range in the low and high treatment groups and were similar to the untreated controls at the end of the withdrawal period; whereas, continued treatment with TRC101 (3.0 wt %) maintained SBC levels within the normal range, with the mean value significantly higher than that of the untreated controls.

Figure 3A:
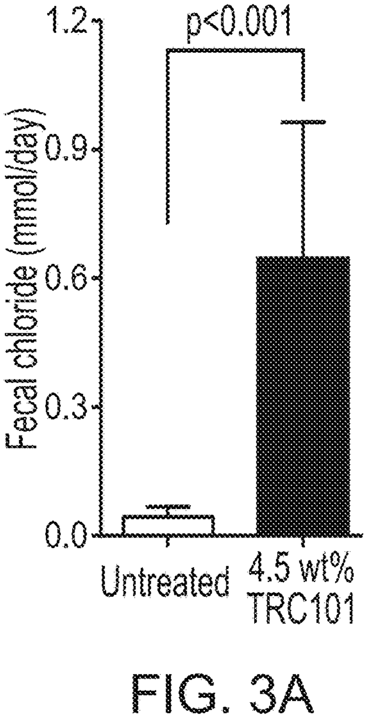
FIGS. 3A, 3B and 3C are graphs of the effect of TRC101 on fecal excretion of chloride (FIG. 3A), sulfate (FIG. 3B), and phosphate (FIG. 3C) in a rat model of adenine-induced nephropathy and metabolic acidosis in Part 1 of the study described in Example 1.
Figure 3B:
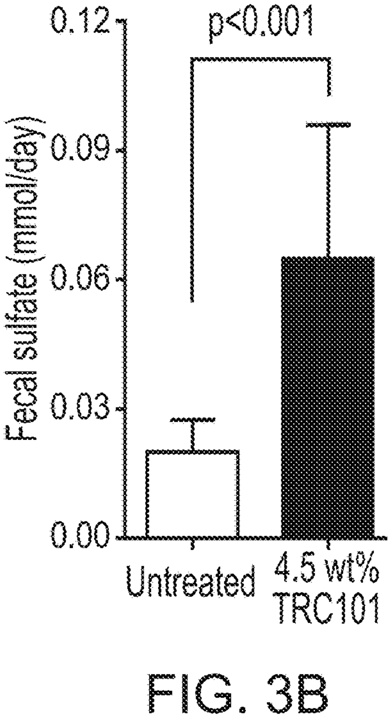
Figure 3C:
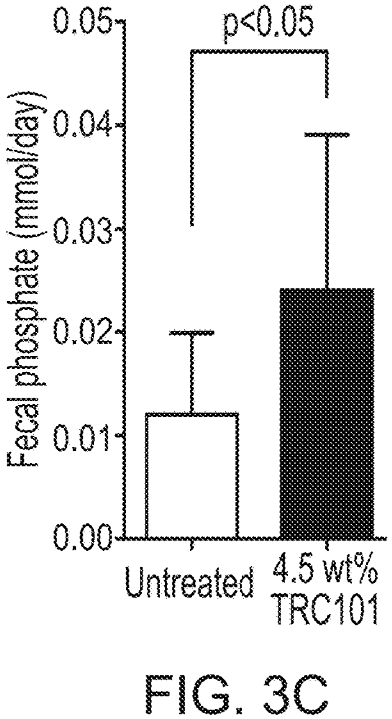

Consistent with the results observed on SBC, recovered fecal samples from animals treated with 4.5 wt % TRC101 in Part 1 of the study demonstrated a significant 15-fold increase in fecal Cl relative to untreated controls (FIG. 3). TRC101 also significantly increased fecal $SO_4$ and $PO_4$ excretion, but the effect was much less (3- and 2-fold increase, respectively, compared to untreated controls) than that observed for Cl.

Figure 4:
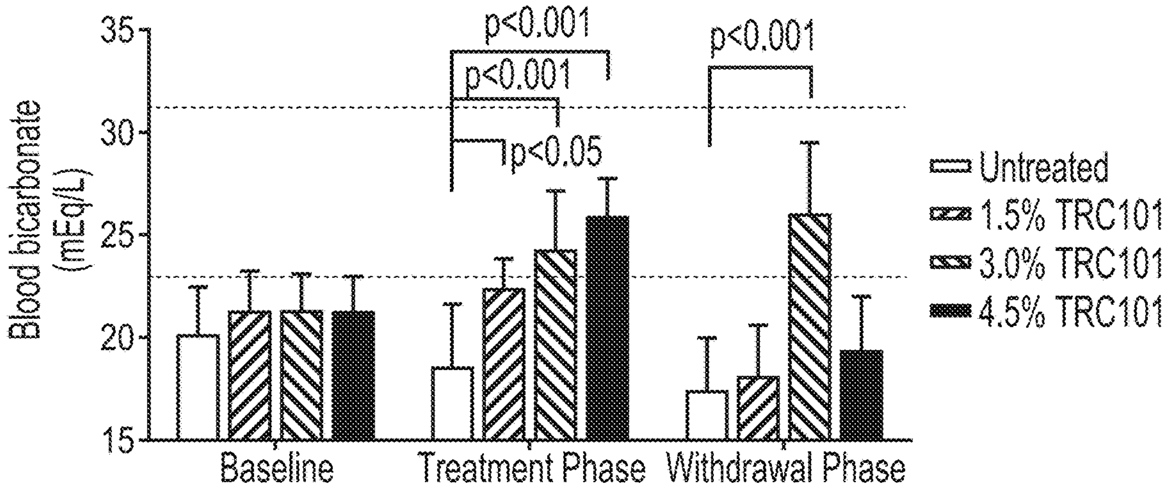
FIG. 4 is a graph of the effect of TRC101 on serum bicarbonate in a rat model of adenine-induced nephropathy and metabolic acidosis in Part 2 of the study described in Example 1.
Figure 5A:
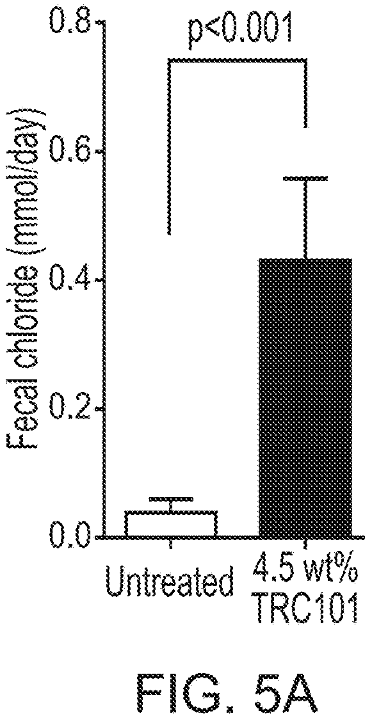
FIGS. 5A, 5B and 5C are graphs of the effect of TRC101 on fecal excretion of chloride (FIG. 5A), sulfate (FIG. 5B), and phosphate (FIG. 5C) in a rat model of adenine-induced nephropathy and metabolic acidosis in Part 2 of the study described in Example 1.
Figure 5B:
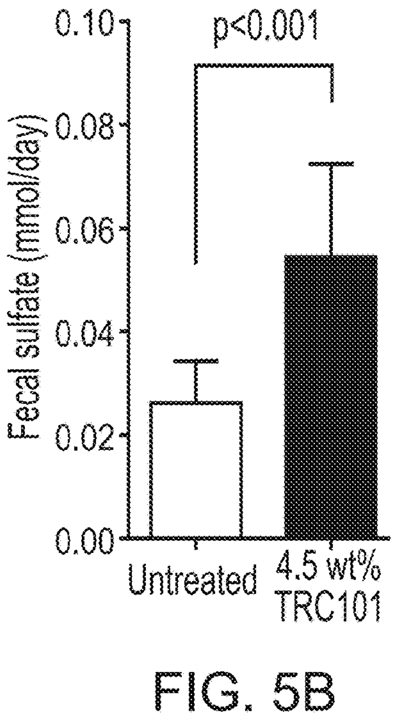
Figure 5C:
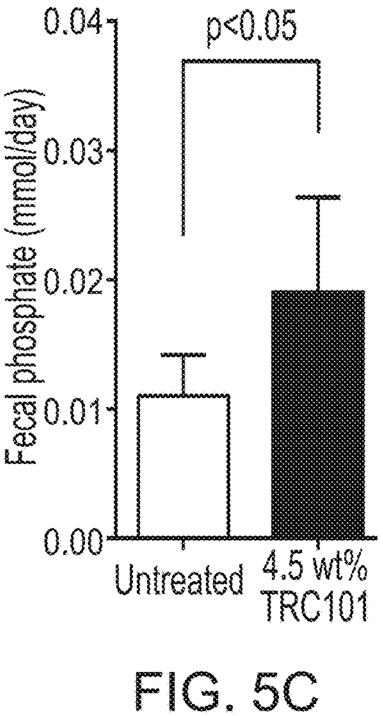

In Part 2 of the study, maintaining rats for a total of 7 weeks on adenine-containing diet prior to the start of the Treatment Phase resulted in mean baseline SBC values that were below the normal range in all treatment groups at a mean of approximately 20 to 21 mEq/L. Treatments with TRC101 resulted in a significant, dose-dependent increase in SBC in all treated groups, relative to the untreated controls. At the end of the 4-week treatment period, mean SBC levels in control animals remained below the normal range. The mean SBC level at the low dose (1.5 wt % TRC101) was only marginally below normal range. At the mid (3.0 wt %) and high (4.5 wt %) doses of TRC101, mean SBC values remained within the normal range (FIG. 4; 2-way ANOVA with Dunnett's multiple comparisons test vs. untreated group; horizontal dotted lines marked the normal SBC range for male Sprague-Dawley rates of the same age). Similar to the results observed in Part 1 of the study, withdrawal of TRC101 administration in Part 2 resulted in a decrease in mean SBC to below the normal range in the low and high doses treatment groups; whereas, continued treatment with 3.0 wt % TRC101 maintained mean SBC levels within the normal range (FIG. 5). The mean SBC level in the 3.0 wt % TRC101 group remained significantly higher than that of the untreated control group throughout the study.

Consistent with the results observed on SBC, recovered fecal samples from animals treated with 4.5 wt % TRC101 in Part 2 of the study demonstrated a significant 10-fold increase in fecal Cl relative to controls, but only a 2-fold increase in fecal $SO_4$ and $PO_4$ excretion (FIG. 5).

Example 2

In Vivo Anion Binding of Polymers in a Pig with Normal Renal Function

The anion binding capacities of TRC101 (as described in Example 1) was evaluated in vivo in a female Yorkshire pig with normal renal function. A comparative experiment was conducted using the free amine form of bixalomer (approved in Japan), an anion-binding resin designed to bind phosphate and available commercially to treat hyperphosphatemia. TRC101 and the free amine form of bixalomer were each individually sealed in nylon sachets (with a 64 micrometer mesh size and differentiated for each polymer by sachet shape), fed to a single pig at a total dose of 2 g for each polymer (i.e., 10 sachets each), and then the polymers were recovered from the sachets collected in the feces over a 10-day period (seven and six sachets were recovered from feces for bixalomer and TRC101, respectively). Bound anions were extracted from the polymers by incubating with NaOH for 18 hours. The anion concentrations in the samples were determined in supernatant by IC.

Figures 6A, 6B, 6C:
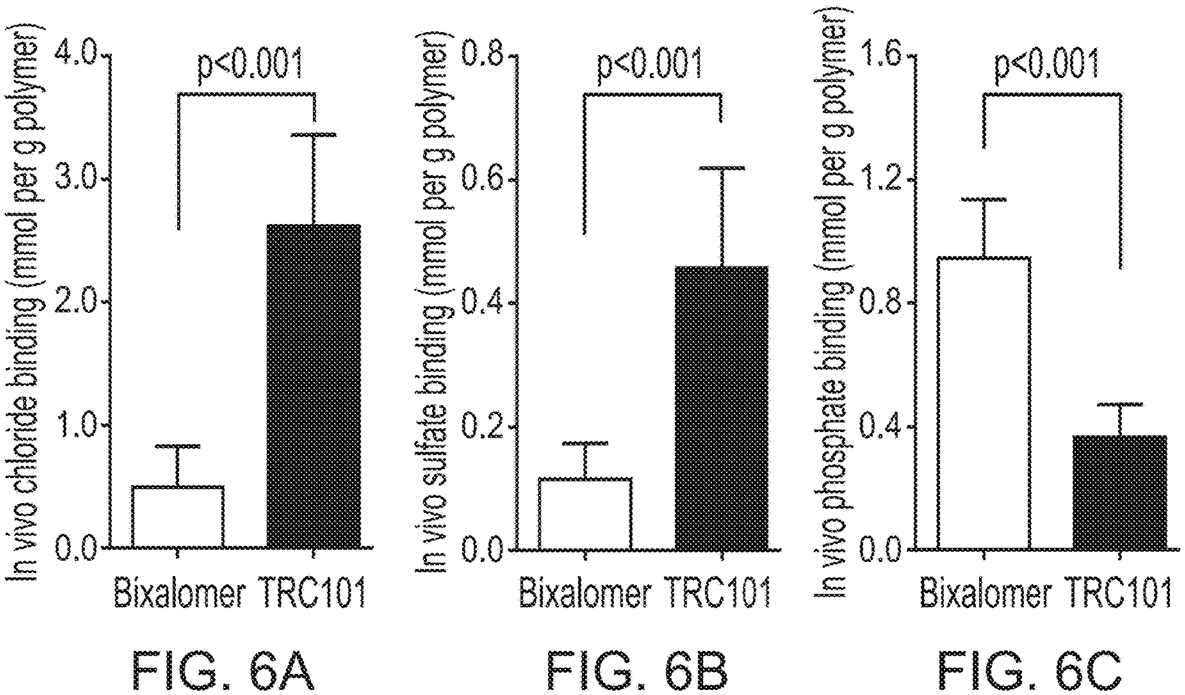
FIGS. 6A, 6B and 6C are graphs of the in vivo chloride (FIG. 6A), sulfate (FIG. 6B) and phosphate (FIG. 6C) binding capacities of test compound and bixalomer in a pig with normal renal function in the study described in Example 2.

Analysis of the anions bound to the polymers after recovery from the feces revealed in vivo average binding of 2.62 and 0.50 mEq of chloride, 0.46 and 0.11 mmol of sulfate, and 0.37 and 0.95 mmol of phosphate per gram of TRC101 and bixalomer, respectively (FIG. 6I statistical analysis unpaired T test; Mean±standard deviation; N=7 and 6 sachets for Bixalomer and TRC101, respectively). Therefore, TRC101 removed 5- and 4-fold more chloride and sulfate, respectively, than bixalomer removed from the GI tract of the pig. On the other hand, bixalomer, a phosphate binder, removed 2.5-fold more phosphate than TRC101 removed from the GI tract of the pig.

Example 3

Efficacy of TRC101 in Subjects with Chronic Kidney Disease and Low Serum Bicarbonate Levels Part 1

TRC101 (as described in Example 1) was studied in a double-blind, placebo-controlled, parallel-design, 4-arm, fixed dose study to evaluate the ability of TRC101 to control serum bicarbonate (SBC) in human subjects with marked metabolic acidosis. A total of 101 subjects with chronic kidney disease (CKD) and low SBC values were randomized into one of the four arms in an approximately 1:1:1:1 ratio (total daily doses of 3, 6 or 9 g/day TRC101 or 3 g/day placebo [microcrystalline cellulose], administered twice daily [BID]).

Subjects were eligible for inclusion in the study if they were 18 to 80 years of age, had Stage 3 or 4 CKD (estimated glomerular filtration rate [eGFR], 20 to <60 mL/min/1.73 $m^2$ of body surface area) and SBC levels of 12 to 20 mEq/L (inclusive) at both Screening and study Day −1, had systolic blood pressure (SBP) at Screening <170 mmHg, had a hemoglobin A1c (HbA1c) value of ≤9.0% and a fasting serum glucose (FSG) value of ≤250 mg/dL (13.9 mmol/L) at Screening. Key exclusion criteria were history of anuria, dialysis, acute kidney injury, acute renal insufficiency or >30% increase in serum creatinine or 30% decrease in eGFR in the past 3 month, severe comorbid conditions (other than CKD) such as congestive heart failure with maximum New York Heart Association (NYHA) Class III or IV symptoms, unstable angina or acute coronary syndrome, dementia, hypertensive urgency or emergency, transient ischemic attack, stroke, or use of home oxygen during the 6 months prior to Screening. Other exclusion criteria were serum potassium values of <3.8 mEq/L or >5.9 mEq/L at Screening, Type 1 diabetes or chronic obstructive pulmonary disease, history or current diagnosis of heart or kidney transplant, clinically significant diabetic gastroparesis, bariatric surgery, bowel obstruction, swallowing disorders, severe gastrointestinal disorders, severe recurrent diarrhea or severe recurrent constipation.

At the time of Screening, subjects who met all the entry criteria were admitted to the Clinical Research Unit (CRU) on Day −1 and placed on a study diet controlled for protein, caloric content, anions, cations and fiber, in accordance with dietary recommendations for patients with CKD (KDOQI, 2003). The potential renal acid load (i.e., PRAL value) (Scialla, 2013) was calculated for the daily meal plans to ensure that the study diet was neither acidic nor basic; PRAL values for the four daily meal plans ranged from −1.71 to +1.92 and averaged 0.82. The PRAL is calculated as follows:

$$PRAL(mEq/d) = 0.49 * \text{protein [g/d]} + (0.037 * \text{phosphorus [mg/d]}) - (0.21 * \text{potassium [mg/d]}) - (0.26 * \text{magnesium [mg/d]}) - 0.013 * (\text{calcium [mg/d]})$$

Four detailed meal plans were developed that specified the foods (including measured quantities) provided at breakfast, lunch, dinner and two light snacks each day (Table S-5). Care was taken to ensure the diet closely approximated the subjects' typical diet so that perturbations in serum bicarbonate related to a sudden change in diet would be minimized. The dietary sources of protein were predominantly plant-based. Meat (i.e., pork, fish) was served once per day on two of the four meal plans. The sites rotated among the four daily meal plans over the course of the treatment period. The mean (±standard deviation) serum bicarbonate level in the placebo group was 17.6 (±1.43) mEq/L at baseline and remained constant during the 14-day treatment period (17.5 [±1.87] mEq/L at Day 15), demonstrating that the study diet did not change the level of serum bicarbonate.

No subject was withdrawn early from the study for any reason. The majority of subjects were male (65%), all subjects were white, and the median age was 61 years (range: 30 to 79 years).

Subjects in the study had Stage 3-4 CKD (39% with Stage 4) with a mean baseline eGFR of 36.4 mL/min/1.73 $m^2$ (range 19.0 to 66.0 mL/min/1.73 $m^2$) and metabolic acidosis characterized by a mean SBC level of 17.6 mEq/L (range 14.1-20.4 mEq/L). At baseline, 60% of subjects had an SBC value of 12-18 mEq/L and 40% had an SBC value of >18-20 mEq/L.

Subjects had baseline comorbidities common in CKD patients including hypertension (93%), diabetes (73%), left ventricular hypertrophy (30%), and congestive heart failure (21%). As would be expected in a CKD Stage 3-4 population, nearly all study subjects had indications for sodium restriction: hypertension (93%), congestive heart failure (21%), peripheral edema (15%) and use of diuretics (41%).

Over a 2-week treatment period, TRC101 significantly increased SBC levels in the study population of CKD patients with baseline SBC levels ranging from 14 to 20 mEq/L. At Day 15, all three doses tested (3, 6 and 9 g/day TRC101 BID) significantly (p<0.0001) increased mean SBC levels from baseline and each dose increased SBC levels to a significantly (p<0.0001) greater extent than placebo.

TABLE S-5

Composition of Study Treatment Period Diet

| Parameter | Calories | Protein (g) | Ca (mg) | Mg (mg) | P (mg) | K (mg) | Na (mg) | Fiber (g) | PRAL |
|---|---|---|---|---|---|---|---|---|---|
| Mean | 2209.25 | 52.32 | 810 | 232.5 | 1008.125 | 2171.375 | 2249.5 | 27.022 | 0.82 |
| Range | 2129-2246 | 50.6-53.4 | 778-849 | 210-235 | 991-1060 | 2048-2277 | 2076-2370 | 22.9-32.1 | −1.71-+1.92 |

Ca = calcium;
K = potassium;
Mg = magnesium;
Na = sodium;
P = phosphate

Enrolled subjects were randomized to one of three TRC101 doses or placebo on Day −1 and dosing was initiated in the morning on Day 1 (next day) in accordance with the randomization assignment. 101 subjects were randomized in an approximately 1:1:1:1 ratio to one of the following groups: Group 1. 3 g/day of placebo administered in equally divided doses BID for 14 days (n=25); Group 2. 3 g/day of TRC101 administered in equally divided doses BID for 14 days (n=25); Group 3. 6 g/day of TRC101 administered in equally divided doses BID for 14 days (n=25); Group 4. 9 g/day of TRC101 administered in equally divided doses BID for 14 days (n=26). TRC101 or placebo were administered orally as an aqueous suspension BID, with breakfast and dinner. The first dose of study drug was taken with breakfast. One hour prior to the administration of the study drug, venous blood was drawn for a pre-dose SBC (contributing to the baseline SBC value) and safety laboratory measurements. Subjects remained in the CRU and continued BID dosing with study drug (at breakfast and dinner) for 14 days. On Day 15, subjects were discharged from the CRU. All subjects who completed the study had a discharge assessment on Day 15 and returned to the CRU on Day 17 and Day 21 for AE collection, blood draws and safety assessments. A subset of patients (n=41) also returned to the CRU on Day 28 for AE collection, blood draws and safety assessments.

Figure 7:
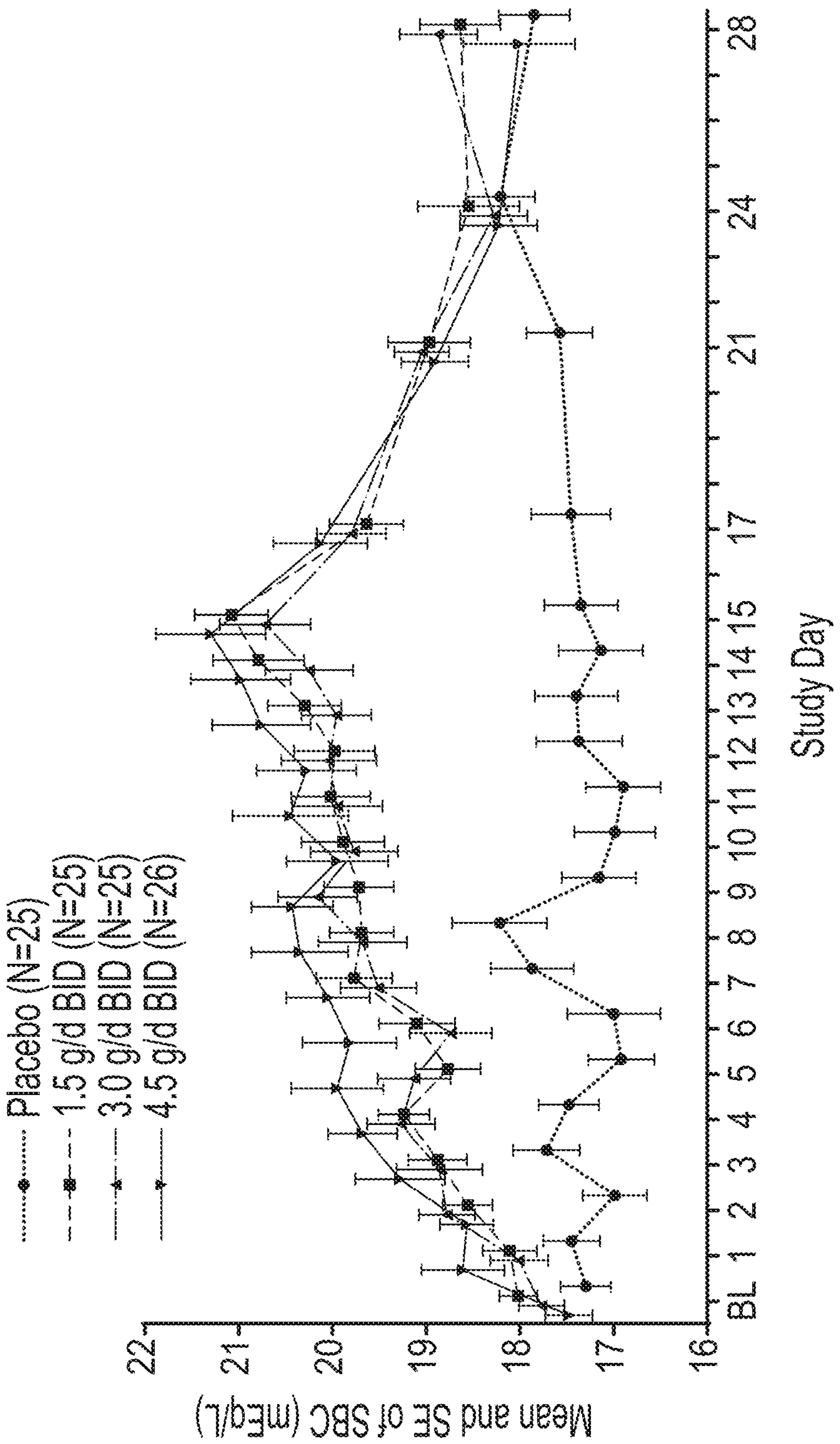
FIG. 7 is a line graph showing the mean change in serum bicarbonate (SBC) from baseline (BL) and standard error (SE) by treatment group over time in a human study as described more fully in Example 3 (Part 1).

FIG. 7 illustrates the steady increase in mean SBC observed in all three TRC101 dose groups during the 14-day treatment period with a mean increase at the end of treatment of approximately 3-4 mEq/L across all three active dose groups. Serum bicarbonate levels in the placebo group remained essentially unchanged throughout the study, suggesting that the diet with a controlled protein and cation/anion content administered in the clinical research unit matched well with what the subjects are at home and, therefore, had no significant impact on their SBC values.

TRC101 had a rapid onset of action (i.e., statistically significant increase in mean within group change from baseline in SBC; p<0.0001) within the first 24-48 hours following the initiation of treatment for all three TRC101 dose groups combined. The onset of action for between-group differences (active vs. placebo) appear to occur between 48-72 hours after the initiation of treatment with TRC101. At Day 4 (72 hours after the first dose of TRC101), the mean increase in SBC from baseline for each TRC101 group was 1-2 mEq/L: 3 g/day (p=0.0011); 6 g/day (p=0.0001); 9 g/day (p<0.0001).

Each of the TRC101 dose groups showed a statistically significant (p<0.0001) increase from baseline in SBC of approximately 3-4 mEq/L after 2 weeks of treatment (see Table 1).

TABLE 1

Change from Baseline in SBC at Day 15

| | Placebo (N = 25) | TRC101 3 g/d BID (N = 25) | TRC101 6 g/d BID (N = 25) | TRC101 9 g/d BID (N = 26) | TRC101 Combined (N = 76) |
|---|---|---|---|---|---|
| Baseline | | | | | |
| n | 25 | 25 | 25 | 26 | 76 |
| Mean (SD) | 17.30 (1.338) | 18.02 (1.009) | 17.77 (1.212) | 17.48 (1.282) | 17.75 (1.180) |
| Median | 17.40 | 17.90 | 17.80 | 17.73 | 17.83 |
| Min, Max | 14.1, 19.6 | 15.6, 20.4 | 15.4, 19.9 | 14.5, 19.2 | 14.5, 20.4 |
| Day 15 | | | | | |
| n | 25 | 25 | 25 | 26 | 76 |
| Mean (SD) | 17.35 (1.958) | 21.08 (1.960) | 20.72 (2.423) | 21.30 (2.977) | 21.04 (2.475) |
| Median | 17.00 | 21.30 | 20.50 | 21.45 | 21.20 |
| Min, Max | 14.1, 21.7 | 17.3, 24.8 | 15.4, 25.9 | 15.1, 27.0 | 15.1, 27.0 |
| Day 15 Change from Baseline (CFB) | | | | | |
| n | 25 | 25 | 25 | 26 | 76 |
| Mean (SD) | 0.05 (1.955) | 3.06 (2.209) | 2.95 (2.625) | 3.83 (2.372) | 3.29 (2.408) |
| Median | −0.10 | 3.55 | 2.40 | 3.23 | 3.07 |
| Min, Max | −3.5, 4.6 | −1.6, 7.5 | −1.5, 8.6 | −0.4, 9.2 | −1.6, 9.2 |
| Within Group CFB | | | | | |
| LS Mean (SEM) | −0.10 (0.414) | 3.21 (0.415) | 3.04 (0.414) | 3.74 (0.406) | 3.33 (0.237) |
| 95% CI of LS Mean | −0.91, 0.71 | 2.39, 4.02 | 2.23, 3.85 | 2.95, 4.54 | 2.86, 3.80 |
| p-value | 0.8109 | <.0001 | <.0001 | <.0001 | <.0001 |
| Between Group CFB Difference (TRC101-Placebo) | | | | | |
| LS Mean (SEM) | NA | 3.31 (0.588) | 3.14 (0.587) | 3.84 (0.579) | 3.43 (0.478) |
| 95% CI of LS Mean | NA | 2.15, 4.46 | 1.99, 4.29 | 2.70, 4.98 | 2.49, 4.37 |
| p-value | NA | <.0001 | <.0001 | <.0001 | <.0001 |

Note:
baseline serum bicarbonate (SBC) is defined as an average of two SBC values from samples collected on Day −1 and at Day 1 pre-dose. Change from baseline (CFB) is defined as post-baseline value minus baseline value.
Note:
Least squares (LS) mean, standard error of LS mean (SEM), 95% CI of LS mean, and p-values are based on the mixed-effect repeated measures model with the CFB in SBC value as the dependent variable; treatment (placebo, 3 g/d BID, 6 g/d BID, and 9 g/d BID), time point (Days 2 through 15), and treatment by time point as fixed effects; subject as a random effect; and baseline estimated glomerular filtration rate (eGFR) and baseline SBC as continuous covariates. Within-subject correlations are modeled assuming a first-order autoregressive covariance structure.

Figure 8:
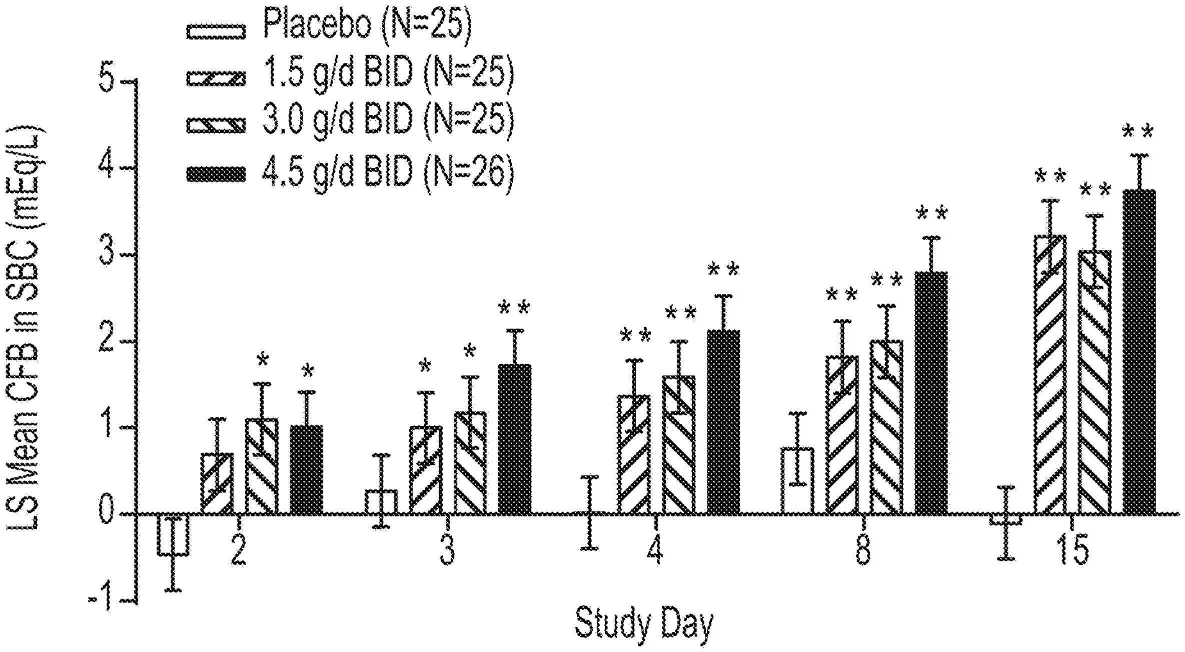
FIG. 8 is a bar graph showing the least squares mean (LS Mean) change from baseline (CFB) to end of treatment in serum bicarbonate (SBC) by treatment group in a human study as described more fully in Example 3 (Part 1). Single asterisk ("*") indicates statistically significant difference ($p<0.5$) and double asterisk ("**") indicates highly statistically significant difference ($p<0.0001$).

There appeared to be little difference in efficacy between the 3 g/day and 6 g/day TRC101 doses; however, subjects in the 9 g/day TRC101 dose group demonstrated a more rapid and larger increase in SBC. For example, the mean increases in SBC at Day 8 were 1.82, 2.00, and 2.79 mEq/L in the 3, 6 and 9 g/day TRC101 dose groups respectively (i.e., ~0.8-1.0 mEq/L difference between the 9 g/day dose group and the other two TRC101 dose groups). At Day 15, the comparable SBC increases were 3.21, 3.04, and 3.74 mEq/L, respectively (i.e., ~0.5-0.7 mEq/L difference between the 9 g/day dose group and the other two TRC101 dose groups) (FIG. 8)).

Statistically significant between-group (active vs. placebo) differences in SBC change from baseline to Day 15 ranged from 3.14 to 3.84 mEq/L across the TRC101 treatment groups, with a combined mean difference of 3.43 mEq/L between TRC101 and placebo ($p<0.0001$) (see Table 1).

As shown in Table 2, after 2 weeks of treatment, SBC levels increased by ≥23 mEq/L in over half of subjects (52.6%) in the combined TRC101 group compared to 8.0% of subjects in the placebo group ($p<0.0001$). In addition, 22.4% of all TRC101-treated subjects had increases in SBC≥25 mEq/L compared to 0 subjects in the placebo group.

TABLE 2

Change in SBC by Category over Time

| Subjects with Post Baseline SBC | Placebo N = 25 | TRC101 3 g/d N = 25 | TRC101 6 g/d N = 25 | TRC101 9 g/d N = 26 | TRC101 Combined N = 76 |
|---|---|---|---|---|---|
| Day 15 Increase from Baseline | | | | | |
| ≥2 mEq/L | 4 (16.0%) | 18 (72.0%) | 14 (56.0%) | 19 (73.1%) | 1 (67.1%) |
| ≥3 mEq/L | 2 (8.0%) | 14 (56.0%) | 10 (40.0%) | 16 (61.5%) | 40 (52.6%) |

TABLE 2-continued

| Change in SBC by Category over Time | | | | | |
|---|---|---|---|---|---|
| Subjects with Post Baseline SBC | Placebo N = 25 | TRC101 3 g/d N = 25 | TRC101 6 g/d N = 25 | TRC101 9 g/d N = 26 | TRC101 Combined N = 76 |
| ≥4 mEq/L | 1 (4.0%) | 8 (32.0%) | 10 (40.0%) | 11 (42.3%) | 29 (38.2%) |
| ≥5 mEq/L | 0 | 3 (12.0%) | 6 (24.0%) | 8 (30.8%) | 17 (22.4%) |
| ≥6 mEq/L | 0 | 3 (12.0%) | 3 (12.0%) | 4 (15.4%) | 10 (13.2%) |
| ≥7 mEq/L | 0 | 1 (4.0%) | 2 (8.0%) | 2 (7.7%) | 5 (6.6%) |

In the combined TRC101 treatment group, 35.5% of subjects had their SBC corrected into the normal range (22-29 mEq/L) after 2 weeks of treatment, and at the end of the treatment period, 64.5% of TRC101-treated subjects had SBC levels that were above the upper limit of the baseline range (>20 mEq/L) (Table 3). The proportion of subjects achieving an SBC>22 mEq/L was similar in the 3, 6 and 9 g/day TRC101 dose groups (40.0%, 28.0%, and 38.5%, respectively). At Day 8 of the treatment period, only about half of the treatment effect was seen, again suggesting that the SBC increase has not yet plateaued by the end of the 2-week treatment period.

TABLE 3

| Change in SBC by Category over Time | | | | | |
|---|---|---|---|---|---|
| Subjects with Post Baseline SBC | Placebo N = 25 | TRC101 3 g/d N = 25 | TRC101 6 g/d N = 25 | TRC101 9 g/d N = 26 | TRC101 Combined N = 76 |
| Day 8 SBC Values | | | | | |
| >20 mEq/L | 3 (12.0%) | 9 (36.0%) | 7 (28.0%) | 12 (46.2%) | 28 (36.8%) |
| >22 mEq/L | 2 (8.0%) | 2 (8.0%) | 5 (20.0%) | 6 (23.1%) | 13 (17.1%) |
| >27 mEq/L | 0 | 0 | 0 | 0 | 0 |
| >29 mEq/L | 0 | 0 | 0 | 0 | 0 |
| Day 15 SBC Values | | | | | |
| >20 mEq/L | 2 (8.0%) | 16 (64.0%) | 14 (56.0%) | 19 (73.1%) | 49 (64.5%) |
| >22 mEq/L | 0 | 10 (40.0%) | 7 (28.0%) | 10 (38.5%) | 27 (35.5%) |
| >27 mEq/L | 0 | 0 | 0 | 0 | 0 |
| >29 mEq/L | 0 | 0 | 0 | 0 | 0 |

Figure 9:
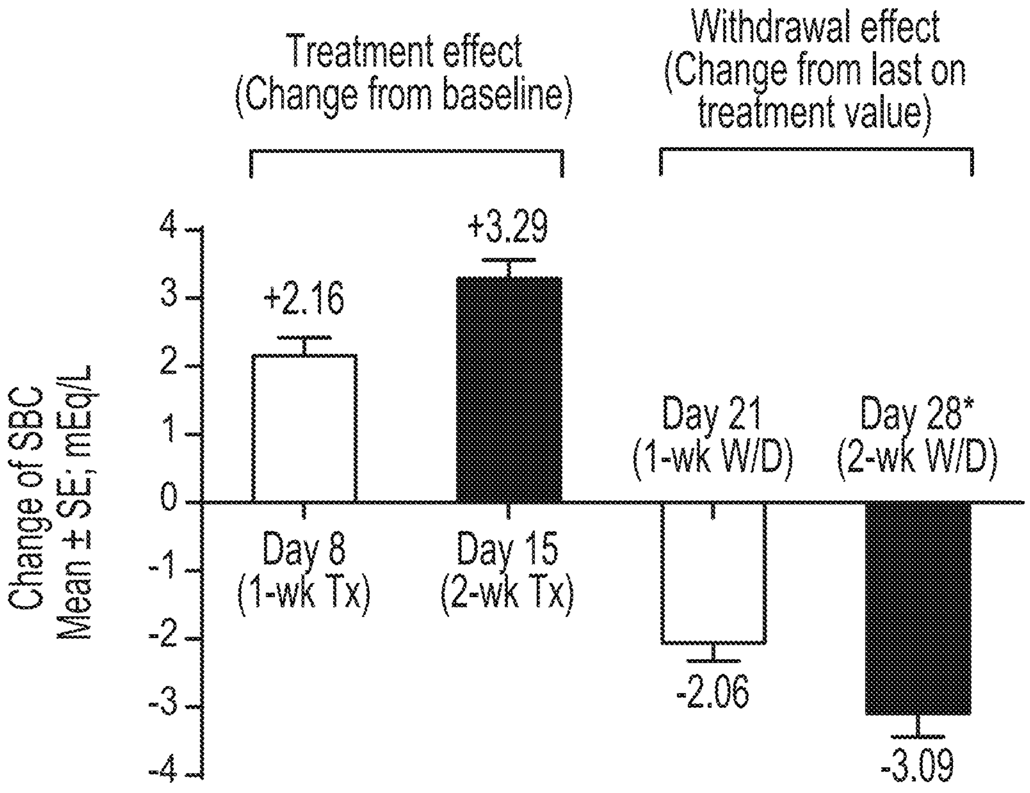
FIG. 9 is a bar graph showing the effect on serum bicarbonate (SBC) levels and standard error (SE) at days 8 and 15 resulting from treatment (Tx=treatment) and upon withdrawal of TRC101 in a human study as described more fully in Example 3 (Part 1).

The 2-week treatment period in the study was followed by a 2-week follow-up period in which subjects were off treatment. At the end of the 2-week follow-up period, a withdrawal effect of approximately 3 mEq/L was observed in the combined TRC101 group, with SBC levels returning nearly to baseline (FIG. 9). These results underscore the chronic nature of the underlying metabolic acidosis in these CKD patients, and suggest that continued treatment with TRC101 is needed to maintain elevated SBC levels.

There were no mean changes in serum parameters (sodium, calcium, potassium, phosphate, magnesium, low density lipoprotein) observed in the study that would indicate off-target effects of TRC101; there were also no mean changes in serum chloride.

Part 2

The double-blind, placebo-controlled, parallel-design, fixed dose study of Part 1 was extended by the introduction of two additional arms: a total of 34 subjects with chronic (CKD) and low SBC values were randomized into one of two additional arms: total daily dose of 6 g/day TRC101 (28 subjects) or 3 g/day placebo (6 subjects) [microcrystalline cellulose], administered once daily [QD]). All subjects who completed Part 2 of the study had a discharge assessment on Day 15 and returned to the CRU on Day 17, Day 21, and Day 28 for AE collection, blood draws and safety assessments. Part 2 of the study was otherwise unchanged from Part 1.

Discussion of Part 1 and Part 2 Study Results

There were no significant differences between the TRC101 and placebo treatment groups with respect to demographics, baseline eGFR or serum bicarbonate, or comorbidities (Table 4). Patients had a mean baseline eGFR of 34.8 mL/min/1.73 m2 and a mean baseline serum bicarbonate level of 17.7 mEq/L. Study participants had conditions common to CKD patients, including patients with hypertension (93.3%), diabetes (69.6%), left ventricular hypertrophy (28.9%), congestive heart failure (21.5%), peripheral edema (14.1%) and stable diuretic use (42.2%).

Analysis of the mean serum bicarbonate level in the placebo group over the course of the in-unit treatment period and out-patient follow-up period demonstrated that the study diet did not change the level of serum bicarbonate. The mean (±standard deviation) serum bicarbonate level in the placebo group was 17.6 (±1.43) mEq/L at baseline and remained constant during the 14-day treatment period (17.5 [±1.87] mEq/L at Day 15).

Figure 10:
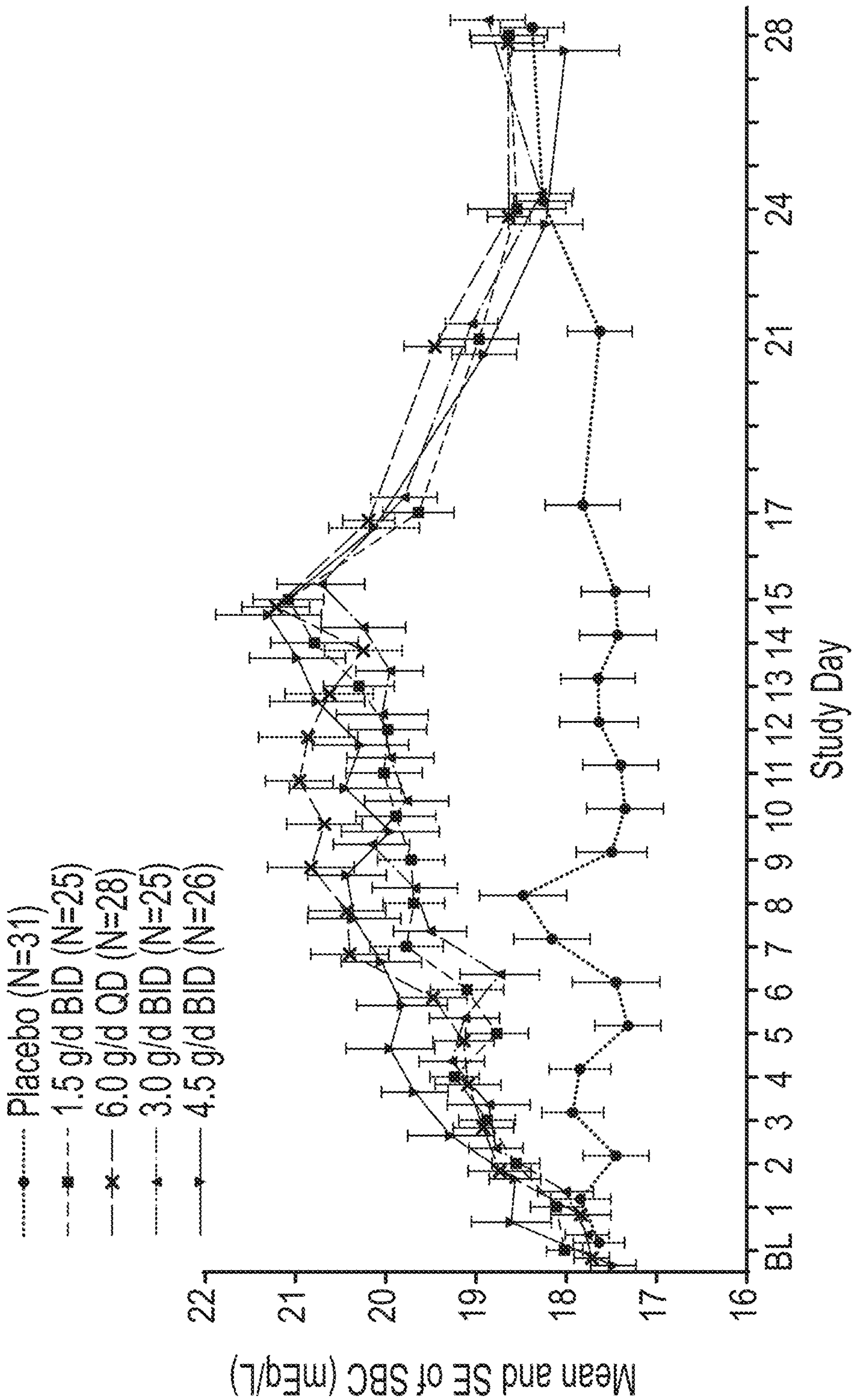
FIG. 10 is a line graph showing the mean change in serum bicarbonate (SBC) and standard error (SE) for the four TRC101 active arms and the two placebo arms (pooled) of the study described more fully in Example 3 (Parts 1 and 2).
Figure 11:
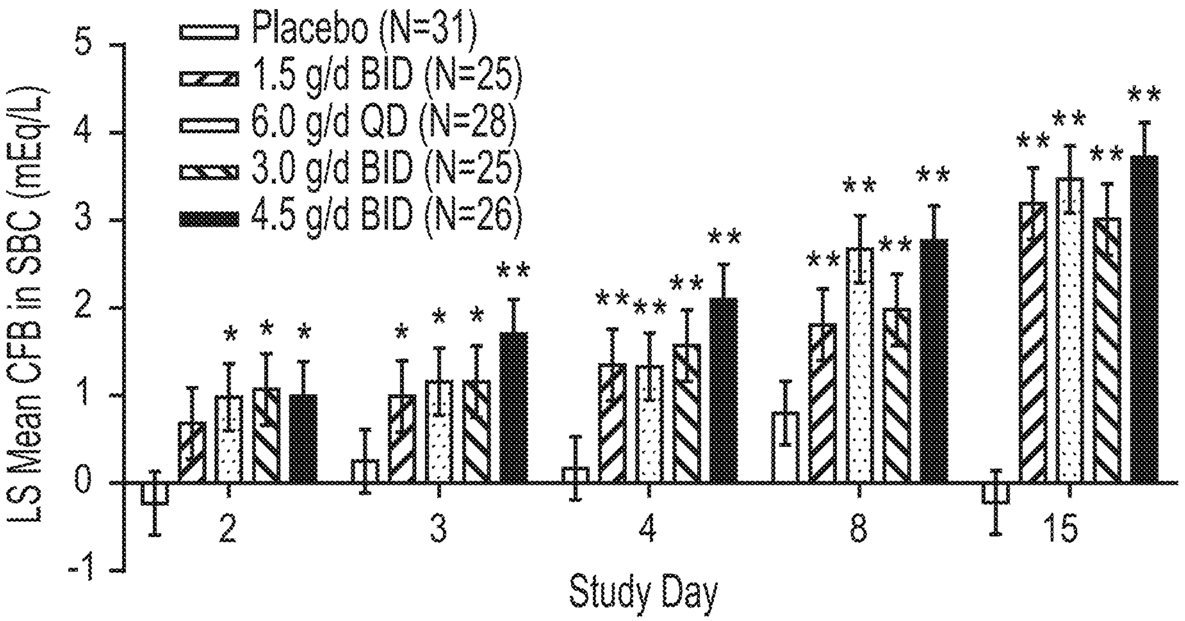
FIG. 11 is a bar graph showing the least squares mean (LS Mean) change from baseline (CFB) in serum bicarbonate (SBC) by treatment group over time for the four TRC101 active arms and the two placebo arms (pooled) of the study described more fully in Example 3 (Parts 1 and 2). Single asterisk ("*") indicates statistically significant difference ($p<0.5$) and double asterisk ("**") indicates highly statistically significant difference ($p<0.0001$).
Figure 12:
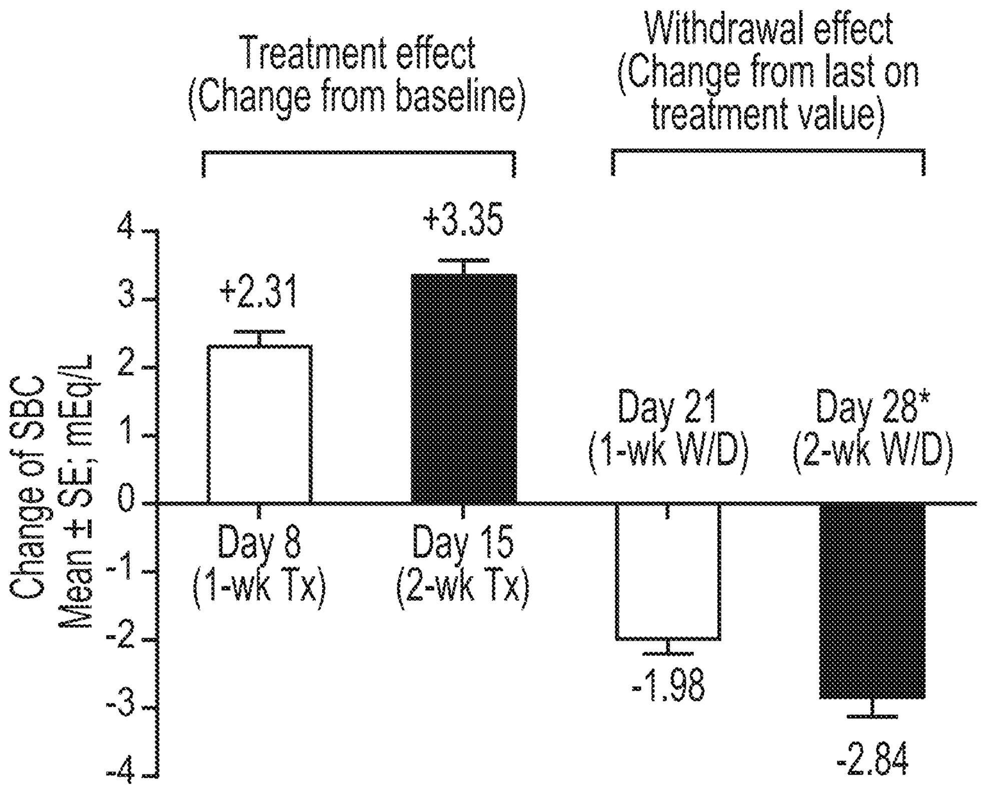
FIG. 12 is a bar graph showing the treatment effect on serum bicarbonate (SBC) levels and standard error (SE) at days 8 and 15 resulting from treatment (Tx=treatment) with and upon withdrawal of TRC101 in a human study as described more fully in Example 3 (Parts 1 and 2).

There was a significant increase in mean serum bicarbonate in all groups treated with TRC101 within the first 24-48 hours compared to placebo (FIGS. 10 & 11). Within 72 hours after the first dose of TRC101, the mean increase in serum bicarbonate from baseline for each TRC101 group was 1-2 mEq/L Over the 2-week treatment period, TRC101 increased serum bicarbonate values over the respective baseline values for each group, while placebo-treated patients had no change in serum bicarbonate (FIGS. 10 & 11). At day 15, the between group difference of serum bicarbonate versus placebo was 3.31 mEq/L (95% Cl of LS mean 2.15 to 4.46;

p<0.0001), 3.14 mEq/L (95% Cl of LS mean 1.99 to 4.29; p<0.0001), 3.84 mEq/L (95% Cl of LS mean 2.70 to 4.98; p<0.0001), and 3.72 mEq/L (95% Cl of LS mean 2.70 to 4.74; p<0.0001), for TRC101 dose groups 1.5 g, 3.0 g, 4.5 g BID and 6 g QD, respectively. By comparison, the placebo within group change from baseline to day 15 was −0.21 mEq/L (95% Cl of LS mean −0.91 to 0.49; p=0.56). The mean increase in the combined TRC101 dose groups was 3.57 mEq/L higher than in the placebo group at the end of the 14-day treatment period (95% Cl of LS mean 2.75 to 4.38; p<0.0001). At day 15 there was no significant difference in the mean serum bicarbonate increase when TRC101 was given as a dose of 6.0 g once daily versus 3.0 g twice daily (−0.53 mEq/L; 95% Cl of LS mean −1.61 to 0.56; p=0.34).

Treatment with TRC101 caused a steady increase in mean serum bicarbonate in all TRC101 dose groups during the 14-day treatment period. The slope of serum bicarbonate increase remained constant, with no evidence of a plateau at the end of treatment, indicating that the maximal increase in serum bicarbonate using the study doses of TRC101 was not established. The change in serum bicarbonate was similar in all groups treated with TRC101 at the end of the treatment period (FIGS. 10 & 11).

After 2 weeks of treatment with TRC101, serum bicarbonate increased by ≥23 mEq/L in over half of the patients (51.9%) in the combined TRC101 dose group, compared to 6.5% of patients in the placebo group (Table 5). In addition, 38.5% and 22.1% of all TRC101-treated patients, compared to 3.2% and 0% of placebo-treated patients, had increases in serum bicarbonate of ≥4 mEq/L and ≥25 mEq/L, respectively.

At the end of TRC101 treatment, 34.6% of patients in the combined TRC101 group had a serum bicarbonate in the normal range (22-29 mEq/L) compared to no patients in the placebo group. At the end of TRC101 dosing, the proportion of patients with a normal serum bicarbonate was similar in the four TRC101 dose groups (40.0%, 28.0%, and 38.5%, 32.1% for 1.5 g BID, 3.0 g BID, 4.5 g BID, and 6.0 g QD, respectively) while none of the patients in the placebo group had a normal serum bicarbonate (Table 6).

At the end of the 2-week, off-treatment, follow-up period, a decrease in serum bicarbonate of approximately 3.0-3.5 mEq/L from the end-of-treatment value was observed in all TRC101 dose groups, with serum bicarbonate levels returning nearly to baseline value in each respective group (FIGS. 10 & 11).

Figure 14:
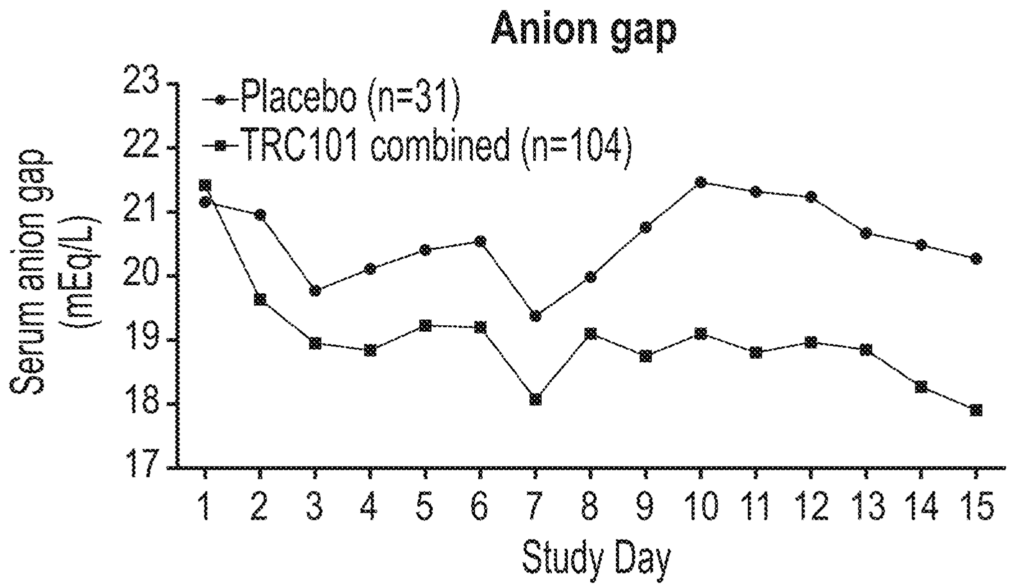
FIG. 14 is a graph showing the changes in the calculated anion gap for the four TRC101 active arms (combined) vs the two placebo arms (pooled) over time for the study described more fully in Example 3 (Parts 1 and 2).

In contrast to serum bicarbonate, serum potassium, serum sodium and serum chloride levels did not significantly change over the course of the study (FIGS. 13A-13D), yielding a change in the serum anion gap in excess of 2 mEq/l (FIG. 14) over the course of the study.

All 135 randomized patients received TRC101 or placebo daily for 14 consecutive days and were included in the safety analysis population. No patients died during the study, or had any adverse events resulting in treatment discontinuation, and no patients suffered serious or severe adverse events. Gastrointestinal adverse events were the most commonly reported events in TRC101-treated patients, and all events were mild or moderate in severity (Table 7). Diarrhea was the most common adverse event; all diarrhea events were mild, self-limited, of short duration, and none required treatment. There were no trends suggesting an off-target effect of TRC101 on electrolytes (i.e., sodium, potassium, magnesium, calcium or phosphate). There were also no trends suggesting an effect of TRC101 on vital signs or ECG intervals. No subject experienced increases in serum bicarbonate that resulted in metabolic alkalosis (i.e., serum bicarbonate >29 mEq/L).

This two-part, double-blind, placebo-controlled, parallel-design, 6-arm, fixed dose clinical study demonstrates that ingestion of TRC101 highly significantly increases serum bicarbonate level in patients with Stage 3 or 4 CKD and low SBC as assessed both by change from baseline within group and by comparisons between active and placebo groups. The rapid onset of action (within 24-72 hours) and efficacy (>3.0 mEq/L increase in SBC) observed in the study suggests that TRC101 is an effective agent in controlling SBC level in the target patient population. Unlike sodium bicarbonate, TRC101 does not introduce cations, such as sodium or potassium, which are deleterious to sodium-sensitive patients with common CKD comorbidities (e.g. hypertension, edema and heart failure). Therefore, TRC101 is expected to provide a safe treatment to control SBC in CKD patients with low SBC, including those who are sodium-sensitive.

TABLE 4

Baseline demographics, dietary intake, renal function, serum bicarbonate and co-morbidities ([a] median values)

| | Placebo Combined N = 31 | TRC101 1.5 g BID N = 25 | TRC101 3.0 g BID N = 25 | TRC101 6 g QD N = 28 | TRC101 4.5 g BID N = 26 | TRC101 Combined N = 104 | Total N = 135 |
|---|---|---|---|---|---|---|---|
| Age[a] (years) | 65.0 | 59.0 | 61.0 | 65.0 | 66.0 | 62.5 | 63.0 |
| Gender (Male/Female) | 19 (61.3%)/ 12 (38.7%) | 19 (76.0%)/ 6 (24.6%) | 17 (68.0%)/ 8 (32.0%) | 16 (57.1%)/ 12 (42.9%) | 15 (57.7%)/ 11 (42.3%) | 68 (65.4%)/ 36 (34.6%) | 87 (64.4%)/ 48 (35.6%) |
| Weight[a], kg | 81.0 | 80.0 | 84.70 | 84.2 | 81.2 | 83.0 | 82.0 |
| Average Daily Protein Intake[a], g/kg/d | 0.64 | 0.65 | 0.61 | 0.62 | 0.64 | 0.63 | 0.63 |
| Diabetes Mellitus (Yes/No) | 20 (64.5%)/ 11 (35.5%) | 18 (72.0%)/ 7 (28.0%) | 20 (80.0%)/ 5 (20.0%) | 17 (60.7%)/ 11 (39.3%) | 19 (73.1%)/ 7 (26.9%) | 74 (71.2%)/ 30 (28.8%) | 94 (69.6%)/ 41 (30.4%) |
| Hypertension (Yes/No) | 30 (96.8%)/ 1 (3.2%) | 24 (96.0%)/ 1 (4.0%) | 23 (92.0%)/ 2 (8.0%) | 26 (92.9%)/ 2 (7.1%) | 23 (88.5%)/ 3 (11.5%) | 96 (92.3%)/ 8 (7.7%) | 126 (93.3%)/ 9 (6.7%) |
| Heart Failure (Yes/No) | 7 (22.6%)/ 24 (77.4%) | 5 (20.0%)/ 20 (80.0%) | 7 (28.0%)/ 18 (72.0%) | 5 (17.9%)/ 23 (82.1%) | 5 (19.2%)/ 21 (80.8%) | 22 (21.1%)/ 82 (78.9%) | 29 (21.5%)/ 106 (78.5%) |
| Left Ventricular Hypertrophy (Yes/No) | 8 (25.8%)/ 23 (74.2%) | 7 (28.0%)/ 18 (72.0) | 7 (28.0%)/ 18 (72.0%) | 8 (28.6%)/ 20 (71.4%) | 9 (34.6%)/ 17 (65.4%) | 31 (29.8%)/ 73 (70.2%) | 39 (28.9%)/ 96 (71.1%) |
| Peripheral Edema (Yes/No) | 4 (12.9%)/ 27 (87.1%) | 3 (12.0%)/ 22 (88.0%) | 4 (16.0%)/ 21 (84.0%) | 4 (14.3%)/ 24 (85.7%) | 4 (15.4%)/ 22 (84.6%) | 15 (14.4%)/ 89 (85.6%) | 19 (14.1%)/ 116 (85.9%) |

TABLE 4-continued

Baseline demographics, dietary intake, renal function, serum bicarbonate and co-morbidities ([a] median values)

| | Placebo Combined N = 31 | TRC101 1.5 g BID N = 25 | TRC101 3.0 g BID N = 25 | TRC101 6 g QD N = 28 | TRC101 4.5 g BID N = 26 | TRC101 Combined N = 104 | Total N = 135 |
|---|---|---|---|---|---|---|---|
| SBP[a], mmHg | 128.00 | 132.00 | 133.00 | 130.00 | 128.50 | 131.50 | 130.00 |
| eGFR[a], m>/min/1.73 $m^2$ | 29.0 | 34.0 | 35.0 | 28.0 | 34.0 | 33.0 | 32.0 |
| SBC[a], mEq/L | 17.6 | 17.9 | 17.8 | 17.7 | 17.7 | 17.8 | 17.7 |

TABLE 5

Proportion of Patients by Serum Bicarbonate Increase Category at Day 15

| Patients with Post-baseline Serum Bicarbonate | Pooled Placebo N = 31 | TRC101 1.5 g BID N = 25 | TRC101 6 g QD N = 28 | TRC101 3.0 g BID N = 25 | TRC101 4.5 g BID N = 26 | TRC101 Combined N = 104 |
|---|---|---|---|---|---|---|
| ≥2 mEq/L | 4 (12.9%) | 18 (72.0%) | 23 (82.1%) | 14 (56.0%) | 19 (73.1%) | 74 (71.2%) |
| ≥3 mEq/L | 2 (6.5%) | 14 (56.0%) | 14 (50.0%) | 10 (40.0%) | 16 (61.5%) | 54 (51.9%) |
| ≥4 mEq/L | 1 (3.2%) | 8 (32.0%) | 11 (39.3%) | 10 (40.0%) | 11 (42.3%) | 40 (38.5%) |
| ≥5 mEq/L | 0 | 3 (12.0%) | 6 (21.4%) | 6 (24.0%) | 8 (30.8%) | 23 (22.1%) |
| ≥6 mEq/L | 0 | 3 (12.0%) | 5 (17.9%) | 3 (12.0%) | 4 (15.4%) | 15 (14.4%) |
| ≥7 mEq/L | 0 | 1 (4.0%) | 1 (3.6%) | 2 (8.0%) | 2 (7.7%) | 6 (5.8%) |

TABLE 6

Proportion of Patients by Serum Bicarbonate Category (Days 8 and 15)

| Patients with Post-baseline Serum Bicarbonate | Pooled Placebo N = 31 | TRC101 1.5 g BID N = 25 | TRC101 6 g QD N = 28 | TRC101 3.0 g BID N = 25 | TRC101 4.5 g BID N = 26 | TRC101 Combined N = 104 |
|---|---|---|---|---|---|---|
| Day 8 Serum Bicarbonate Values | | | | | | |
| >20 mEq/L | 5 (16.1%) | 9 (36.0%) | 16 (57.1%) | 7 (28.0%) | 12 (46.2%) | 44 (42.3%) |
| >22 mEq/L | 2 (6.5%) | 2 (8.0%) | 5 (17.9%) | 5 (20.0%) | 6 (23.1%) | 18 (17.3%) |
| >27 mEq/L | 0 | 0 | 0 | 0 | 0 | 0 |
| >29 mEq/L | 0 | 0 | 0 | 0 | 0 | 0 |
| Day 15 Serum Bicarbonate Values | | | | | | |
| >20 mEq/L | 2 (6.5%) | 16 (64.0%) | 17 (60.7%) | 14 (56.0%) | 19 (73.1%) | 69 (66.3%) |
| >22 mEq/L | 0 | 10 (40.0%) | 9 (32.1%) | 7 (28.0%) | 10 (38.5%) | 36 (34.6%) |
| >27 mEq/L | 0 | 0 | 0 | 0 | 0 | 0 |
| >29 mEq/L | 0 | 0 | 0 | 0 | 0 | 0 |

TABLE 7

Treatmet-Emergent Adverse Events Occurring in >5% of Patients in any Treatment Group (Safety Analysis Set)

| | | TRC101 | | | | | |
|---|---|---|---|---|---|---|---|
| Preferred Term | Pooled Placebo (N = 31) n (%) | 1.5 g BID (N = 25) n (%) | 6 g QD (N = 28) n (%) | 3.0 g BID (N = 25) n (%) | 4.5 g BID (N = 26) n (%) | TRC101 Combined (N = 104) n (%) | Study Total (N = 135) n (%) |
| Patients reporting any TEAE | 14 (45.2) | 13 (52.0) | 17 (60.7) | 9 (36.0) | 17 (65.4) | 56 (53.8) | 70 (51.9) |
| Diarrhea | 4 (12.9) | 9 (36.0) | 3 (10.7) | 3 (12.0) | 6 (23.1) | 21 (20.2) | 25 (18.5) |
| Headache | 1 (3.2) | 4 (16.0) | 1 (3.6) | 1 (4.0) | 2 (7.7) | 8 (7.7) | 9 (6.7) |
| Constipation | 0 | 1 (4.0) | 3 (10.7) | 1 (4.0) | 2 (7.7) | 7 (6.7) | 7 (5.2) |
| Hyperglycemia | 0 | 0 | 3 (10.7) | 2 (8.0) | 2 (7.7) | 7 (6.7) | 7 (5.2) |
| Hypoglycemia | 2 (6.5) | 2 (8.0) | 0 | 1 (4.0) | 2 (7.7) | 5 (4.8) | 7 (5.2) |

TABLE 7-continued

Treatmet-Emergent Adverse Events Occurring in >5% of Patients in any Treatment Group (Safety Analysis Set)

| | | TRC101 | | | | | |
|---|---|---|---|---|---|---|---|
| Preferred Term | Pooled Placebo (N = 31) n (%) | 1.5 g BID (N = 25) n (%) | 6 g QD (N = 28) n (%) | 3.0 g BID (N = 25) n (%) | 4.5 g BID (N = 26) n (%) | TRC101 Combined (N = 104) n (%) | Study Total (N = 135) n (%) |
| Hypertension | 1 (3.2) | 1 (4.0) | 2 (7.1) | 0 | 2 (7.7) | 5 (4.8) | 6 (4.4) |
| Glomerular filtration rate decreased | 2 (6.5) | 2 (8.0) | 0 | 1 (4.0) | 1 (3.8) | 4 (3.8) | 6 (4.4) |
| Blood glucose increased | 2 (6.5) | 1 (4.0) | 1 (3.6) | 0 | 0 | 2 (1.9) | 4 (3.0) |

BID = twice daily;
GFR = glomerular filtration rate;
QD = once daily;
TEAE = treatment-emergent adverse event.

What is claimed is:

1. A method of treating an individual afflicted with chronic kidney disease (CKD) and metabolic acidosis characterized by a baseline serum bicarbonate value of less than 22 mEq/l, the method comprising oral administration of a pharmaceutical composition to increase the individual's serum bicarbonate levels wherein:
(i) the pharmaceutical composition binds HCl in the individual's digestive system when given orally;
(ii) the pharmaceutical composition increases the serum bicarbonate level by at least 3 mEq/I in a placebo controlled study, said increase being the difference between the cohort average serum bicarbonate level in a first cohort at the end of the study, relative to the cohort average serum bicarbonate level in a second cohort at the end of the study, wherein the first cohort's subjects receive the pharmaceutical composition and the second cohort's subjects receive a placebo, wherein the first and second cohorts each comprise at least 25 subjects, each cohort is prescribed the same diet during the study and the study lasts at least two weeks; and
(iii) the pharmaceutical composition comprise a cross-linked amine polymer that is a copolymer comprising the residues of (1) 2-Propen-1-ylamine or a salt thereof and (b) 1,3-Bis(allylamino)propane or a salt thereof.

2. The method of claim 1, wherein the oral administration is as frequent as at least weekly, is as frequent as at least semi-weekly, or is as frequent as at least daily within the treatment period.

3. The method of claim 1, wherein the metabolic acidosis is characterized by a baseline serum bicarbonate value of less than 18 mEq/l.

4. The method of claim 1, wherein the method increases the serum bicarbonate value from the baseline serum bicarbonate value to an increased serum bicarbonate value of at least 22 mEq/l.

5. The method of claim 1, wherein the clinically significant increase is achieved within a treatment period of less than one month, 25 days, or 3 weeks.

6. The method of claim 1, wherein the individual's serum bicarbonate value returns to the baseline value ±2 mEq/I within 1 month, 3 weeks or 2 weeks of the cessation of treatment.

7. The method of claim 1, wherein the baseline serum bicarbonate value is the mean value of at least two serum bicarbonate concentrations for serum samples drawn on different days.

8. The method of claim 2, wherein the daily dose has the capacity to remove at least 7.5 mEq of HCl as it transits the digestive system.

9. The method of claim 2, wherein the daily dose is less than 100 g/day, 30 g/day or 10 g/day.

10. The method of claim 1, wherein the individual is treated for at least several months.

11. The method of claim 1, wherein the crosslinked amine polymer has a theoretical binding capacity for HCl in the range of 2 to 25 mEq/g.

12. The method of claim 1, wherein the crosslinked amine polymer is characterized by a chloride ion binding capacity of at least 1 mEq/g, 1.5 mEq/g, 2 mEq/g, 2.5 mEq/g, 3 mEq/g, 3.5 mEq/g, 4 mEq/g, 4.5 mEq/g, 5 mEq/g, 5.5 mEq/g, or 6 mEq/g, in a SIB assay.

13. The method of claim 1, wherein the crosslinked amine polymer is characterized by a ratio of an amount of bound chloride to bound phosphate in a SIB assay that is at least 0.3:1, 0.5:1, or at least 1:1, respectively.

14. The method of claim 1, wherein the crosslinked amine polymer is prepared in two steps, (i) the first step comprising a concurrent polymerization and crosslinking reaction between (a) 2-Propen-1-ylamine or a salt thereof and (b) 1,3-Bis(allylamino)propane or a salt thereof, to produce a preformed crosslinked amine polymer in which the cross-links are primarily carbon-carbon crosslinks, and a second step in which the preformed amine polymer is further crosslinked in a substitution reaction in which a carbon-nitrogen bond is formed.

15. The method of claim 1, wherein the pharmaceutical composition comprises a crosslinked amine polymer prepared in two steps, (i) the first step comprising a concurrent polymerization and crosslinking reaction between (a) 2-Propen-1-ylamine or a salt thereof and (b) 1,3-Bis(allylamino) propane or a salt thereof to produce a preformed amine polymer, and (ii) a second step in which the preformed amine polymer is further crosslinked in a substitution reaction with dichlorethane.

* * * * *